US007803983B2

(12) United States Patent
Alexandrov et al.

(10) Patent No.: US 7,803,983 B2
(45) Date of Patent: Sep. 28, 2010

(54) NUCLEOTIDE SEQUENCES AND CORRESPONDING POLYPEPTIDES CONFERRING MODULATED PLANT GROWTH RATE AND BIOMASS IN PLANTS

(75) Inventors: Nickolai Alexandrov, Thousand Oaks, CA (US); Vyacheslav Brover, Simi Valley, CA (US); Peter Mascia, Thousand Oaks, CA (US); Kenneth Feldmann, Newbury Park, CA (US); Richard Schneeberger, Van Nuys, CA (US); Greg Nadzan, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/324,093

(22) Filed: Dec. 29, 2005

(65) Prior Publication Data

US 2007/0006345 A1 Jan. 4, 2007

Related U.S. Application Data

(63) Continuation-in-part of application No. 11/172,740, filed on Jun. 30, 2005, now Pat. No. 7,396,979.

(60) Provisional application No. 60/583,631, filed on Jun. 30, 2004, provisional application No. 60/584,526, filed on Jun. 30, 2004, provisional application No. 60/584,800, filed on Jun. 30, 2004.

(51) Int. Cl.
*C12N 15/82* (2006.01)
*C12N 15/87* (2006.01)

(52) U.S. Cl. .................. 800/278; 800/287; 800/290

(58) Field of Classification Search .................. None
See application file for complete search history.

(56) References Cited

U.S. PATENT DOCUMENTS

| 2002/0040490 | A1 | 4/2002 | Gorlach et al. |
| 2004/0025202 | A1 | 2/2004 | Laurie et al. |
| 2004/0034888 | A1 | 2/2004 | Liu et al. |
| 2004/0214272 | A1* | 10/2004 | La Rosa et al. ............ 435/69.1 |
| 2004/0216182 | A1 | 10/2004 | Federspiel et al. |
| 2007/0044171 | A1* | 2/2007 | Kovalic et al. .............. 800/278 |

FOREIGN PATENT DOCUMENTS

| EP | 1033405 A2 | 6/2000 |
| WO | WO97/13843 | 4/1997 |
| WO | WO02/16655 A2 | 2/2002 |
| WO | WO02/052012 A2 | 7/2002 |
| WO | WO2004/058963 A2 | 7/2004 |
| WO | WO02/22675 | 3/2006 |

OTHER PUBLICATIONS

Bustos et al., Plant Cell, 1(9):839-853, 1989.*
Yamamoto et al., Plant Cell Physiol., 35:773-778, 1995.*
Keskin et al., Protein Science, 13:1043-1055, 2004.*
Thornton et al., Nature structural Biology, structural genomics supplement, Nov. 2000.*
Wells, Biochemistry 29:8509-8517, 1990.*
Ngo et al., The Protein Folding Problem and Tertiary Structure Prediction, K. Merz., and S. Le Grand (eds.) pp. 492-495,1994.*
Hanzawa et al. (PNAS, 102:7748-7753, 2005).*
Bork et al. (TIG, 12:425-427, 1996).*
Smith et al. (Nature Biotechnology, 15:1222-1223, 1997).*
Doerks et al., (TIG, 14:248-250, 1998).*
Database NCBI, National Centre for Biotechnology Information, Bethesda, USA; BT004686 At1g26948 [Oryza sativa], Dec. 19, 2005, Buell, C.R.,: "Direct Submission" XP0002389148, Database accession No. ABB47567 abstract.
Database EMBL [Online], Apr. 3, 2002, "Triticum aestivum cDNA clone:whr24p13, 5' end, single read." XP002388817, retrieved from EBI accession No. EM_EST:BJ282051, Database accession No. BJ282051.
Database EMBL [Online], Apr. 3, 2002, "Triticum aestivum cDNA clone:whr24p13, 3' end, single read." XP002388818, retrieved from EBI accession No. EM_EST:BJ287183, Database accession No. BJ287183.
Database EMBL [Online] Nov. 25, 2002, "wle1n.pk0058.d12 wle1n Triticum aestivum cDNA clone wle1n.pk0058.d12 5' end, mRNA sequence." retrieved from EBI accession No. EM_EST:CA632062, Database acession No. CA32062.
Kawura, Kanako et al., "Expression profile of two storage-protein gene familiesin hexaploid wheat revealed by large-scale analysis of expressed sequence tags," Plant Physiology (Rockville), vol. 139, No. 4, Dec. 1, 2005 , pp. 1870-1880, ISSN: 0032-0889.
Database NCBI, National Centre for Biotechnology Information, Bethesa, USA; Oryza sativa chromosome 10, complete sequence. Dec. 19, 2005, Buell, C.R. et al., "Direct Submission" Database accession No. AE016959 abstract.
XP-002378432 ID AK118796, Seki, et al., Nov. 25, 2002.
XP-002173128, Improving plant drought, salt, and freezing tolerance by gene transfer of a single stress-inducible transcription factor, Mie Kasuga, et al., *Nature Biotechnology*, vol. 17 Mar. 1999, pp. 287-291.

(Continued)

*Primary Examiner*—Vinod Kumar
(74) *Attorney, Agent, or Firm*—Birch, Stewart, Kolasch & Birch, LLP

(57) ABSTRACT

The present invention relates to isolated nucleic acid molecules and their corresponding encoded polypeptides able confer the trait of modulated plant size, vegetative growth, organ number, plant architecture, growth rate, seedling vigor and/or biomass in plants. The present invention further relates to the use of these nucleic acid molecules and polypeptides in making transgenic plants, plant cells, plant materials or seeds of a plant having plant size, vegetative growth, organ number, plant architecture, growth rate, seedling vigor and/or biomass that are altered with respect to wild type plants grown under similar conditions.

14 Claims, 2 Drawing Sheets

OTHER PUBLICATIONS

XP-002378439, Physiological and molecular insights into drought tolerance, Mundree, et al., *African Journal of Biotechnology*, vol. 1 (2) pp. 28-38, Dec. 2002.

XP-002378470, Plant Responses to drought, salinity and extreme temperatures: towards genetic engineering for stress tolerance, Wang, et al., *Planta* 2003 218: pp. 1-14.

XP008025694, Genetics and genetic improvement of drought resistance in crop plants, Jason Mitra, Western Regional Research Station, Indian Grassland and Fodder Research Institute, Avikanagar 304, 501, Inda, *Current Science*, vol. 80, No. 6 Mar. 25 2001, pp. 758-763.

* cited by examiner

Fig. 1

| Name | | | | | | # |
|---|---|---|---|---|---|---|
| CeresClone:486120 | LLKETCSYIK | SLQREVDDLS | DRLSDLLSTM | DHNSPAAE-- | RSILRS- | 90 |
| gi\|50912765 | LLKETCNYIK | SLHREVDDLS | DRLSDLMATM | DHNSPGAE-- | RSILRS- | 88 |
| CeresClone:503296 | LLKETCSYIK | SLHREVDDLS | DRLSDLMATM | DHNSPGAE-- | RSILRS- | 89 |
| gi\|31431968 | LLKETCSYIK | SLHREVDDLS | ERLSELMATM | DSNSPQAD-- | RSLLR-- | 88 |
| CeresClone:336524 | LLKETCAYVK | SLHREVDDLS | ERLSGLMETM | DNDSPQAE-- | RSLLR-- | 87 |
| gi\|8607 | VLQETCNYIR | NLNKEADDLS | DRLTQLLES- | DPNSPQAAVI | RSLLNG | 94 |
| gi\|22331645 | VLQETCNYIR | NLSKEVDDLS | ERLSQLLES- | -TDSAQAALI | RSLLMQ | 92 |
| CeresClone:18200 | VLQETCNYIR | NLHREVDDLS | DRLSELLAST | DDNSAETA-- | RSLLNY | 94 |
| CeresClone:945972 | VLQDTCNYIR | NLHREVDDLS | DRLSEFLAST | DDNSAEXA-- | ------ | 86 |
| CeresClone:519 | VLQETCNYIR | NLHREVDDLS | ERLSELLAN- | -SDTAQAALI | RSLLTQ | 93 |
| Lead-clone733804-Taxonomy-4565 | VLQETCTYIR | SLHREVDDLS | ERLSELLATS | DMSSAQAAII | RSLLM- | 92 |
| gi\|78708592 | VLQETCSYIR | SLHREVDDLS | ERLAELLAAA | DVSTAQAAVI | RGLLM- | 91 |
| CeresClone:4734 | VLQETCNYIK | SLHREVDDLS | ERLSQLLESV | DEDSPEAAVI | RSLLM- | 92 |
| CeresGdna:1468218 | ILQETCNYIR | NLNREVDNLS | ERLSELLET- | -TDTAQAAII | RNLLMQ | 91 |
| CeresClone:653656 | VLQETCNYIR | SLHREVGDLS | ERLSELLAT- | -TDTAQAAII | RNLLMQ | 92 |
| CeresClone:663844 | VLQETCNYIR | SLHREVGDLS | ERLSELLDT- | -TDTAQAAII | RNLLMQ | 92 |
| CeresGdna:1530225 | VLQETCNYIR | NLHREVDDLS | ERLSQLLATI | DADSPEAAII | RSLLM- | 90 |
| CeresGdna:1449794 | VLQETCNYIK | NLHREVDDLS | ERLSQLLATI | DSDSPEAE-I | RSLLN- | 90 |
| CeresClone:703180 | VLQETCNYIR | SLHREVDDLS | ERLSQLLATI | DADSPEAAII | RSLLM- | 91 |
| CeresClone:560681 | VLQETCNYIR | SLHREVDDLS | ERLSQLLATI | DADSPEAAII | RSLLN- | 91 |
| CeresClone:560948 | VLQETCNYIR | GLHREVSDLS | ERLSQLLTTI | DADSAEAGLI | RSLLNQ | 92 |
| Consensus | VLQETCNYIR | NLHREVDDLS | ERLSELLATM | D-DSPQAAII | RSLL-- | 96 |

NUCLEOTIDE SEQUENCES AND CORRESPONDING POLYPEPTIDES CONFERRING MODULATED PLANT GROWTH RATE AND BIOMASS IN PLANTS

CROSS-REFERENCE TO RELATED APPLICATION

This application is a Continuation-In-Part of application Ser. No. 11/172,740, now U.S. Pat. No. 7,396,979, filed on Jun. 30, 2005, the entire contents of which are hereby incorporated by reference and for which priority is claimed under 35 U.S.C. §120. Application No. 11/172,740 claims priority on Application Nos. 60/583,621 filed on Jun. 30, 2004, No. 60/584,826 filed on Jun. 30, 2004, and 60/584,800 filed on Jun. 30, 2004 under 35 U.S.C §119; the entire contents of all of which are hereby incorporated by reference.

INCORPORATION OF SEQUENCE LISTING

Two copies of the sequence listing (Sequence Listing Copy 1 and Sequence Listing Copy 2) and a computer-readable form of the sequence listing, all on CD-ROMs, each containing the file named 2005-12-29 Sequence Listing 2750-1667PUS1 filed.txt, which is 161 KB (measured in MS-DOS) and was created on Dec. 29, 2005, are herein incorporated by reference.

FIELD OF THE INVENTION

The present invention relates to isolated nucleic acid molecules and their corresponding encoded polypeptides able to modulate plant growth rate, vegetative growth, organ size, architecture seedling vigor and/or biomass in plants. The present invention further relates to using the nucleic acid molecules and polypeptides to make transgenic plants, plant cells, plant materials or seeds of a plant having modulated growth rate, vegetative growth, organ number, architecture, seedling vigor and/or biomass as compared to wild-type plants grown under similar conditions.

BACKGROUND OF THE INVENTION

Plants specifically improved for agriculture, horticulture, biomass conversion, and other industries (e.g. paper industry, plants as production factories for proteins or other compounds) can be obtained using molecular technologies. As an example, great agronomic value can result from modulating the size of a plant as a whole or of any of its organs or the number of any of its organs.

Similarly, modulation of the size and stature of an entire plant, or a particular portion of a plant, or growth rate, or seedling vigor allows production of plants better suited for a particular industry. For example, reductions in the height of specific crops and tree species can be beneficial by allowing easier harvesting. Alternatively, increasing height, thickness or organ size, organ number may be beneficial by providing more biomass useful for processing into food, feed, fuels and/or chemicals (see the US Department of Energy website for Energy Efficiency and Renewable Energy). Other examples of commercially desirable traits include increasing the length of the floral stems of cut flowers, increasing or altering leaf size and shape or enhancing the size of seeds and/or fruits. Changes in organ size, organ number and biomass also result in changes in the mass of constituent molecules such as secondary products and convert the plants into factories for these compounds.

Availability and maintenance of a reproducible stream of food and animal feed to feed animals and people has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed, chemicals and energy for the population.

Manipulation of crop performance has been accomplished conventionally for centuries through plant breeding. The breeding process is, however, both time-consuming and labor-intensive. Furthermore, appropriate breeding programs must be specially designed for each relevant plant species.

On the other hand, great progress has been made in using molecular genetics approaches to manipulate plants to provide better crops. Through introduction and expression of recombinant nucleic acid molecules in plants, researchers are now poised to provide the community with plant species tailored to grow more efficiently and produce more product despite unique geographic and/or climatic environments. These new approaches have the additional advantage of not being limited to one plant species, but instead being applicable to multiple different plant species (Zhang et al. (2004) *Plant Physiol.* 135:615).

Despite this progress, today there continues to be a great need for generally applicable processes that improve forest or agricultural plant growth to suit particular needs depending on specific environmental conditions. To this end, the present invention is directed to advantageously manipulating plant size, organ number, plant growth rate, plant architecture and/or biomass to maximize the benefits of various crops depending on the benefit sought and the particular environment in which the crop must grow, characterized by expression of recombinant DNA molecules in plants. These molecules may be from the plant itself, and simply expressed at a higher or lower level, or the molecules may be from different plant species.

SUMMARY OF THE INVENTION

The present invention, therefore, relates to isolated nucleic acid molecules and polypeptides and their use in making transgenic plants, plant cells, plant materials or seeds of plants having life cycles, particularly plant size, vegetative growth, plant growth rate, organ number, plant architecture and/or biomass, that are altered with respect to wild-type plants grown under similar or identical conditions.

Unless otherwise defined, all technical and scientific terms used herein have the same meaning as commonly understood by one of ordinary skill in the art to which this invention belongs.

DETAILED DESCRIPTION OF THE INVENTION

1. The Invention

Figure 1:
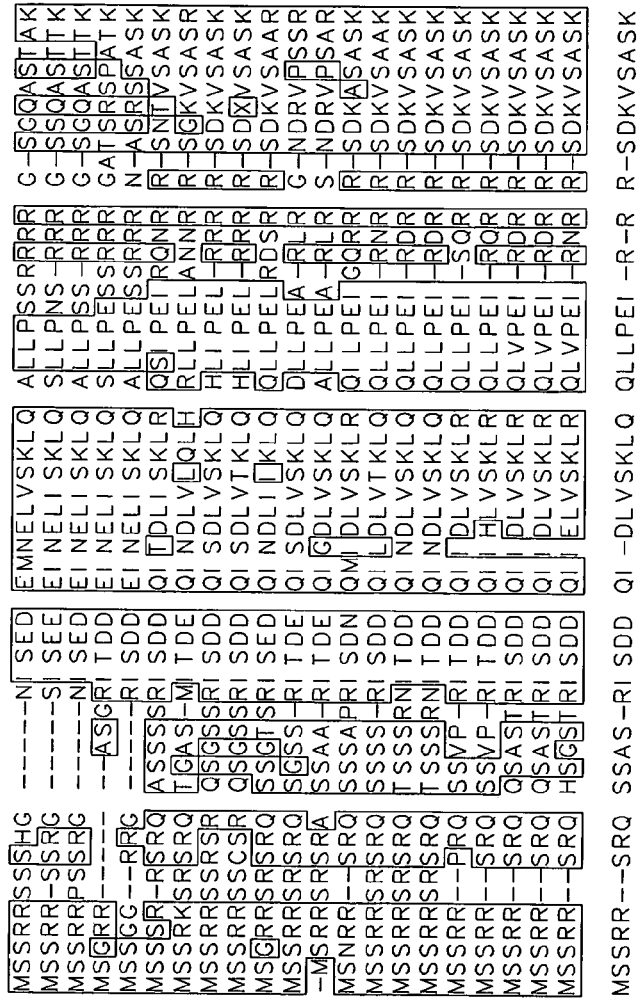
FIG. 1. Amino acid sequence alignment of homologues of Leads 80, 81, 113, 114, ME08328, ME01905, ME01770, ME20023 (Clone 18200) and ME21445, SEQ ID NOS. 95, 97, 91, 83, 89, 85, 87, 93, 81. Conserved regions are enclosed in a box. A consensus sequence is shown below the alignment. The sequences shown in FIG. 1 correspond to the following SEQ ID NOs.:
CeresClone: 486120—SEQ ID NO. 111
gi|50912765—SEQ ID NO. 110
CeresClone: 503296—SEQ ID NO. 112
gi|31431968 SEQ ID NO. 109
CeresClone: 336524—SEQ ID NO. 83
CeresClone: 8607—SEQ ID NO. 97 gi|22331645—SEQ ID NO. 106
CeresClone: 18200—SEQ ID NO. 81
CeresClone: 945972—SEQ ID NO. 103
CeresClone: 519—SEQ ID NO. 87
Lead•clone733804•Taxonomy•4565—SEQ ID NO. 95
gi|78708592—SEQ ID NO. 98
CeresClone: 4734—SEQ ID NO. 85
CeresGdna: 1468218—SEQ ID NO. 101
CeresClone: 653656—SEQ ID NO. 93
CeresClone: 663844—SEQ ID NO. 99
CeresGdna: 1530225—SEQ ID NO. 105
CeresGdna: 1449794—SEQ ID NO. 108
CeresClone: 703180—SEQ ID NO. 102
CeresClone: 560681—SEQ ID NO. 89
CeresClone: 560948—SEQ ID NO. 91

The invention of the present application may be described by, but not necessarily limited to, the following exemplary embodiments.

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

More particularly, the nucleic acid molecules of the present invention comprise: (a) a nucleotide sequence encoding an amino acid sequence that is at least 85% identical to any one of Leads 80, 81, 113, 114, ME08328, ME01905, ME01770, ME21445 and ME20023, corresponding to SEQ ID Nos. 94, 96, 90, 82, 88, 84, 86, 92, 80, respectively, (b) a nucleotide sequence that is complementary to any one of the nucleotide sequences according to (a), (c) a nucleotide sequence according to any one of SEQ ID Nos. 94, 96, 90, 82, 88, 84, 86, 92, 80, (d) a nucleotide sequence that is in reverse order of any one of the nucleotide sequences according to (c) when read in the 5' to 3' direction, (e) a nucleotide sequence able to interfere with any one of the nucleotide sequences according to (a), (f) a nucleotide sequence able to form a hybridized nucleic acid duplex with the nucleic acid according to any one of paragraphs (a)-(e) at a temperature from about 40° C. to about 48° C. below a melting temperature of the hybridized nucleic acid duplex, and (g) a nucleotide sequence encoding any one of amino acid sequences of Leads 80, 81, 113, 114, ME08328, ME01905, ME01770, ME21445 and ME20023, corresponding to SEQ ID NOS. 95, 97, 91, 83, 89, 85, 87, 93, 81, respectively.

Additional embodiments of the present invention include those polypeptide and nucleic acid molecule sequences disclosed in SEQ ID NOS. 94, 95, 96, 97, 90, 91, 82, 83, 88, 89, 84, 85, 86, 87, 92, 93, 80, 81.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of Leads 80, 81, 113, 114, ME08328, ME01905, ME01770, ME21445 and ME20023, corresponding to SEQ ID NOS. 95, 97, 91, 83, 89, 85, 87, 93, 81, respectively.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention, may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has increased size (in whole or in part), increased vegetative growth, increased organ number and/or increased biomass (sometimes hereinafter collectively referred to as increased biomass), lethality, sterility or ornamental characteristics as compared to a wild-type plant cultivated under identical conditions. Furthermore, the transgenic plant may comprise a first isolated nucleic acid molecule of the present invention, which encodes a protein involved in modulating growth and phenotype characteristics, and a second isolated nucleic acid molecule which encodes a promoter capable of driving expression in plants, wherein the growth and phenotype modulating component and the promoter are operably linked. More preferably, the first isolated nucleic acid may be mis-expressed in the transgenic plant of the present invention, and the transgenic plant exhibits modulated characteristics as compared to a progenitor plant devoid of the polynucleotide, when the transgenic plant and the progenitor plant are cultivated under identical environmental conditions. In another embodiment of the present invention the modulated growth and phenotype characteristics may be due to the inactivation of a particular sequence, using for example an interfering RNA.

A further embodiment consists of a plant, plant cell, plant material or seed of a plant according to the present invention which comprises an isolated nucleic acid molecule of the present invention, wherein the plant, or plants derived from the plant, plant cell, plant material or seed of a plant, has the modulated growth and phenotype characteristics as compared to a wild-type plant cultivated under identical conditions.

The polynucleotide conferring increased biomass or vigor may be mis-expressed in the transgenic plant of the present invention, and the transgenic plant exhibits an increased biomass or vigor as compared to a progenitor plant devoid of the polynucleotide, when the transgenic plant and the progenitor plant are cultivated under identical environmental conditions. In another embodiment of the present invention increased biomass or vigor phenotype may be due to the inactivation of a particular sequence, using for example an interfering RNA.

Another embodiment consists of a plant, plant cell, plant material or seed of a plant according to the present invention which comprises an isolated nucleic acid molecule of the present invention, wherein the plant, or plants derived from the plant, plant cell, plant material or seed of a plant, has increased biomass or vigor as compared to a wild-type plant cultivated under identical conditions.

Another embodiment of the present invention includes methods of enhancing biomass or vigor in plants. More particularly, these methods comprise transforming a plant with an isolated nucleic acid molecule according to the present invention. Preferably, the method is a method of enhancing biomass or vigor in the transformed plant, whereby the plant is transformed with a nucleic acid molecule encoding the polypeptide of the present invention.

Polypeptides of the present invention include consensus sequences. The consensus sequence is shown in FIG. 1.

2. Definitions

The following terms are utilized throughout this application:

Biomass: As used herein, "biomass" refers to useful biological material including a product of interest, which material is to be collected and is intended for further processing to isolate or concentrate the product of interest. "Biomass" may comprise the fruit or parts of it or seeds, leaves, or stems or roots where these are the parts of the plant that are of particular interest for the industrial purpose. "Biomass", as it refers to plant material, includes any structure or structures of a plant that contain or represent the product of interest.

Transformation: Examples of means by which this can be accomplished are described below and include *Agrobacterium*-mediated transformation (of dicots (Needleman and Wunsch (1970) *J. Mol. Biol.* 48:443; Pearson and Lipman (1988) *Proc. Natl. Acad. Sci.* (*USA*) 85: 2444), of monocots (Yamauchi et al. (1996) *Plant Mol. Biol.* 30:321-9; Xu et al. (1995) *Plant Mol. Biol.* 27:237; Yamamoto et al. (1991) *Plant Cell* 3:371), and biolistic methods (P. Tijessen, "Hybridization with Nucleic Acid Probes" In Laboratory Techniques in Biochemistry and Molecular Biology, P. C. vand der Vliet, ed., c. 1993 by Elsevier, Amsterdam), electroporation, in planta techniques, and the like. Such a plant containing an exogenous nucleic acid is referred to here as a $T_0$ for the primary transgenic plant and $T_1$ for the first generation.

Functionally Comparable Proteins or Functional Homologs: This term describes those proteins that have at least one functional characteristic in common. Such characteristics include sequence similarity, biochemical activity, transcriptional pattern similarity and phenotypic activity. Typically, the functionally comparable proteins share some sequence similarity or at least one biochemical. Within this definition, analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene or coding region from a different plant species or from a non-plant organism.

Percentage of sequence identity: As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).a1///////// The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

ClustalW calculates the best match between a query and one or more subject sequences, and aligns them so that identities, similarities and differences can be determined. Gaps of one or more residues can be inserted into a query sequence, a subject sequence, or both, to maximize sequence alignments.

For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web.

In case of the functional homolog searches, to ensure a subject sequence having the same function as the query sequence, the alignment has to be along at least 80% of the length of the query sequence so that the majority of the query sequence is covered by the subject sequence. To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Seedling vigor: As used herein, "seedling vigor" refers to the plant characteristic whereby the plant emerges from soil faster, has an increased germination rate (i.e., germinates faster), has faster and larger seedling growth and/or germinates faster under cold conditions as compared to the wild type or control under similar conditions. Seedling vigor has often been defined to comprise the seed properties that determine "the potential for rapid, uniform emergence and development of normal seedlings under a wide range of field conditions".

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter $T_m$, which is the temperature at which 50% of the complementary nucleic acid molecules in the hybridization assay are hybridized, in terms of a temperature differential from $T_m$. High stringency conditions are those providing a condition of $T_m$—5° C. to $T_m$—10° C. Medium or moderate stringency conditions are those providing $T_m$—20° C. to $T_m$—29° C. Low stringency conditions are those providing a condition of $T_m$—40° C. to $T_m$—48° C. The relationship between hybridization conditions and $T_m$ (in ° C.) is expressed in the mathematical equation:

$$T_m = 81.5 - 16.6(\log_{10}[\text{Na}^+]) + 0.41(\% \ G+C) - (600/N) \quad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m = 81.5 + 16.6 \log\{[\text{Na}^+]/(1+0.7[\text{Na}^+])\} + 0.41(\% \ G+C) - 500/L - 0.63(\% \ \text{formamide}) \quad (II)$$

where L represents the number of nucleotides in the probe in the hybrid (21). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (Frischauf et al. (1983) *J. Mol Biol*, 170: 827-842), stringency conditions can be adjusted to favor detection of identical genes or related family members.

Equation II is derived assuming the reaction is at equilibrium. Therefore, hybridizations according to the present invention are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$ medium or moderate stringency is 26-29° C. below $T_m$ and low stringency is 45-48° C. below $T_m$.

$T_0$: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

3. Important Characteristics of the Polynuceotides and Polypeptides of the Invention The nucleic acid molecules and polypeptides of the present invention are of interest because when the nucleic acid molecules are mis-expressed (i.e., when expressed at a non-natural location or in an increased or decreased amount relative to wild-type) they produce plants that exhibit modulated biomass, growth rate, or seedling vigor as compared to wild-type plants, as evidenced by the results of various experiments disclosed below. This trait can be used to exploit or maximize plant products. For example, the nucleic acid molecules and polypeptides of the present invention are used to increase the expression of genes that cause the plant to have modulated biomass, growth rate or seedling vigor.

Because the disclosed sequences and methods increase vegetative growth, and growth rate, the disclosed methods can be used to enhance biomass production. For example, plants that grow vegetatively have an increase biomass production, compared to a plant of the same species that is not genetically modified for substantial vegetative growth. Examples of increases in biomass production include increases of at least 5%, at least 20%, or even at least 50%, when compared to an amount of biomass production by a plant of the same species not growing vegetatively.

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase where the floral organs are produced. If the appropriate environmental and developmental signals the plant switches to floral, or reproductive, growth are disrupted, the plant will not be able to enter reproductive growth, therefore maintaining vegetative growth.

Seed or seedling vigor is an important characteristic that can greatly influence successful growth of a plant, such as crop plants. Adverse environmental conditions, such as dry, wet, cold or hot conditions, can affect a plant growth cycle, and the vigor of seeds (i.e. vitality and strength under such conditions can differentiate between successful and failed crop growth). Seedling vigor has often been defined to comprise the seed properties that determine "the potential for rapid, uniform emergence and development of normal seedlings under a wide range of field conditions". Hence, it would be advantageous to develop plant seeds with increased vigor.

For example, increased seedling vigor would be advantageous for cereal plants such as rice, maize, wheat, etc. production. For these crops, growth can often be slowed or stopped by cool environmental temperatures during the planting season. In addition, rapid emergence and tillering of rice would permit growers to initiate earlier flood irrigation which can save water and suppress weak growth. Genes associated with increased seed vigor and/or cold tolerance in rice, have therefore been sought for producing improve rice varieties. See e.g., Pinson, S., "Molecular Mapping of Seedling Vigor QTLs in Tropical Rice", USDA Agricultural Research Service, Dec. 16, 2000.

Seedling vigor has been measured by different tests and assays, including most typically a cold tolerance test and an accelerated aging test.

Some of the nucleotide sequences of the invention code for basic-helix-loop (bHCH) transcription factors. It is known that transcription factors often control the expression of multiple genes in a pathway. The basic/helix-loop-helix (BHLH) proteins are a superfamily of transcription factors that bind as dimers to specific DNA target sites. The bHLH transcription factors have been well characterized in nonplant eukaryotes and have been identified as important regulatory components in diverse biological processes. Many different functions have been identified for those proteins in animals, including the control of cell proliferation and transcription often involves homo- or hetero-dimerization. Members of the RIB basic helix-loop-helix (bHLH) family of plant transcription factors are involved in a variety of growth and differentiation processes.

A basic-helix-loop-helix (bHLH) is a protein structural motif that characterizes a family of transcription factors. The motif is characterized by two α helices connected by a loop. Transcription factors of this type are typically dimeric, each with one helix containing basic amino acid residues that facilitate DNA binding. One helix is typically smaller and due to the flexibility of the loop allows dimerization by folding and packing against another helix. The larger helix typically contains the DNA binding regions. bHLH proteins typically bind to a consensus sequence called an E-box, CANNTG. The canonical E-box is CACGTG, however some bHLH transcription factors bind to different sequences, which are often similar to the E-box. bHLH transcription factors are often important in development or cell activity.

4. The Polypeptides/Polynucleotides of the Invention

The polynucleotides of the present invention and the proteins expressed via translation of these polynucleotides are set forth in the Sequence Listing, specifically SEQ ID NOS. 94, 95, 96, 97, 90, 91, 82, 83, 88, 89, 84, 85, 86, 87, 92, 93, 80, 81. The Sequence Listing also consists of functionally comparable proteins Polypeptides comprised of a sequence within and defined by one of the consensus sequences can be utilized for the purposes of the invention, namely to make transgenic plants with modulated biomass, growth rate and/or seedling vigor.

5. Use of the Polypeptides to make Transgenic Plants

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, Sambrook et al., Molecular Cloning: A Laboratory Manual, Second Edition, Cold Spring Harbor Laboratory Press, 1989, New York.) and can be introduced into the plant species of interest by, for example, *Agrobacterium*-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lambda phage vectors, T-DNA fusion vectors and plasmid vectors (see, Shizuya et al. (1992) *Proc. Natl. Acad. Sci. USA,* 89: 8794-8797; Hamilton et al. (1996) *Proc. Natl. Acad. Sci. USA,* 93: 9975-9979; Burke et al. (1987) *Science,* 236:806-812; Sternberg N. et al. (1990) *Proc Natl Acad Sci USA.,* 87:103-7; Bradshaw et al. (1995) *Nucl Acids Res,* 23: 4850-4856; Frischauf et al. (1983) *J. Mol Biol,* 170: 827-842; Huynh et al., Glover N M (ed) DNA Cloning: A practical Approach, Vol. 1 Oxford: IRL Press (1985); Walden et al. (1990) *Mol Cell Biol* 1: 175-194).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorosulfuron or phosphinotricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To "operably link" a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (-212 to -154) from the upstream region of the octopine synthase (ocs) gene. Fromm et al., *The Plant Cell* 1:977-984 (1989).

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to said sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., *Plant Cell*, 1:855-866 (1989); Bustos, et al., *Plant Cell*, 1:839-854 (1989); Green, et al., *EMBO J.* 7, 4035-4044 (1988); Meier, et al., *Plant Cell*, 3, 309-316 (1991); and Zhang, et al., *Plant Physiology* 110: 1069-1079 (1996).

Examples of various classes of promoters are described below. Some of the promoters indicated below are described in more detail in U.S. Patent Application Ser. Nos. 60/505,689; 60/518,075; 60/544,771; 60/558,869; 60/583,691; 60/619,181; 60/637,140; 10/950,321; 10/957,569; 11/058,689; 11/172,703; 11/208,308; and PCT/US05/23639. It will be appreciated that a promoter may meet criteria for one classification based on its activity in one plant species, and yet meet criteria for a different classification based on its activity in another plant species.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

Various promoters can be used to drive expression of the polynucleotides of the present invention. Nucleotide sequences of such promoters are set forth in SEQ ID NOS: 1-79. Some of them can be broadly expressing promoters, others may be more tissue preferential.

A promoter can be said to be "broadly expressing" when it promotes transcription in many, but not necessarily all, plant tissues or plant cells. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO: 76), YP0144 (SEQ ID NO: 55), YP0190 (SEQ ID NO: 59), p13879 (SEQ ID NO: 75), YP0050 (SEQ ID NO: 35), p32449 (SEQ ID NO: 77), 21876 (SEQ ID NO: 1), YP0158 (SEQ ID NO: 57), YP0214 (SEQ ID NO: 61), YP0380 (SEQ ID NO: 70), PT0848 (SEQ ID NO: 26), and PT0633 (SEQ ID NO: 7). Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters drive transcription in root tissue, e.g., root endodermis, root epidermis, or root vascular tissues. In some embodiments, root-active promoters are root-preferential promoters, i.e., drive transcription only or predominantly in root tissue. Root-preferential promoters include the YP0128 (SEQ ID NO: 52), YP0275 (SEQ ID NO: 63), PT0625 (SEQ ID NO: 6), PT0660 (SEQ ID NO: 9), PT0683 (SEQ ID NO: 14), and PT0758 (SEQ ID NO: 22). Other root-preferential promoters include the PT0613 (SEQ ID NO: 5), PT0672 (SEQ ID NO: 11), PT0688 (SEQ ID NO: 15), and PT0837 (SEQ ID NO: 24), which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA* 86:7890-7894 (1989)), root cell specific promoters reported by Conkling et al., *Plant Physiol.* 93:1203-1211 (1990), and the tobacco RD2 gene promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al. (1989) *Plant Cell* 1(9):839-853), the soybean trypsin inhibitor promoter (Riggs et al. (1989) *Plant Cell* 1(6):609-621), the ACP promoter (Baerson et al. (1993) *Plant Mol Biol*, 22(2):255-267), the stearoyl-ACP desaturase gene (Slocombe et al. (1994) *Plant Physiol* 104(4):167-176), the soybean α' subunit of β-conglycinin promoter (Chen et al. (1986) *Proc Natl Acad Sci USA* 83:8560-8564), the oleosin promoter (Hong et al. (1997) *Plant Mol Biol* 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.* 13:5829-5842), the beta-amylase gene promoter, and the barley hordein gene promoter. Other maturing endosperm promoters include the YP0092 (SEQ ID NO: 38), PT0676 (SEQ ID NO: 12), and PT0708 (SEQ ID NO: 17.

Promoters that drive transcription in ovary tissues such as the ovule wall and mesocarp can also be useful, e.g., a polygalacturonidase promoter, the banana TRX promoter, and the melon actin promoter. Other such promoters that drive gene expression preferentially in ovules are YP0007 (SEQ ID NO: 30), YP011 (SEQ ID NO: 46), YP0092 (SEQ ID NO: 38), YP0103 (SEQ ID NO: 43), YP0028 (SEQ ID NO: 33), YP0121 (SEQ ID NO: 51), YP0008 (SEQ ID NO: 31), YP0039 (SEQ ID NO: 34), YP0115 (SEQ ID NO: 47), YP0119 (SEQ ID NO: 49), YP0120 (SEQ ID NO: 50) and YP0374 (SEQ ID NO: 68).

In some other embodiments of the present invention, embryo sac/early endosperm promoters can be used in order drive transcription of the sequence of interest in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142:1009-1020); maize Cat3 (see, GenBank No. L05934; Abler (1993) *Plant Mol. Biol.*, 22:10131-1038). Other promoters include the following *Arabidopsis* promoters: YP0039 (SEQ ID NO: 34), YP0101 (SEQ ID NO: 41), YP0102 (SEQ ID NO: 42), YP0110 (SEQ ID NO: 45), YP0117 (SEQ ID NO: 48), YP0119 (SEQ ID NO: 49), YP0137 (SEQ ID NO: 53), DME, YP0285 (SEQ ID NO: 64), and YP0212 (SEQ ID NO: 60).

Other promoters that may be useful include the following rice promoters: p530c10, pOsFIE2-2, pOsMEA, pOsYp102, and pOsYp285.

Promoters that preferentially drive transcription in zygotic cells following fertilization can provide embryo-preferential expression and may be useful for the present invention. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654, YP0097 (SEQ ID NO: 40), YP0107 (SEQ ID NO: 44), YP0088 (SEQ ID NO: 37), YP0143 (SEQ ID NO: 54), YP0156 (SEQ ID NO: 56), PT0650 (SEQ ID NO: 8), PT0695 (SEQ ID NO: 16), PT0723 (SEQ ID NO: 19), PT0838 (SEQ ID NO: 25), PT0879 (SEQ ID NO: 28) and PT0740 (SEQ ID NO: 20).

Promoters active in photosynthetic tissue in order to drive transcription in green tissues such as leaves and stems are of particular interest for the present invention. Most suitable are promoters that drive expression only or predominantly such tissues. Examples of such promoters include the ribulose-1, 5-bisphosphate carboxylase (RbcS) promoters such as the RbcS promoter from eastern larch (*Larix laricina*), the pine cab6 promoter (Yamamoto et al. (1994) *Plant Cell Physiol.* 35:773-778), the Cab-1 gene promoter from wheat (Fejes et al. (1990) *Plant Mol. Biol.* 15:921-932), the CAB-1 promoter from spinach (Lubberstedt et al. (1994) *Plant Physiol.* 104: 997-1006), the cab1R promoter from rice (Luan et al. (1992) *Plant Cell* 4:971-981), the pyruvate orthophosphate dikinase (PPDK) promoter from corn (Matsuoka et al. (1993) *Proc Natl Acad. Sci USA* 90:9586-9590), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. (1995) *Planta* 196:564-570), and thylakoid membrane protein promoters from spinach (psad, psaF, psae, PC, FNR, atpC, atpD, cab, rbcS. Other promoters that drive transcription in stems, leafs and green tissue are PT0535 (SEQ ID NO: 3), PT0668 (SEQ ID NO: 2), PT0886 (SEQ ID NO: 29), PR0924 (SEQ ID NO: 78), YP0144 (SEQ ID NO: 55), YP0380 (SEQ ID NO: 70) and PT0585 (SEQ ID NO: 4).

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. Examples of drought inedible promoters are YP0380 (SEQ ID NO: 70), PT0848 (SEQ ID NO: 26), YP0381 (SEQ ID NO: 71), YP0337 (SEQ ID NO: 66), YP0337 (SEQ ID NO: 66), PT0633 (SEQ ID NO: 7), YP0374 (SEQ ID NO: 68), PT0710 (SEQ ID NO: 18), YP0356 (SEQ ID NO: 67), YP0385 (SEQ ID NO: 73), YP0396 (SEQ ID NO: 74), YP0384 (SEQ ID NO: 72), YP0384 (SEQ ID NO: 72), PT0688 (SEQ ID NO: 15), YP0286 (SEQ ID NO: 65), YP0377 (SEQ ID NO: 69), and PD1367 (SEQ ID NO: 79). Examples of promoters induced by nitrogen are PT0863 (SEQ ID NO: 27), PT0829 (SEQ ID NO: 23), PT0665 (SEQ ID NO: 10) and PT0886 (SEQ ID NO: 29). An example of a shade inducible promoter is PR0924 (SEQ ID NO: 78).

Other Promoters: Other classes of promoters include, but are not limited to, leaf-preferential, stem/shoot-preferential, callus-preferential, guard cell-preferential, such as PT0678 (SEQ ID NO: 13), and senescence-preferential promoters. Promoters designated YP0086 (SEQ ID NO: 36), YP0188 (SEQ ID NO: 58), YP0263 (SEQ ID NO: 62), PT0758 (SEQ ID NO: 22), PT0743 (SEQ ID NO: 21), PT0829 (SEQ ID NO: 23), YP0119 (SEQ ID NO: 49), and YP0096 (SEQ ID NO: 39), as described in the above-referenced patent applications, may also be useful.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

Another alternative consists in inhibiting expression of a biomass or vigor-modulating polypeptide in a plant species of interest. The term "expression" refers to the process of converting genetic information encoded in a polynucleotide into RNA through transcription of the polynucleotide (i.e., via the enzymatic action of an RNA polymerase), and into protein, through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a biomass-modulating polypeptide. A nucleic acid that decreases the level of a transcription or translation product of a gene encoding a biomass-modulating polypeptide is transcribed into an antisense nucleic acid similar or identical to the sense coding sequence of the biomass- or growth rate-modulating polypeptide. Alternatively, the transcription product of an isolated nucleic acid can be similar or identical to the sense coding sequence of a biomass growth rate-modulating polypeptide, but is an RNA that is unpolyadenylated, lacks a 5' cap structure, or contains an unsplicable intron.

In another method, a nucleic acid can be transcribed into a ribozylne, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the biomass-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., 1996, *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

Transformation

Nucleic acid molecules of the present invention may be introduced into the genome or the cell of the appropriate host plant by a variety of techniques. These techniques, able to transform a wide variety of higher plant species, are well known and described in the technical and scientific literature (see, e.g., Weising et al. (1988) *Ann. Rev. Genet.,* 22:421 and Christou (1995) *Euphytica,* 85:13-27).

A variety of techniques known in the art are available for the introduction of DNA into a plant host cell. These techniques include transformation of plant cells by injection (Newell (2000)), microinjection (Griesbach (1987) *Plant Sci.* 50:69-77), electroporation of DNA (Fromm et al. (1985) *Proc. Natl. Acad. Sci. USA* 82:5824), PEG (Paszkowski et al. (1984) *EMBO J.* 3:2717), use of biolistics (Klein et al. (1987) *Nature* 327:773), fusion of cells or protoplasts (Willmitzer, L. (1993) Transgenic Plants. In: Iotechnology, A Multi-Volume Comprehensive treatise (H. J. Rehm, G. Reed, A. Püler, P. Stadler, eds., Vol. 2, 627-659, VCH Weinheim-New York-Basel-Cambridge), and via T-DNA using *Agrobacterium tumefaciens* (*Crit. Rev. Plant. Sci.* 4:1-46; Fromm et al. (1990) *Biotechnology* 8:833-844) or *Agrobacterium rhizogenes* (Cho et al. (2000) *Planta* 210:195-204) or other bacterial hosts (Brootghaerts et al. (2005) *Nature* 433:629-633), for example.

In addition, a number of non-stable transformation methods that are well known to those skilled in the art may be desirable for the present invention. Such methods include, but are not limited to, transient expression (Lincoln et al. (1998) *Plant Mol. Biol. Rep.* 16:1-4) and viral transfection (Lacomme et al. (2001), "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

The nucleic acid molecules of the present invention may be used to confer the trait of an altered flowering time.

The nucleic acid molecules of the present invention encode appropriate proteins from any organism, but are preferably found in plants, fungi, bacteria or animals.

The methods according to the present invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belonging to the orders of the Magniolales, illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales, for example, are also suitable. Monocotyledonous plants belonging to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales also may be useful in embodiments of the present invention. Further examples include, but are not limited to, plants belonging to the class of the Gymnospermae are Pinales, Ginkgoales, Cycadales and Gnetales.

The methods of the present invention are preferably used in plants that are important or interesting for agriculture, horticulture, biomass for bioconversion and/or forestry. Non-limiting examples include, for instance, tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, *petunia*, guayule, cabbages, spinach, alfalfa, artichokes, sugarcane, mimosa, *Servicea lespedera*, corn, wheat, rice, rye, barley, sorghum and grasses such as switch grass, giant reed, Bermuda grass, Johnson grasses or turf grass, millet, hemp, bananas, poplars, eucalyptus trees and conifers. Of interest are plates grown for energy production, so called energy crops, such as broadleaf plants like alfalfa, hemp, Jerusalem artichoke and grasses such as sorgum, switchgrass, Johnson grass and the likes.

Homologues Encompassed by the Invention

It is known in the art that one or more amino acids in a sequence can be substituted with other amino acid(s), the charge and polarity of which are similar to that of the substituted amino acid, i.e. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of Leads 80, 81, 113, 114, ME08328, ME01905, ME01770, ME21445 and ME20023, SEQ ID NOS. 95, 97, 91, 83, 89, 85, 87, 93, and 81, respectively, due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleic Acid Molecules and Their Corresponding Nucleotide Sequences The nucleic acid molecules, and nucleotide sequences thereof, of the present invention were identified by use of a variety of screens that are predictive of nucleotide sequences that provide plants with altered size, vegetative growth, growth rate, organ number, plant architecture and/or biomass. One or more of the following screens were, therefore, utilized to identify the nucleotide (and amino acid) sequences of the present invention.

The present invention is further exemplified by the following examples. The examples are not intended to in any way limit the scope of the present application and its uses.

6. Experiments Confirming the Usefulness of the Polynucleotides and Polypeptides of the Invention General Protocols

*Agrobacterium*-Mediated Transformation of *Arabidopsis*

Wild-type *Arabidopsis thaliana* Wassilewskija (WS) plants are transformed with Ti plasmids containing clones in the sense orientation relative to the 35S promoter. A Ti plasmid vector useful for these constructs, CRS 338, contains the Ceres-constructed, plant selectable marker gene phosphinothricin acetyltransferase (PAT), which confers herbicide resistance to transformed plants.

Ten independently transformed events are typically selected and evaluated for their qualitative phenotype in the $T_1$ generation.

Preparation of Soil Mixture: 24 L SunshineMix #5 soil (Sun Gro Horticulture, Ltd., Bellevue, Wash.) is mixed with 16 L Therm-O-Rock vermiculite (Therm-O-Rock West, Inc., Chandler, Ariz.) in a cement mixer to make a 60:40 soil mixture. To the soil mixture is added 2 Tbsp Marathon 1% granules (Hummert, Earth City, Mo.), 3 Tbsp OSMOCOTE® 14-14-14 (Hummert, Earth City, Mo.) and 1 Tbsp Peters fertilizer 20-20-20 (J.R. Peters, Inc., Allentown, Pa.), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 µl 2 mg/ml benzylaminopurine to 900 ml water.

Dipping Infiltration: The pots are inverted and submerged for 5 minutes so that the aerial portion of the plant is in the *Agrobacterium* suspension. Plants are allowed to grow normally and seed is collected.

High-throughput Phenotypic Screening of Misexpression Mutants: Seed is evenly dispersed into water-saturated soil in pots and placed into a dark 4° C. cooler for two nights to promote uniform germination. Pots are then removed from the cooler and covered with 55% shade cloth for 4-5 days. Cotyledons are fully expanded at this stage. FINALE® (Sanofi Aventis, Paris, France) is sprayed on plants (3 ml FINALE® diluted into 48 oz. water) and repeated every 3-4 days until only transformants remain. Screening: Screening is routinely performed at four stages: Seedling, Rosette, Flowering, and Senescence.

Seedling—the time after the cotyledons have emerged, but before the $3^{rd}$ true leaf begins to form.

Rosette—the time from the emergence of the $3^{rd}$ true leaf through just before the primary bolt begins to elongate.

Flowering—the time from the emergence of the primary bolt to the onset of senescence (with the exception of noting the flowering time itself, most observations should be made at the stage where approximately 50% of the flowers have opened).

Senescence—the time following the onset of senescence (with the exception of "delayed senescence", most observations should be made after the plant has completely dried). Seeds are then collected.

Screens: Screening for increased size, vegetative growth and/or biomass is performed by taking measurements, specifically $T_2$ measurements were taken as follows:

Days to Bolt=number of days between sowing of seed and emergence of first inflorescence.

Rosette Leaf Number at Bolt=number of rosette leaves present at time of emergence of first inflorescence.

Rosette Area=area of rosette at time of initial inflorescence emergence, using formula ((L×W)*3.14)/4.

Height=length of longest inflorescence from base to apex. This measurement was taken at the termination of flowering/onset of senescence.

Primary Inflorescence Thickness=diameter of primary inflorescence 2.5 cm up from base. This measurement was taken at the termination of flowering/onset of senescence.

Inflorescence Number=total number of unique inflorescences. This measurement was taken at the termination of flowering/onset of senescence.

PCR was used to amplify the cDNA insert in one randomly chosen $T_2$ plant. This PCR product was then sequenced to confirm the sequence in the plants.

Screening Superpools For Tolerance To Low Ammonium Nitrate Growth Conditions:

Superpools are generated and two thousand seeds each from ten superpools are pooled together and assayed using the Low Ammonium Nitrate Screen on Agar. Low ammonium nitrate growth media, pH 5.7, is as follows: 0.5×MS without N (PhytoTech), 0.5% sucrose (Sigma), 240 µM $NH_4NO_3$ (EM Science), 0.5 g MES hydrate (Sigma), 0.8% Phytagar (EM Science). Forty-five (45) ml of media per square plate is used.

*Arabidopsis thaliana* cv WS seed is sterilized in 50% Clorox™ with 0.01% Triton X-100 (v/v) for five minutes, washed four times with sterile distilled deionized water and stored at 4° C. in the dark for 3 days prior to use.

Seed is plated at a density of 100 seeds per plate. Wild-type seed is used as a control. Plates are incubated in a Conviron™ growth chamber at 22° C. with a 16:8 hour light:dark cycle from a combination of incandescent and fluorescent lamps emitting a light intensity of ~100 μEinsteins and 70% humidity.

Seedlings are screened daily after 14 days. Candidate seedlings are larger or stay greener longer relative to wild-type controls. DNA is isolated from each candidate plant and sequenced to determine which transgene was present.

Seedling Low Ammonium Nitrate Assay On Agar:

Media and seeds are prepared as described above.

Seeds from five misexpression line events, each containing the same polynucleotide, are sown in two rows, with ten seeds per row. Each plate contains five events, for a total of 100 seeds. Control plates containing wild-type seed are also prepared. Plates are then incubated at 4° C. for at least two days.

After the several day 4° C. cold treatment, plates are incubated in a Conviron™ growth chamber at 22° C. with a 16:8 hour light: dark cycle from a combination of incandescent and fluorescent lamps emitting a light intensity of ~100 μEinsteins and 70% humidity.

After 14 days, plates are scanned daily using a CF Imager (Technologica Ltd.) with a 45 minute dark acclimation. The CF Imager is used to quantify the seedlings' optimum quantum yields (Fv/Fm) as a measure of photosynthetic health (see details below). To quantify the seedlings' sizes, plates are also scanned with a flatbed photo scanner (Epson) one day after nitrogen stress is apparent and wild-type seedling growth is arrested. Image capture is ended after all wild-type plants have completely yellowed. On the final scanning day plates are uncovered and liberally sprayed with Finale™ (10 ml in 48 oz. Murashige & Skoog liquid media) and returned to the growth chamber.

Two days after spraying, the plates are placed in a closed box for 45 minutes to acclimate in preparation for fluorescence visualization via CF Imager. Plants resistant to Finale™ appear red while sensitive plants appear blue. After image capture, plants are assigned a transgenic (resistant) or non-transgenic (sensitive) status. The non-transgenic plants (i.e. non-transgenic segregants) serve as internal controls.

Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under nitrogen stress conditions. Since a large amount of nitrogen is invested in maintaining the photosynthetic apparatus, nitrogen deficiencies can lead to dismantling of the reaction centers and to reductions in photosynthetic efficiency. Consequently, from the start of image capture collection until the plants are dead the Fv/Fm ratio is determined for each seedling using the FluroImager 2 software (Kevin Oxborough and John Bartington).

The rosette area of each plant is also analyzed using Win-RHIZO software (Regent Instruments) to analyze the Epson flatbed scanner captured images.

Low Ammonium Nitrate Validated Assay:

Media and seeds are prepared as described above.

For misexpression lines which pass the above low ammonium nitrate assay, both $T_2$ and $T_3$ generation seed for an event are plated along with wild-type seed, at a final density of 100 seeds per plate. Plates contain 10 seed/row and have four rows of 10 $T_2$ seed followed by two rows of wild-type seed, followed by four rows of $T_3$ seed. Plates are then incubated at 4° C. for at least two days.

After the several day 4° C. cold treatment, plates are incubated in a Conviron™ growth chamber at 22° C. with a 16:8 hour light:dark cycle from a combination of incandescent and fluorescent lamps emitting a light intensity of ~100 μEinsteins and 70% humidity.

After 14 days, plates are scanned daily using a CF Imager (Technologica Ltd.) with a 45 minute dark acclimation. The CF Imager is used to quantify the seedlings' optimum quantum yields (Fv/Fm) as a measure of photosynthetic health. To quantify the seedlings' sizes, plates are also scanned with a flatbed photo scanner (Epson) one day after nitrogen stress is apparent and wild-type seedling growth is arrested. Image capture is ended after all wild-type plants have completely yellowed. On the final scanning day plates are uncovered and liberally sprayed with Finale™ (10 ml in 48 oz. Murashige & Skoog liquid media) and returned to the growth chamber.

Two days after spraying, the plates are placed in a closed box for 45 minutes to acclimate in preparation for fluorescence visualization via CF Imager. Plants resistant to Finale™ appear red while sensitive plants appear blue. After image capture, plants are assigned a transgenic (resistant) or non-transgenic (sensitive) status. The non-transgenic plants (i.e. non-transgenic segregants) serve as internal controls.

Fv/Fm ratio is determined for each seedling using the FluroImager 2 software (Kevin Oxborough and John Bartington).

The rosette area of each plant is also analyzed using Win-RHIZO software (Regent Instruments) to analyze the Epson flatbed scanner captured images.

Results:

Plants transformed with the genes of interest were screened as described above for modulated growth and phenotype characteristics. The observations include those with respect to the entire plant, as well as parts of the plant, such as the roots and leaves. The observations for transformants with each polynucleotide sequence are noted in the Sequence listing for each of the tested nucleotide sequences and the corresponding encoded polypeptide. The modulated characteristics (i.e. observed phenotypes) are noted by an entry in the "miscellaneous features" field for each respective sequence. The "Phenotype" noted in the Sequence Listing for each relevant sequence further includes a statement of the useful utility of that sequence based on the observations.

The observations made for the various transformants can be categorized, depending upon the relevant plant tissue for the observation and the consequent utility/usefulness of the nucleotide sequence/polypeptide used to make that transformant. Table 1 correlates the shorthand notes in the sequence listing to the observations noted for each tranformant (the "description" column), the tissue of the observation, the phenotype thereby associated with the transformant, and the consequent utility/usefulness of the inserted nucleotide sequence and encoded polypeptide (the "translation" column).

For some of the polynucleotides/polypeptides of the invention, the sequence listing further includes (in a "miscellaneous feature" section) an indication of important identified dominant(s) and the corresponding function of the domain or identified by comparison to the publicly available pfam database.

TABLE 1

| TISSUE | PHENOTYPE QUALIFIER | PHENOTYPE | DESCRIPTION | TRANSLATION |
|---|---|---|---|---|
| WHOLE PLANT | Senescence Time | Early Senescence | the plant senesces significantly early (note the approximate number of days early it started to senesce in the comments) | Useful for accelerating crop development and harvest |
| INFLORESCENCE | Flowering Time | Early Flowering | the plant flowers significantly early (note the approximate number of days early it flowered in the comments) | Useful for accelerating flowering time |
| INFLORESCENCE | Flowering Time | Late Flowering | the plant flowers significantly late (note the approximate number of days late it flowered in the comments) | Useful for delaying flowering time |
| INFLORESCENCE | Flowering Time | Dtb | days to bolt | Useful for delaying flowering time |
| WHOLE PLANT | Senescence Time | Late Senescence | the plant senesces significantly late (note the approximate number of days late it started to senesce in the comments) | Useful for delaying senescence |
| COTYLEDONS | Silver | Silver | cotyledons have a gray/silver colored surface; This phenotype is often accompanied by a small size mutation, but not always | Useful for drought or stress tolerance |
| WHOLE SEEDLING | Dark Green | Dark Green | plant is visibly darker green | Useful for increasing chlorophyll and photosynthetic capacity |
| WHOLE PLANT | Color | Dark Green | the plant is abnormally dark green | Useful for increasing chlorophyll and photosynthetic capacity |
| WHOLE SEEDLING | High Anthocyanin | High Anthocyanin | the plant is purple in color | Useful for increasing increasing anthocyanin content |
| WHOLE PLANT | Color | High Anthocyanin | the plant is purple in color | Useful for increasing increasing anthocyanin content |
| ROOT | No Growth in Soil | No Growth in Soil | roots grow along the soil surface instead of into the soil | Useful for increasing root growth eg to enhance nutrient uptake |
| ROOT | Other | Other | this correlates with any root mutant phenotypes which do not fit into the above categories (a picture should be taken for documentation) | Useful for increasing root growth eg to enhance nutrient uptake |
| LATERAL ROOTS | Number | Less Lateral Roots | there is an abnormally low number of lateral roots | Useful for increasing root growth eg to enhance nutrient uptake |
| LATERAL ROOTS | Other | Other | this correlates with any lateral root mutant phenotypes which do not fit into the above categories (a picture should be taken for documentation) | Useful for increasing root growth eg to enhance nutrient uptake |
| ROOT | Classic | Classic | there is a lack of lateral roots (buds may appear but do not elongate) | Useful for increasing root growth eg to enhance nutrient uptake |
| ROOT | Dwarf | Dwarf | there is a stunted root system | Useful for increasing root growth eg to enhance nutrient uptake |

TABLE 1-continued

| TISSUE | PHENOTYPE QUALIFIER | PHENOTYPE | DESCRIPTION | TRANSLATION |
|---|---|---|---|---|
| ROOT | Mid-Section | Mid-Section | there are lateral roots in the top and bottom quarters of the whole root, but none in the middle | Useful for increasing root growth eg to enhance nutrient uptake |
| ROOT | Split | Split | appears as "classic" but with two primary roots, both originating from the hypocotyl base | Useful for increasing root growth eg to enhance nutrient uptake |
| ROOT | Other | Other | this correlates with any overall root structure mutant phenotypes which do not fit into the above categories (a picture should be taken for documentation) | Useful for increasing root growth eg to enhance nutrient uptake |
| PRIMARY ROOT | Other | Other | this correlates with any primary root mutant phenotypes which do not fit into the above categories (a picture should be taken for documentation) | Useful for increasing root growth eg to enhance nutrient uptake |
| ROOT HAIRS | Length | Longer Root Hair | the root hairs are abnormally long | Useful for increasing root growth eg to enhance nutrient uptake |
| ROOT HAIRS | Length | Smaller Root Hair | the root hairs are abnormally short | Useful for increasing root growth eg to enhance nutrient uptake |
| ROOT HAIRS | Number | Less root hairs | there is an abnormally low number of root hairs | Useful for increasing root growth eg to enhance nutrient uptake |
| ROOT HAIRS | Other | Other | this correlates with any root hair mutant phenotypes which do not fit into the above categories (a picture should be taken for documentation) | Useful for increasing root growth eg to enhance nutrient uptake |
| ROOT HAIRS | Bulbous Root Hairs | Bulbous Root Hairs | Bulbous Root Hairs | Useful for increasing root growth eg to enhance nutrient uptake |
| ROOT | Bearded (Nitrogen) | Bearded (Nitrogen) | the lateral roots are long in high nitrogen, and they are short in low nitrogen | Useful for increasing root growth eg to enhance nutrient uptake |
| PRIMARY ROOT | Thickness | Thicker Primary Root | the primary root is abnormally thick | Useful for increasing root growth eg to enhance nutrient uptake |
| WHOLE PLANT | Stress | Root Architecture | Identify plants with increased root mass | Useful for increasing root growth eg to enhance nutrient uptake |
| PRIMARY ROOT | Thickness | Thinner Primary Root | the primary root is abnormally thin | Useful for increasing root growth eg to enhance nutrient uptake |
| PRIMARY ROOT | Wavy | Wavy | there is a consistent and gentle wavy appearance | Useful for increasing root growth eg to enhance nutrient uptake |
| LATERAL ROOTS | Length | Longer Lateral Root | the lateral roots are abnormally long | Useful for increasing root growth eg to enhance nutrient uptake |
| LATERAL ROOTS | Number | More Lateral Roots | there is an abnormally high number of lateral roots | Useful for increasing root growth eg to enhance nutrient uptake |
| ROOT HAIRS | Number | More root hairs | there is an abnormally high number of root hairs | Useful for increasing root growth eg to enhance nutrient uptake Useful for increasing seed carbon or nitrogen |
| SEED | Seed Weight | Weight | weight of seed | Useful for increasing seed weight |

TABLE 1-continued

| TISSUE | PHENOTYPE QUALIFIER | PHENOTYPE | DESCRIPTION | TRANSLATION |
| --- | --- | --- | --- | --- |
| SILIQUES | Length | Long | siliques are abnormally long (the percent difference in length compared to the control should be noted in the comments) | Useful for increasing seed/fruit yield or modifying fruit content |
| SILIQUES | Length | Short | siliques are abnormally short (the percent difference in length compared to the control should be noted in the comments) | Useful for increasing seed/fruit yield or modifying fruit content |
| SILIQUES | Other | Other | this correlates with any silique mutant phenotypes which do not fit into the above categories (a picture should be taken for documentation) | Useful for increasing seed/fruit yield or modifying fruit content |
| ROSETTE LEAVES | Size | Large | rosette leaves are abnormally large (the percent difference in size compared to the control should be noted in the comments) | Useful for increasing vegetative growth and enhancing foliage |
| | | | | Useful for making nutraceuticals/pharmaceuticals in plants |
| HYPOCOTYL | Other | Other | this correlates with any hypocotyl mutant phenotypes which do not fit into the above categories (a picture should be taken for documentation) | Useful for making larger plants |
| WHOLE SEEDLING | Other | Other | this correlates with any whole plant mutant phenotypes which do not fit into the above categories (a picture should be taken for documentation) | Useful for making larger plants |
| WHOLE PLANT | Other | Other | this correlates with any whole plant mutant phenotypes which do not fit into the above categories (a picture should be taken for documentation) | Useful for making larger plants |
| CAULINE LEAVES | Petiole Length | Long Petioles | the cauline petioles are abnormally long (the percent difference in size compared to the control should be noted in the comments) | Useful for making larger plants |
| WHOLE SEEDLING | Size | Large | plant is abnormally large (the percent difference in size compared to the control should be noted in the comments) | Useful for making larger plants |

TABLE 1-continued

| TISSUE | PHENOTYPE QUALIFIER | PHENOTYPE | DESCRIPTION | TRANSLATION |
|---|---|---|---|---|
| WHOLE PLANT | Size | Large | plant is abnormally large (the percent difference in size compared to the control should be noted in the comments) | Useful for making larger plants |
| SEED | Lethal | Lethal | the seed is inviable and appears as a small, dark, raisin-like seed in the mature siligue | Useful for making lethal plants for genetic confinement systems |
| WHOLE SEEDLING | Germination | No Germination | none of the seed germinates | Useful for making lethal plants for genetic confinement systems |
| WHOLE SEEDLING | Germination | Poor Germination | a portion of the seed never germinates | Useful for making lethal plants for genetic confinement systems |
| WHOLE SEEDLING | Germination | Slow Germination | a portion of the seed germinates significantly later than the rest of the seed in the pot | Useful for making lethal plants for genetic confinement systems |
| ROSETTE LEAVES | Vitrified | Vitrified | leaves are somewhat translucent or ?water soaked? | Useful for making lethal plants for genetic confinement systems |
| CAULINE LEAVES | Vitrified | Vitrified | leaves are somewhat translucent or ?water soaked? | Useful for making lethal plants for genetic confinement systems |
| COTYLEDONS | Albino | Opaque Albino | plant is opaque and devoid of pigment | Useful for making lethal plants for genetic confinement systems |
| COTYLEDONS | Albino | Translucent Albino | plant is translucent and devoid of pigment | Useful for making lethal plants for genetic confinement systems |
| WHOLE SEEDLING | Lethal | Seedling Lethal | cotyledons emerge (although they are often small), but then the plant ceases to develop further; No true leaves appear and the plant dies early (These differ from yellow-green lethals in that the cotyledons are wild-type in color and may not look differ | Useful for making lethal plants for genetic confinement systems |
| WHOLE SEEDLING | Lethal | Yellow-Green Lethal | cotyledons are small and pale yellow-green in color, but NOT totally devoid of pigment; In addition to yellow-green cotyledons, these plants produce no or severely reduced size true leaves, which, if present, are also yellow-green; These plants die prem | Useful for making lethal plants for genetic confinement systems |
| WHOLE SEEDLING | Meristem Mutant | Meristem Mutant | this term encompasses a variety of phenotypes, all of which have one thing in common, i.e., they all have something significantly wrong with how the meristem is producing its leaves; | Useful for making lethal plants for genetic confinement systems |

TABLE 1-continued

| TISSUE | PHENOTYPE QUALIFIER | PHENOTYPE | DESCRIPTION | TRANSLATION |
|---|---|---|---|---|
| WHOLE SEEDLING | Seedling Defective | Seedling Defective | Depending on the severity of the phenotype, the plants in this category this term encompasses a variety of phenotypes which share similar characteristics, i.e., they are small, have distorted structures, and are prone to early death; For example, patterning mutants would be a class of mutants which fall under this category | Useful for making lethal plants for genetic confinement systems |
| WHOLE PLANT | Color | Yellow-Green Viable 1 | the leaves and cotyledons are yellow-green in color, but this is not a lethal phenotype | Useful for making lethal plants for genetic confinement systems |
| WHOLE PLANT | Color | Yellow-Green Viable 2 | the leaves are yellow-green in color but the cotyledons are a wild-type green in color | Useful for making lethal plants for genetic confinement systems |
| WHOLE PLANT | Color | Yellow-Green Viable 3 | the leaves start out wild-type green and gradually turn yellow-green in color, while the cotyledons stay wild-type green | Useful for making lethal plants for genetic confinement systems |
| WHOLE PLANT | Color | Yellow-Green Viable 4 | the leaves appear wild-type green, but slowly turn yellow-green over time, while the cotyledons appear and remain yellow-green | Useful for making lethal plants for genetic confinement systems |
| WHOLE PLANT | Stress | Seed Bleaching | Identify plants whose seed coats do not bleach out under long bleach soaking | Useful for making low fiber seeds with increased digestability |
| ROSETTE LEAVES | Fused | Leaf Fused to Inflorescence | the leaf is fused to an inflorescence | Useful for making ornamental plants with flowers and leaves fused |
| ROSETTE LEAVES | Interveinal Chlorosis | Interveinal Chlorosis | the leaf tissue is chlorotic between its veins | Useful for making ornamental plants with modified color |
| CAULINE LEAVES | Interveinal Chlorosis | Interveinal Chlorosis | the leaf tissue is chlorotic between its veins | Useful for making ornamental plants with modified color |
| FLOWER | Organ Morphology | Fused Sepals | the sepals are fused together and won?t open naturally, but the flower is otherwise wild-type | Useful for making ornamental plants with modified flowers |
| FLOWER | Organ Morphology | Narrow Petals | the petals are abnormally narrow | Useful for making ornamental plants with modified flowers |
| FLOWER | Organ Morphology | Narrow Sepals | the sepals are abnormally narrow | Useful for making ornamental plants with modified flowers |
| FLOWER | Organ Morphology | Short Petals | the petals are abnormally short | Useful for making ornamental plants with modified flowers |
| FLOWER | Organ Morphology | Short Sepals | the sepals are abnormally short | Useful for making ornamental plants with modified flowers |

TABLE 1-continued

| TISSUE | PHENOTYPE QUALIFIER | PHENOTYPE | DESCRIPTION | TRANSLATION |
|---|---|---|---|---|
| FLOWER | Size | Large | flower is abnormally large (the percent difference in size compared to the control should be noted in the comments) | Useful for making ornamental plants with modified flowers |
| FLOWER | Size | Small | flower is abnormally small (the percent difference in size compared to the control should be noted in the comments) | Useful for making ornamental plants with modified flowers |
| FLOWER | Other | Other | this correlates with any flower mutant phenotypes which do not fit into the above categories (a picture should be taken for documentation) | Useful for making ornamental plants with modified flowers |
| INFLORESCENCE | Aerial Rosette | Aerial Fosette | rosette forms at or above the first internode | Useful for making ornamental plants with modified flowers |
| INFLORESCENCE | Appearance | Corkscrew Appearance | the inflorescence is really twisted, almost like a corkscrew, but somewhat more irregular | Useful for making ornamental plants with modified flowers |
| INFLORESCENCE | Appearance | Curved Appearance | the inflorescence has a slight, irregular curve upwards, greater than that of the control plants | Useful for making ornamental plants with modified flowers |
| INFLORESCENCE | Appearance | Multi-Inflorescence Fusion | the inflorescence is fused to another inflorescence, creating a celery-like appearance | Useful for making ornamental plants with modified flowers |
| INFLORESCENCE | Appearance | Undulate Appearance | the inflorescence is wavy in appearance | Useful for making ornamental plants with modified flowers |
| INFLORESCENCE | Branching | Acauline Branching | first branching is not subtended by a cauline leaf | Useful for making ornamental plants with modified flowers |
| INFLORESCENCE | Wax | Glaucous | inflorescence is abnormally dull in appearance | Useful for making ornamental plants with modified flowers |
| INFLORESCENCE | Wax | Glossy | inflorescence is shiny/glossy in appearance | Useful for making ornamental plants with modified flowers |
| INFLORESCENCE | Other | Other | this correlates with any inflorescence mutant phenotypes which do not fit into the above categories (a picture should be taken for documentation) | Useful for making ornamental plants with modified flowers |
| COTYLEDONS | Asymmetric | Asymmetric | the shape of the cotyledon is asymmetric in reference to the vertical axis | Useful for making ornamental plants with modified foliage |
| ROSETTE LEAVES | Other | Other | this correlates with any leaf mutant phenotypes which do not fit into the above categories (a picture should be taken for documentation) | Useful for making ornamental plants with modified leaves |

TABLE 1-continued

| TISSUE | PHENOTYPE QUALIFIER | PHENOTYPE | DESCRIPTION | TRANSLATION |
|---|---|---|---|---|
| CAULINE LEAVES | Other | Other | this correlates with any cauline mutant phenotypes which do not fit into the above categories (a picture should be taken for documentation) | Useful for making ornamental plants with modified leaves |
| FLOWER | Homeotic Mutant | Homeotic Mutant | the flower has one or more of its organs converted to another type of organ (specific details should be noted in the comments) | Useful for making plants sterile and for genetic confinement |
| FLOWER | Organ Morphology | Aberrant Organ Number | there is an abnormal number of some or all of the flowers organs | Useful for making plants sterile and for genetic confinement |
| FLOWER | Organ Morphology | Short Stamens | the stamens are abnormally short; This often leads to mechanical problems with fertility | Useful for making plants sterile and for genetic confinement |
| FLOWER | Fertility | Aborted fertility | the ovule is unfertilized and appears as a brown or white speck in the mature silique | Useful for making plants sterile and for genetic confinement |
| FLOWER | Fertility | Female-sterile | there is a problem with the ovules such that no fertilization is occurring | Useful for making plants sterile and for genetic confinement |
| FLOWER | Fertility | Male-sterile | there is a problem with the pollen such that no fertilization is occurring | Useful for making plants sterile and for genetic confinement |
| FLOWER | Fertility | Reduced fertility | a reduced number of successful fertilization events, and therefore seeds, are being produced by the plant | Useful for making plants sterile and for genetic confinement |
| FLOWER | Fertility | Sterile | no successful fertilization events, and therefore no seed is being produced by the plant; The reason for this sterility is not known at the time of the observation | Useful for making plants sterile and for genetic confinement |
| FLOWER | Fertility | Other | this correlates with any fertility mutant phenotypes which do not fit into the above categories (a picture should be taken for documentation) | Useful for making plants sterile and for genetic confinement |
| WHOLE PLANT | Stress | Early Flowering | Identify plants that flower early | Useful for making plants that flower early |
| COTYLEDONS | Petiole Length | Long Petioles | the cotyledon petioles are abnormally long (the percent difference in size compared to the control should be noted in the comments) | Useful for making plants that grow and better in shade |
| ROSETTE LEAVES | Petiole Length | Varying Petiole Lengths | the leaf petioles vary in length throughout the rosette | Useful for making plants that grow better in shade |

TABLE 1-continued

| TISSUE | PHENOTYPE QUALIFIER | PHENOTYPE | DESCRIPTION | TRANSLATION |
| --- | --- | --- | --- | --- |
| ROSETTE LEAVES | Petiole Length | Long Petioles | the leaf petioles are abnormally long (the percent difference in size compared to the control should be noted in the comments) | Useful for making plants that grow better in shade |
| WHOLE PLANT | Stress | | Identify plants able to tolerate high density and no phosphate and nitrogen, possible lead assay for vigor under population density and low nutrient conditions | Useful for making plants tolerant to biotic stress Useful for making plants tolerant to density and low fertilizer |
| WHOLE PLANT | Stress | pH (high) | Identify plants tolerant to high pH, and possibly low phosphate | Useful for making plants tolerant to high pH or low phosphate |
| WHOLE PLANT | Stress | Low Nitrate | Identify plants tolerant to low nitrogen/nitrate growth media | Useful for making plants tolerant to low nitrogen |
| WHOLE PLANT | Stress | LNABA | Identify plants tolerant to low nitrogen and high ABA concentrations | Useful for making plants tolerant to low nitrogen |
| WHOLE PLANT | Stress | No Nitrogen | Identify plants with increased vigor under no nitrogen conditions | Useful for making plants tolerant to low nitrogen |
| WHOLE PLANT | Stress | MSX | Identify plants tolerant to nitrogen assimilation inhibitor, and possibly low nitrogen tolerance and/or seed nitrogen accumulation | Useful for making plants tolerant to low nitrogen |
| WHOLE PLANT | Stress | No N, No PO4 | Identify plants tolerant to no nitrogen and no phosphate growth media | Useful for making plants tolerant to low nitrogen/low phosphate |
| WHOLE PLANT | Stress | Oxidative | Identify plants tolerant to oxidative stress | Useful for making plants tolerant to oxidative stresses |
| ROSETTE LEAVES | Trichomes | Few Trichomes | trichomes are sparse but present on the leaves | Useful for making plants with enhanced chemical composition |
| ROSETTE LEAVES | Trichomes | Glabrous | trichomes are totally absent | Useful for making plants with enhanced chemical composition |
| ROSETTE LEAVES | Trichomes | Abnormal Trichome Shape | the trichomes are abnormally shaped | Useful for making plants with enhanced chemical composition |
| CAULINE LEAVES | Trichomes | Few Trichomes | trichomes are sparse but present on the leaves | Useful for making plants with enhanced chemical composition |
| CAULINE LEAVES | Trichomes | Glabrous | trichomes are totally absent | Useful for making plants with enhanced chemical composition |
| CAULINE LEAVES | Trichomes | Abnormal Trichome Shape | the trichomes are abnormally shaped | Useful for making plants with enhanced chemical composition |
| INFLORESCENCE | Trichomes | Glabrous | trichomes are totally absent | Useful for making plants with enhanced chemical composition |
| INFLORESCENCE | Trichomes | Abnormal Trichome Shape | the trichomes are abnormally shaped | Useful for making plants with enhanced chemical composition |

TABLE 1-continued

| TISSUE | PHENOTYPE QUALIFIER | PHENOTYPE | DESCRIPTION | TRANSLATION |
|---|---|---|---|---|
| ROSETTE LEAVES | Curled | Corkscrew | leaves appear as "Curled 5", with the additional attribute of twisting like a corkscrew, instead of uniformly curling from both sides of the leaf | Useful for making plants with altered leaf shape eg curled leaves |
| ROSETTE LEAVES | Curled | Cup-shaped | leaves are curled up at the leaf margins such that they form a cup or bowl-like shape | Useful for making plants with altered leaf shape eg curled leaves |
| ROSETTE LEAVES | Curled | Curled 1 | leaves are abnormally curled slightly up or down at the leaf margins, but do not fall under the "cup-shaped" description (least severe type) | Useful for making plants with altered leaf shape eg curled leaves |
| ROSETTE LEAVES | Curled | Curled 2 | leaves are abnormally curled up or down at the leaf margins, but do not fall under the "cup-shaped" description (more severe than Curled 1, but less severe than Curled 3) | Useful for making plants with altered leaf shape eg curled leaves |
| ROSETTE LEAVES | Curled | Curled 3 | leaves are abnormally curled up or down at the leaf margins, but do not fall under the "cup-shaped" description (more severe than Curled 2, but less severe than Curled 4) | Useful for making plants with altered leaf shape eg curled leaves |
| ROSETTE LEAVES | Curled | Curled 4 | leaves are abnormally curled/rolled up or down at the leaf margins (more severe than Curled 3, but less severe than Curled 5) | Useful for making plants with altered leaf shape eg curled leaves |
| ROSETTE LEAVES | Curled | Curled 5 | leaves are completely curled/rolled up or down at the leaf margins (most severe type) | Useful for making plants with altered leaf shape eg curled leaves |
| CAULINE LEAVES | Curled | Corkscrew | leaves appear as "Curled 5", with the additional attribute of twisting like a corkscrew, instead of uniformly curling from both sides of the leaf | Useful for making plants with altered leaf shape eg curled leaves |
| CAULINE LEAVES | Curled | Cup-shaped | the cauline leaves are curled up at the leaf margins such that they form a cup or bowl-like shape | Useful for making plants with altered leaf shape eg curled leaves |
| CAULINE LEAVES | Curled | Curled 1 | the cauline leaves are abnormally curled slightly up or down at the leaf margins, but do not fall under the "cup-shaped" description (least severe type) | Useful for making plants with altered leaf shape eg curled leaves |

TABLE 1-continued

| TISSUE | PHENOTYPE QUALIFIER | PHENOTYPE | DESCRIPTION | TRANSLATION |
|---|---|---|---|---|
| CAULINE LEAVES | Curled | Curled 2 | the cauline leaves are abnormally curled up or down at the leaf margins, but do not fall under the "cup-shaped" description (more severe than Curled 1, but less severe than Curled 3) | Useful for making plants with altered leaf shape eg curled leaves |
| CAULINE LEAVES | Curled | Curled 3 | the cauline leaves are abnormally curled up or down at the leaf margins, but do not fall under the "cup-shaped" description (more severe than Curled 2, but less severe than Curled 4) | Useful for making plants with altered leaf shape eg curled leaves |
| CAULINE LEAVES | Curled | Curled 4 | the cauline leaves are abnormally curled/rolled up or down at the leaf margins (more severe than Curled 3, but less severe than Curled 5) | Useful for making plants with altered leaf shape eg curled leaves |
| CAULINE LEAVES | Curled | Curled 5 | the cauline leaves are completely curled/rolled up or down at the leaf margins (most severe type) | Useful for making plants with altered leaf shape eg curled leaves |
| ROSETTE LEAVES | Size | Small | rosette leaves are abnormally small (the percent difference in size compared to the control should be noted in the comments) | Useful for making plants with decreased vegetative growth |
| COTYLEDONS | Wilted | Wilted | cotyledons appear wilted, i.e., they look as though they have suffered from drought conditions | Useful for making plants with enhanced abiotic stress tolerance |
| ROSETTE LEAVES | Wax | Glaucous | leaves are abnormally dull in appearance | Useful for making plants with enhanced abiotic stress tolerance |
| ROSETTE LEAVES | Wax | Glossy | leaves are shiny/glossy in appearance | Useful for making plants with enhanced abiotic stress tolerance |
| CAULINE LEAVES | Wax | Glaucous | leaves are abnormally dull in appearance | Useful for making plants with enhanced abiotic stress tolerance |
| CAULINE LEAVES | Wax | Glossy | leaves are shiny/glossy in appearance | Useful for making plants with enhanced abiotic stress tolerance |
| WHOLE PLANT | Stress | Metabolic Profiling | Identify plants with altered metabolic profiles as defined in 4a | Useful for making plants with enhanced metabolite accumulation |
| WHOLE PLANT | Stress | Plant Architecture | Identify plants with improved architecture | Useful for making plants with enhanced plant architecture |
| WHOLE PLANT | Stress | ABA | Identify plants tolerant to ABA, and possibly drought and/or other stresses | Useful for making plants with enhanced tolerance to drought |
| WHOLE PLANT | Stress | Mannitol | Identify plants tolerant to mannitol, and possibly drought stress | Useful for making plants with enhanced tolerance to drought |
| WHOLE PLANT | Stress | Dessication | Identify plants tolerant to water loss, possibly drought stress tolerant | Useful for making plants with enhanced tolerance to drought |

TABLE 1-continued

| TISSUE | PHENOTYPE QUALIFIER | PHENOTYPE | DESCRIPTION | TRANSLATION |
|---|---|---|---|---|
| WHOLE PLANT | Stress | High Sucrose | Identify plants tolerant to high sucrose conditions (possible Lead assay for C/N partitioning) | Useful for making plants with enhanced tolerance to drought |
| WHOLE PLANT | Stress | Heat | Identify plants with thermotolerance | Useful for making plants with enhanced tolerance to heat |
| WHOLE PLANT | Stress | High Nitrogen | Identify plants tolerant to high nitrogen conditions | Useful for making plants with enhanced tolerance to high nitrogen |
| WHOLE PLANT | Stress | Etiolation | Identify plants with increased vigor in the dark | Useful for making plants with enhanced tolerance to light stress |
| ROSETTE LEAVES | Disorganized Rosette | Disorganized Rosette | rosette leaves do not appear in the normal fashion, i.e., their phyllotaxy may be abnormal or too many leaves may be emerging in comparison to the control | Useful for making plants with increased biomass |
| INFLORESCENCE | Phyllotaxy | Even Phyllotaxy | a phyllotaxy mutant whose new branches emerge at exactly the same height as each other, i.e., there is no internode between them | Useful for making plants with increased biomass |
| COTYLEDONS | Shape | Elliptic Shape | cotyledons are quite narrow and pointed, more so than lanceolate | Useful for making plants with increased biomass and foliage |
| ROSETTE LEAVES | Fused | Leaf Fused to Petiole | the leaf is fused to its petiole | Useful for making plants with increased biomass and foliage |
| ROSETTE LEAVES | Shape | Cordate Shaped | similar to ovate, except the leaf is not rounded at its base | Useful for making plants with increased biomass and foliage |
| ROSETTE LEAVES | Shape | Elliptic Shaped | leaves are quite narrow and pointed, more so that lanceolate | Useful for making plants with increased biomass and foliage |
| ROSETTE LEAVES | Shape | Lanceolate Shaped | leaves are narrow and come to a dull point at the apex | Useful for making plants with increased biomass and foliage |
| ROSETTE LEAVES | Shape | Lobed Shaped | leaves have very deep and rounded serrations, giving an appearance of many lobes forming the margins of the leaves | Useful for making plants with increased biomass and foliage |
| ROSETTE LEAVES | Shape | Oval Shaped | leaves are much rounder than wild-type | Useful for making plants with increased biomass and foliage |
| ROSETTE LEAVES | Shape | Ovate Shaped | leaves are wider at base than at apex, otherwise similar to wild-type | Useful for making plants with increased biomass and foliage |
| ROSETTE LEAVES | Shape | Serrate Margins | leaf margins have little ?teeth? on them, i.e., they are serrated | Useful for making plants with increased biomass and foliage |
| ROSETTE LEAVES | Shape | Trident Shaped | leaves look somewhat like a trident, i.e., they have a sharp point at the apex, and a sharp point on each side | Useful for making plants with increased biomass and foliage |
| ROSETTE LEAVES | Shape | Undulate Shaped | leaves are wavy | Useful for making plants with increased biomass and foliage |

TABLE 1-continued

| TISSUE | PHENOTYPE QUALIFIER | PHENOTYPE | DESCRIPTION | TRANSLATION |
|---|---|---|---|---|
| WHOLE PLANT | Rosette Shape | Bushy Rosette Shaped | the different petioles have very varied liminal angles, giving the plant a very bushy appearance; This is often accompanied by a "Disorganized Rosette" phenotype | Useful for making plants with increased biomass and foliage |
| WHOLE PLANT | Rosette Shape | Flat Rosette Shaped | the petioles have a very small liminal angle, i.e., the rosette appears flat instead of having its usual slight vertical angle | Useful for making plants with increased biomass and foliage |
| WHOLE PLANT | Rosette Shape | Standing Rosette Shaped | the petioles have a very large liminal angle, i.e., it appears as though the leaves are standing up instead of having their usual small vertical angle from the soil | Useful for making plants with increased biomass and foliage |
| CAULINE LEAVES | Fused | Leaf Fused to Inflorescence | the cauline leaf is fused to an inflorescence or branch | Useful for making plants with increased biomass and foliage |
| CAULINE LEAVES | Fused | Leaf Fused to Leaf | the cauline leaf is fused to itself or another cauline leaf | Useful for making plants with increased biomass and foliage |
| CAULINE LEAVES | Shape | Cordate Shaped | similar to ovate, except the leaf is not rounded at its base | Useful for making plants with increased biomass and foliage |
| CAULINE LEAVES | Shape | Elliptic Shaped | leaves are quite narrow and pointed, more so that lanceolate | Useful for making plants with increased biomass and foliage |
| CAULINE LEAVES | Shape | Lanceolate Shaped | leaves are narrow and come to a dull point at the apex | Useful for making plants with increased biomass and foliage |
| CAULINE LEAVES | Shape | Lobed Shaped | leaves have very deep and rounded serrations, giving an appearance of many lobes forming the margins of the leaves | Useful for making plants with increased biomass and foliage |
| CAULINE LEAVES | Shape | Oval Shaped | leaves are much rounder than wild-type | Useful for making plants with increased biomass and foliage |
| CAULINE LEAVES | Shape | Ovate Shaped | leaves are wider at base than at apex, otherwise similar to wild-type | Useful for making plants with increased biomass and foliage |
| CAULINE LEAVES | Shape | Serrate Margins | leaf margins have little ?teeth? on them, i.e., they are serrated | Useful for making plants with increased biomass and foliage |
| CAULINE LEAVES | Shape | Trident Shaped | leaves look somewhat like a trident, i.e., they have a sharp point at the apex, and a sharp point on each side | Useful for making plants with increased biomass and foliage |
| CAULINE LEAVES | Shape | Undulate Shaped | leaves are wavy | Useful for making plants with increased biomass and foliage |
| CAULINE LEAVES | Size | Large | cauline is abnormally large (the percent difference in size compared to the control should be noted in the comments) | Useful for making plants with increased biomass and foliage |

TABLE 1-continued

| TISSUE | PHENOTYPE QUALIFIER | PHENOTYPE | DESCRIPTION | TRANSLATION |
|---|---|---|---|---|
| CAULINE LEAVES | Size | Small | cauline is abnormally small (the percent difference in size compared to the control should be noted in the comments) | Useful for making plants with increased biomass and foliage |
| LATERAL ROOTS | Length | Smaller Lateral Root | the lateral roots are abnormally short | Useful for making plants with increased root growth to prevent lodging or enhance nutrient uptake |
| PRIMARY ROOT | Length | Long Primary Root | the primary root is abnormally long (the percent difference in size compared to the control should be noted in the comments) | Useful for making plants with increased root growth to prevent lodging or enhance nutrient uptake |
| PRIMARY ROOT | Length | Short Primary Root | the primary root is abnormally short (the percent difference in size compared to the control should be noted in the comments) | Useful for making plants with increased root growth to prevent lodging or enhance nutrient uptake |
| WHOLE PLANT | Stress | Plant Size | Identify plants of increased size compared to wild type | Useful for making plants with increased size and biomass |
| WHOLE PLANT | Stress | Starch | Identify plants with increased starch accumulation | Useful for making plants with increased starch content |
| WHOLE PLANT | Stress | Cold Germination | Identify plants that germinate better at cold temperatures | Useful for making plants with increased tolerance to cold stress |
| WHOLE PLANT | Stress | Cold Growth | Identify plants that grow faster at cold temperatures | Useful for making plants with increased tolerance to cold stress |
| WHOLE PLANT | Stress | Soil Drought | Identify plants with increased tolerance to soil drought | Useful for making plants with increased tolerance to drought |
| WHOLE PLANT | Stress | Soil Drought - Desiccation tolerance | Identify plants that are tolerant to low soil moisture and resist wilting | Useful for making plants with increased tolerance to drought |
| WHOLE PLANT | Stress | PEG | Identify plants tolerant to PEG, and possibly drought stress | Useful for making plants with increased tolerance to drought |
| SEED | Size | Large | the seed is abnormally large (the percent difference in size compared to the control should be noted in the comments) | Useful for making plants with larger seeds |
| INFLORESCENCE | Branching | Asecondary Branching | the plant does not form any secondary inflorescences | Useful for making plants with modified flowers |
| SEED | Size | Small | the seed is abnormally small (the percent difference in size compared to the control should be noted in the comments) | Useful for making plants with smaller seeds or no seeds |
| WHOLE PLANT | Stress | C/N Content | Identify plants/seeds with altered carbon/nitrogen levels | Useful for making seeds with altered carbon/nitrogen levels |

TABLE 1-continued

| TISSUE | PHENOTYPE QUALIFIER | PHENOTYPE | DESCRIPTION | TRANSLATION |
| --- | --- | --- | --- | --- |
| INFLORESCENCE | Internode Length | Short Internode | the internode is abnormally short (the percent difference in length compared to the control should be noted in the comments) | Useful for making shorter plants and plants with modified flowers |
| WHOLE PLANT | Dwarf | Brassino-Steroid Dwarf | these plants are small in stature, dark green, have oval leaves, strong bolts, and are often sterile | Useful for making smaller plants |
| WHOLE PLANT | Dwarf | Misc. Dwarf | these are dwarf plants the do not fall under the brassino-steroid dwarf category | Useful for making smaller plants |
| HYPOCOTYL | Length | Short | hypocotyl is visibly shorter than in wild-type (the percent difference in size compared to the control should be noted in the comments) | Useful for making smaller plants |
| INFLORESCENCE | Height | Short | the inflorescences of the plants are abnormally short (plant height is encompassed under the whole plant size category, but this entry would be used if the height of the plant is abnormal, but is otherwise of normal size) (the percent difference in size | Useful for making smaller plants |
| WHOLE SEEDLING | Size | Small | plant is abnormally small (the percent difference in size compared to the control should be noted in the comments) | Useful for making smaller plants |
| ROSETTE LEAVES | Petiole Length | Short Petioles | the leaf petioles are abnormally short (the percent difference in size compared to the control should be noted in the comments) | Useful for making smaller plants |
| WHOLE PLANT | Size | Small | plant is abnormally small (the percent difference in size compared to the control should be noted in the comments) | Useful for making smaller plants |
| CAULINE LEAVES | Petiole Length | Short Petioles | the cauline petioles are abnormally short (the percent difference in size compared to the control should be noted in the comments) | Useful for making smaller plants |
| INFLORESCENCE | Strength | Strong | the primary inflorescence appears significantly stronger, whether by thickness or rigidity | Useful for making stronger plants |

TABLE 1-continued

| TISSUE | PHENOTYPE QUALIFIER | PHENOTYPE | DESCRIPTION | TRANSLATION |
|---|---|---|---|---|
| INFLORESCENCE | Strength | Weak | the primary inflorescence appears significantly weaker, whether by thickness or rigidity | Useful for making stronger plants |
| INFLORESCENCE | Inflorescence | Thickness | thickness of the primary inflorescence | Useful for making stronger plants |
| HYPOCOTYL | Length | Long | hypocotyl is visibly longer than in wild-type (the percent difference in size compared to the control should be noted in the comments) | Useful for making taller plants |
| INFLORESCENCE | Internode Length | Long Internode | the internode is abnormally long (the percent difference in length compared to the control should be noted in the comments) | Useful for making taller plants and plants with longer flowers |
| INFLORESCENCE | Height | Tall | the inflorescences of the plants are abnormally long (plant height is encompassed under the whole plant size category, but this entry would be used if the height of the plant is abnormal, but is otherwise of normal size) (the percent difference in size | Useful for making taller plants and plants with longer inflorescences |
| SEED | Color | Dark Color | the seed is abnormally dark | Useful for modifying fiber content in seed |
| SEED | Color | Light Color | the seed is abnormally light; Transparent Testa is an example of this phenotype | Useful for modifying fiber content in seed |
| SILIQUES | Shape | Bent | the silique has sharp bend to it part of the way down the length of the silique; this bend can be as much as approaching 90 degrees | Useful for modifying fruit shape, composition and seed yield |
| SILIQUES | Shape | Bulging | the seeds in the silique appears "shrink-wrapped", giving the silique a bulging appearance | Useful for modifying fruit shape, composition and seed yield |
| SILIQUES | Shape | Clubbed | the silique is somewhat bulbous at its terminal end | Useful for modifying fruit shape, composition and seed yield |
| SILIQUES | Shape | Sickle | the silique is curved, much like the blade of a sickle | Useful for modifying fruit shape, composition and seed yield |
| INFLORESCENCE | Branching | No Branching | there is no branching at all | Useful for modifying plant architecture, ie amount of branching |
| INFLORESCENCE | Branching | Horizontal Branching | new branches arise at a 90 degree angle from the bolt they are emerging from | Useful for modifying plant architecture, ie branch angle |
| COTYLEDONS | Horizontally Oblong | Horizontally Oblong | cotyledon is visibly wider than it is long, and it is also symmetrical (or very close to it) when cut along its horizontal axis | Useful for modifying plant architecture, ie leaf structure |

TABLE 1-continued

| TISSUE | PHENOTYPE QUALIFIER | PHENOTYPE | DESCRIPTION | TRANSLATION |
|---|---|---|---|---|
| INFLORESCENCE | Branching | Two Leaf Branching | two cauline leaves subtend branches instead of one | Useful for modifying plant architecture, ie reducing foliage |
| INFLORESCENCE | Branching | Reduced Apical Dominance | the dominance of the primary inflorescence is diminished, with the secondaries appearing as dominant or nearly as dominant | Useful for modifying plant structure, ie increased branching |
| SEED | Seed Arrangement | Stacked Arrangement | the seeds/embryos are stacked one on top of the other within the silique, instead of having the usual side-by-side distribution | Useful for modifying seed content |
| SEED | Other | Other | this correlates with any seed mutant phenotypes which do not fit into the above categories (a picture should be taken for documentation) | Useful for modifying seed content |
| SEED | Shape | Oval Shape | the seeds are much more rounded on the ends, giving the seed a true oval appearance | Useful for modifying seed structure and composition |
| SEED | Shape | Ridged Shape | the seeds have small ridges or bumps on them | Useful for modifying seed structure and composition |
| SEED | Shape | Tapered Shape | the ends of the seeds narrow down to a much sharper point than usual | Useful for modifying seed structure and composition |
| COTYLEDONS | Cotyledon Number | Single Cotyledon | Only one cotyledon appears after germination; This is simply one cotyledon that had formed instead of two, and is not related to the fused phenotype; With this exception, the plant is often otherwise wild-type in appearance | Useful for modifying seed structure and content |
| COTYLEDONS | Cotyledon Number | Tricot | three cotyledons emerge instead of two; With this exception, the plant is often otherwise wild-type in appearance | Useful for modifying seed structure and content |
| COTYLEDONS | Curled | Cup-shaped | cotyledons are curled up at the cotyledon margins such that they form a cup or bowl-like shape | Useful for modifying seed structure and content |
| COTYLEDONS | Curled | Curled 1 | cotyledons are abnormally curled slightly up or down at the cotyledon margins, but do not fall under the "cup-shaped" description (least severe type) | Useful for modifying seed structure and content |
| COTYLEDONS | Curled | Curled 2 | cotyledons are abnormally curled up or down at the cotyledon margins, | Useful for modifying seed structure and content |

TABLE 1-continued

| TISSUE | PHENOTYPE QUALIFIER | PHENOTYPE | DESCRIPTION | TRANSLATION |
|---|---|---|---|---|
| | | | but do not fall under the "cup-shaped" description (more severe than Curled 1, but less severe than Curled 3) | |
| COTYLEDONS | Curled | Curled 3 | cotyledons are abnormally curled up or down at the cotyledon margins, but do not fall under the "cup-shaped" description (more severe than Curled 2, but less severe than Curled 4) | Useful for modifying seed structure and content |
| COTYLEDONS | Curled | Curled 4 | cotyledons are abnormally curled/rolled up or down at the cotyledon margins (more severe than Curled 3, but less severe than Curled 5) | Useful for modifying seed structure and content |
| COTYLEDONS | Curled | Curled 5 | cotyledons are completely curled/rolled up or down at the cotyledon margins (most severe type) | Useful for modifying seed structure and content |
| COTYLEDONS | Dimorphic Cotyledons | Dimorphic Cotyledons | one cotyledon is significantly larger than the other | Useful for modifying seed structure and content |
| COTYLEDONS | Fused | Fused 1 | cotyledons are fused to each other, creating one cotyledon structure (least severe type) | Useful for modifying seed structure and content |
| COTYLEDONS | Fused | Fused 2 | cotyledons are fused to each other, creating one cotyledon structure (more severe than Fused 1, but less severe than Fused 3) | Useful for modifying seed structure and content |
| COTYLEDONS | Fused | Fused 3 | cotyledons are fused to each other, creating one cotyledon structure (more severe than Fused 2, but less severe than Fused 4) | Useful for modifying seed structure and content |
| COTYLEDONS | Fused | Fused 4 | cotyledons are fused to each other, creating one cotyledon structure (more severe than Fused 3, but less severe than Fused 5) | Useful for modifying seed structure and content |
| COTYLEDONS | Fused | Fused 5 | cotyledons are fused to each other, creating one cotyledon structure (most severe type) | Useful for modifying seed structure and content |
| COTYLEDONS | Other | Other | this correlates with any cotyledon mutant phenotypes which do not fit into the above categories (a picture should be taken for documentation) | Useful for modifying seed structure and content |
| ROSETTE LEAVES | Fused | Leaf Fused to Leaf | the leaf is fused to itself or another leaf | Useful for plants with fused leaves eg ornamentals |

TABLE 1-continued

| TISSUE | PHENOTYPE QUALIFIER | PHENOTYPE | DESCRIPTION | TRANSLATION |
|---|---|---|---|---|
| COTYLEDONS | Petiole Length | Short Petioles | the cotyledon petioles are abnormally short (the percent difference in size compared to the control should be noted in the comments) | Useful for shade avoidance and for making smaller plants |
| PRIMARY ROOT | Agravitropic | Agravitropic | the primary root does not appear to have a gravitropic response | |
| PRIMARY ROOT | Kinked | Kinked | there is a sharp bend in the root | |
| ROSETTE LEAVES | Rosette Diameter | Diameter | diameter of rosette | |
| WHOLE PLANT | Plant Weight | Plant Weight | weight of whole plant | |
| WHOLE PLANT | Plant Height | Height | height of whole plant | |
| WHOLE PLANT | Plant DTH | Dth | days to harvest of plant | |
| WHOLE PLANT | Plant Harvest Index | Harvest Index | harvest index of plant | |
| CAULINE LEAVES | Fused | Leaf Fused to Petiole | the cauline leaf is fused to its petiole | |
| N/A | N/A | N/A | N/A | |
| WHOLE PLANT | HERBICIDE SEGREGATION | HERBICIDE SEGREGATION | herbicide segregation ratio | |
| WHOLE PLANT | N/A | No Mutant Phenotype Observed | The plants were screened at all appropriate stages and showed no mutant phenotype, i.e., they looked like normal, wild type *Arabidopsis* plants | |

From the results reported in Table 1 and the Sequence Listing, it can be seen that the nucleotides/polypeptides of the inventions are useful, depending upon the respective individual sequence, to make plants with modified growth and phenotype characteristics, including:
 a. modulated plant size, including increased and decreased height or length;
 b. modulated vegetative growth (increased or decreased);
 c. modulated organ number;
 d. increased biomass;
 e. sterility;
 f. seedling lethality;
 g. accelerated crop development or harvest;
 h. accelerated flowering time;
 i. delayed flowering time;
 j. delayed senescence;
 k. enhanced drought or stress tolerance;
 l. increased chlorophyll and photosynthetic capacity;
 m. increased anthocyanin content;
 n. increased root growth, and increased nutrient uptake;
 o. increased or decreased seed weight or size, increased seed carbon or nitrogen content;
 p. modified, including increased, seed/fruit yield or modified fruit content;
 q. enhanced foliage;
 r. usefulness for making nutratceuticals/pharmaceuticals in plants;
 s. plant lethality;
 t. decrease seed fiber content to provide increased digestability;
 u. modified ornamental appearance with modified leaves, flowers, color or foliage;
 v. modified sterility in plants;
 w. enhanced ability to grow in shade;
 x. enhanced biotic stress tolerance;
 y. increased tolerance to density and low fertilizer;
 z. enhanced tolerance to high or low pH, to low or high nitrogen or phosphate;
 aa. enhanced tolerance to oxidative stress;
 bb. enhanced chemical composition;
 cc. altered leaf shape;
 dd. enhanced abiotic stress tolerance;
 ee. increased tolerance to cold stress;
 ff. increased starch content;
 gg. reduced number or no seeds;
 hh. enhanced plant strength;
 ii. modified flower length;
 jj. longer inflorescences;
 kk. modified seed fiber content;
 ll. modified fruit shape;
 mm. modified fruit composition;
 nn. modified seed yield;
 oo. modified plant architecture, such as modified amount or angle of branching, modified leaf structure, or modified seed structure; and
 pp. enhanced shade avoidance.

EXAMPLE 1

Lead 80 (ME08386); Clone 733804 SEQ ID NO. 94

Lead 80 (SEQ ID NO. 94) encodes a 92 amino acid bHLH transcription factor from wheat. Plants transformed with this sequence were found to exhibit:

Enhanced growth, particularly on low-nitrate-containing media;

Enhanced photosynthesis on low-nitrate containing media;

Elongated hyocotyls, narrow leaves and often a flattened inflorescence.

Clone 733804 encodes a bHLH transcription factor that confers increased growth and improved photosynthetic efficiency on plants experiencing nitrogen deficiency stress. Transcription factors often control the expression of multiple genes in a pathway. As such, Clone 733804 may be involved in controlling the expression of several genes in a pathway, such as carbon flux through the TCA cycle (Yanagisawa et al., 2004). A related *Arabidopsis* bHLH transcription factor and potential ortholog (60% identity; clone 8607) is also able to confer a similar low nitrogen stress phenotype. Since the gain-of-function phenotype of clones 733804 and clone 8607 is conserved between wheat and *Arabidopsis*, these genes can have direct application for improving nitrogen stress tolerance increasing nitrogen use efficiency, and enhancing seedling vigor in a broad range of crops.

Material and Methods:

Generation and Phenotypic Evaluation of $T_1$ Events.

Wild-type *Arabidopsis* Wassilewskija (Ws) plants were transformed with a Ti plasmid containing Clone 733804 in the sense orientation relative to the 35S promoter, as described above. The Ti plasmid vector used for this construct, CRS 338, contains the Ceres-constructed, plant selectable marker gene phosphinothricin acetyltransferase (PAT) which confers herbicide resistance to transformed plants. Ten independently transformed events were selected and evaluated for their qualitative phenotype in the $T_1$ generation.

The procedure for 1) identifying the candidate from a low nitrate tolerance superpool screen, 2) confirming the phenotype in the second and third generations and 3) determining the lack of significant negative phenotypes was as described below.

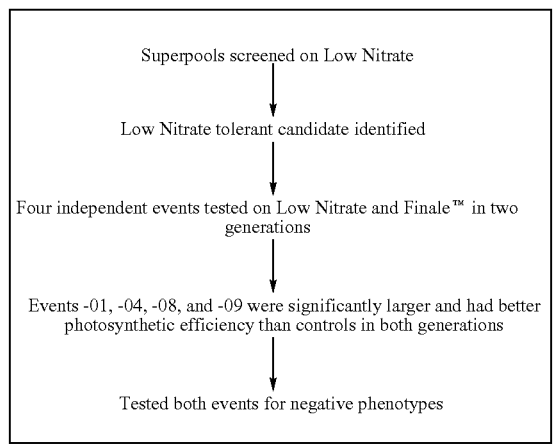

Screening Superpools 62-71 for Tolerance to Low Nitrate Growth Conditions.

Two thousand seeds each from Superpools 62-71 were pooled together and plated on low nitrate media DNA was isolated from each candidate plant and sequenced to determine which transgene was present.

Growth Conditions and Planting Schema for ME08386 Under Low Nitrate Growth Conditions.

Evaluation of tolerance to low nitrate conditions (300 µM $KNO_3$ MS media) was done using five $T_2$ events (-01, -03, -04, -08 and -09). Subsequently, $T_3$ generation seeds for all five events were evaluated under low nitrate conditions.

Results:

ME08386 was Identified from a Superpool Screen for Seedling Tolerance to Low Nitrate Conditions.

Superpools 62-71 were screened for seedlings that were larger or greener than controls on low nitrate growth media. Transgene sequence was obtained for 19 candidate seedlings. Two of the 19 candidate sequences BLASTed to ME08386.

Four Events of ME08386 Show 3:1 Segregation for Finale™ Resistance.

Events -01, -04, -08 and -09 segregated 3:1 (R:S) for Finale™ resistance in the $T_2$ generation (data not shown).

Four Events of ME08386 Showed Significantly Increased Growth Under Low Nitrate Growth Conditions in Both Generations.

Five events of ME08386 were sown as described in the Low Nitrate Assay in both the $T_2$ and the $T_3$ generations. In this study the seedling area at 14 days for transgenic plants within an event was compared to the seedling area for non-transgenic segregants pooled across the same plate. Four events, -01, -04, -08 and -09, were significant in both generations at p=0.05, using a one-tailed t-test assuming unequal variance (Table 1-1).

TABLE 1-1

T-test comparison of seedling area between transgenic seedlings and pooled non-transgenic segregants after 14 days of growth on low nitrate.

| Line | Events | Transgenic Avg ($cm^2$) | n | Pooled Non-Transgenics Avg ($cm^2$) | n | t-test p-value |
|---|---|---|---|---|---|---|
| ME08386 | ME08386-01 | 0.073 | 29 | 0.056 | 17 | 0.00132 |
| ME08386 | ME08386-01-99 | 0.086 | 32 | 0.056 | 17 | 9.83E−07 |
| ME08386 | ME08386-04 | 0.067 | 32 | 0.056 | 18 | 9.22E−05 |
| ME08386 | ME08386-04-99 | 0.078 | 29 | 0.056 | 18 | 3.74E−06 |
| ME08386 | ME08386-08 | 0.064 | 27 | 0.053 | 20 | 0.0105 |
| ME08386 | ME08386-08-99 | 0.087 | 29 | 0.053 | 20 | 1.54E−09 |
| ME08386 | ME08386-09 | 0.065 | 30 | 0.057 | 19 | 0.00549 |
| ME08383 | ME08386-09-99 | 0.072 | 32 | 0.057 | 19 | 9.57E−07 |

Four Events of ME08386 Showed Significantly Increased Photosynthetic Efficiency under Low Nitrate Growth Conditions in Both Generations.

Five events of ME08386 were sown as described in the Low Nitrate Assay in both the $T_2$ and the $T_3$ generations. In this study, the seedling photosynthetic efficiency was measured as Fv/Fm comparing transgenic plants within an event to non-transgenic segregants pooled across the same plate. Four events, -01, -04, -08 and -09, were significant in both generations at p=0.05, using a one-tailed t-test assuming unequal variance (Table 1-2).

TABLE 1-2

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME08386 | ME08386-01 | 0.59 | 29 | 0.56 | 17 | 0.00982 |
| ME08386 | ME08386-01-99 | 0.64 | 32 | 0.56 | 17 | 8.76E−07 |
| ME08386 | ME08386-04 | 0.61 | 31 | 0.56 | 19 | 0.00338 |
| ME08386 | ME08386-04-99 | 0.61 | 28 | 0.56 | 19 | 0.00402 |

TABLE 1-2-continued

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME08386 | ME08386-08 | 0.62 | 28 | 0.52 | 21 | 4.69E−05 |
| ME08386 | ME08386-08-99 | 0.63 | 26 | 0.52 | 21 | 1.59E−09 |
| ME08386 | ME08386-09 | 0.58 | 30 | 0.51 | 18 | 0.000819 |
| ME08383 | ME08386-09-99 | 0.58 | 32 | 0.51 | 18 | 0.000357 |

Qualitative Analysis of the $T_1$ Plants:

The physical appearance of four of the ten $T_1$ plants was identical to the controls. Events -01, -03, -04, -08, -09 and -10 were noted as having flat inflorescences, but were still fully fertile.

Qualitative and Quantitative Analysis of the $T_2$ Plants (Screening for Negative Phenotypes):

Events -01, -04, -08 and -09 of ME08386 exhibited no statistically relevant negative phenotypes. All four events showed the same flat inflorescence phenotype as noted in the $T_1$ generation, but this phenotype does not negatively affect yield. The plants also had slightly elongated hypocotyls and rosette leaves. The plants exhibited slightly elongated hypocotyls, elongated rosette leaves and flat bolts. But exhibited no observable or statistical differences between experimentals and controls with respect to germination rate, days to flowering, rosette after 7 days post-bolting, or fertility (silique number and seed fill).

EXAMPLE 2

Lead 81 (ME03973) Clone 8607 SEQ ID NO. 96

Lead 81 (SEQ ID NO. **) encodes a 94 amino acid bHLH transcription factor from *Arabidopsis*. Plants transformed with this sequence were found to exhibit:

Enhanced growth, particularly on low-nitrate-containing media;
Enhanced photosynthesis on low-nitrate containing media;
Elongate hypocotyls, narrow leaves and often a flattened inflorescence.

Clone 8607 encodes an *Arabidopsis* basic-helix-loop-helix transcription factor. The clone was placed in the cDNA misexpression pipeline to test its utility in improving plant performance under various stress conditions. The gene is differentially expressed in heat, drought, and nitrogen-deficiency stress experiments and, therefore, can play a role in regulating genes important for stress tolerance or adaptation.

Clone 8607 encodes a bHLH transcription factor that confers increased growth and improved photosynthetic efficiency on plants experiencing nitrogen deficiency stress. Transcription factors often control the expression of multiple genes in a pathway. Clone 8607 may be involved in controlling the expression of several genes in a pathway, such as carbon flux through the TCA cycle (Yanagisawa et al., 2004). The function of clone 8607 is not known, but its regulation by nitrogen stress indicates it can function in plant responses to nitrogen deficiency. A related wheat bHLH transcription factor and potential ortholog (60% identity; clone 733804) is also able to confer a similar low nitrogen stress phenotype. Since the gain of function phenotype of clones 733804 and clone 8607 is conserved between wheat and *Arabidopsis*, these genes can have direct application for improving nitrogen stress tolerance and increasing nitrogen use efficiency and enhancing seedling vigor in a broad range of crops.

Materials and Methods:

Generation and Phenotypic Evaluation of $T_1$ Events.

Wild-type *Arabidopsis* Wassilewskija (Ws) plants were transformed with a Ti plasmid containing Clone 8607 in the sense orientation relative to the 35S promoter, as described above. The Ti plasmid vector used for this construct, CRS 338, contains the Ceres-constructed, plant selectable marker gene phosphinothricin acetyltransferase (PAT) which confers herbicide resistance to transformed plants. Five independently transformed events were selected and evaluated for their qualitative phenotype in the $T_1$ generation as per Ceres SOP 5-HTP T1 Plant Phenotyping.

The procedure for 1) identifying the candidate from a low nitrate tolerance superpool screen, 2) confirming the phenotype in the second and third generations and 3) determining the lack of significant negative phenotypes was as described below.

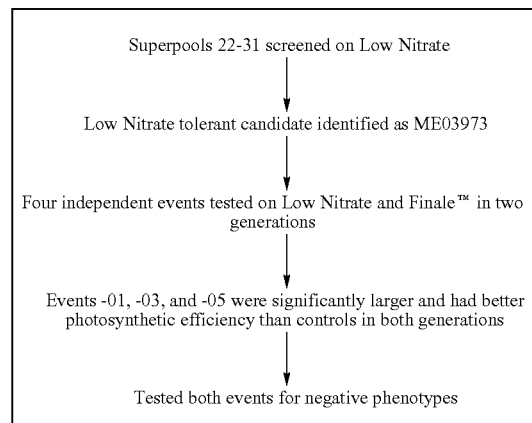

Screening Superpools 22-31 for Tolerance to Low Nitrate Growth Conditions.

Two thousand seeds each from Superpools 22-31 were pooled together and plated on low nitrate media DNA was isolated from each candidate plant and sequenced to determine which transgene was present.

Growth Conditions and Planting Schema for ME03973 Under Low Nitrate Growth Conditions.

Evaluation of tolerance to low nitrate conditions (300 µM $KNO_3$ MS media) was done using four $T_2$ events (-01, -02, -03 and -05). Subsequently, $T_3$ generation seeds for all four events were evaluated under low nitrate conditions.

Results:

ME03973 was Identified from a Superpool Screen for Seedling Tolerance to Low Nitrate Conditions.

Superpool 27 was screened for seedlings that were larger or greener than controls on low nitrate growth media. Line ME03973 was identified from among the candidates.

Superpools 22-31 were screened for seedlings that were larger or greener than controls on low nitrate growth media. Transgene sequence was obtained for 39 candidate seedlings. One of the 39 candidate sequences BLASTed to ME03973.

Three Events of ME03973 Show 3:1 Segregation for Finale™ Resistance.

Events -01, -03 and -05 segregated 3:1 (R:S) for Finale™ resistance in the $T_2$ generation.

Three Events of ME03973 Showed Significantly Increased Growth Under Low Nitrate Growth Conditions in Both Generations.

Four events of ME03973 were tested on the Low Nitrate Assay in both the $T_2$ and the $T_3$ generations. In this study, the seedling area at 14 days for transgenic plants within an event was compared to the seedling area for non-transgenic segregants pooled across the same plate. Three events, -01, -03 and -05, were significant in both generations at p=0.05, using a one-tailed t-test assuming unequal variance (Table 2-1).

TABLE 2-1

T-test comparison of seedling area between transgenic seedlings and pooled non-transgenic segregants after 14 days of growth on low nitrate.

| Line | Events | Transgenic Avg (cm²) | n | Pooled Non-Transgenics Avg (cm²) | n | t-test p-value |
|---|---|---|---|---|---|---|
| ME03973 | ME03973-01 | 0.077 | 27 | 0.055 | 17 | 2.35E−08 |
| ME03973 | ME03973-01-99 | 0.083 | 35 | 0.055 | 17 | 3.20E−10 |
| ME03973 | ME03973-03 | 0.073 | 33 | 0.056 | 11 | 0.000118 |
| ME03973 | ME03973-03-99 | 0.086 | 33 | 0.056 | 11 | 6.05E−06 |
| ME03973 | ME03973-05 | 0.069 | 29 | 0.061 | 20 | 0.0101 |
| ME03973 | ME03973-05-99 | 0.077 | 29 | 0.061 | 20 | 1.69E−05 |

Three Events of ME03973 Showed Significantly Increased Photosynthetic Efficiency Under Low Nitrate Growth Conditions in Both Generations.

Four events of ME03973 were tested on the Low Nitrate Assay in both the $T_2$ and the $T_3$ generations. In this study, the seedling photosynthetic efficiency was measured as Fv/Fm comparing transgenic plants within an event to non-transgenic segregants pooled across the same plate. Three events, -01, -03 and -05, were significant in both generations at p=0.05, using a one-tailed t-test assuming unequal variance (Table 2-2).

TABLE 2-2

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME03973 | ME03973-01 | 0.61 | 27 | 0.56 | 17 | 0.000812 |
| ME03973 | ME03973-01-99 | 0.63 | 35 | 0.56 | 17 | 9.38E−06 |
| ME03973 | ME03973-03 | 0.61 | 33 | 0.54 | 12 | 0.00131 |
| ME03973 | ME03973-03-99 | 0.63 | 33 | 0.54 | 12 | 4.11E−05 |
| ME03973 | ME03973-05 | 0.61 | 29 | 0.54 | 20 | 0.000375 |
| ME03973 | ME03973-05-99 | 0.63 | 26 | 0.54 | 20 | 8.18E−06 |

Qualitative Analysis of the $T_1$ Plants:

The noted physical appearance of the ten plants was identical to the controls. However, it is very likely that the elongated hypocotyls and rosette leaves, and flattened inflorescence was phenotype was present in the $T_1$ plants, but too subtle to be noted.

Qualitative and Quantitative Analysis of the $T_2$ Plants (Screening for Negative Phenotypes):

Events -01, -03 and -05 of ME03973 exhibited no statistically relevant negative phenotypes. However, all events showed a flat inflorescence phenotype as noted in the $T_1$ generation, but this phenotype does not negatively affect yield. The plants also had slightly elongated hypocotyls and rosette leaves. The plants exhibited These events had slightly elongated hypocotyls, elongated rosette leaves and flat bolts, but exhibited no observable or statistical differences between experimentals and controls with respect to germination rate, days of the flowering, rosette area 7 days post-bolting, or fertility (silique number and seed fill).

EXAMPLE 3

Lead 113 (ME08317): Clone 560948
SEQ ID NO. 90

| Construct | Event/Generation | Plant Stage | Assay | Result |
|---|---|---|---|---|
| 35S::560948 | -01/$T_2$ segregating plants | Seedling | Low Nitrate Tolerance | Significant at p ≦ .05 |
| 35S::560948 | -05/$T_2$ segregating plants | Seedling | Low Nitrate Tolerance | Significant at p ≦ .05 |
| 35S::560948 | -01/$T_3$ segregating plants | Seedling | Low Nitrate Tolerance | Significant at p ≦ .05 |
| 35S::560948 | -05/$T_3$ segregating plants | Seedling | Low Nitrate Tolerance | Significant at p ≦ .05 |

Ectopic expression of Clone 560948 under the control of the 35S promoter results in enhanced growth on low nitrate-containing media after 14 days compared to controls.

ME08317 is Homologous to Leads 80 & 81.

ME08317 was identified from a reciprocal BLAST algorithm as having between 60-70% identity to Leads 80 & 81.

One Event of ME08317 Segregates for a Single Insert, While the Other Event Segregates for 2 Inserts.

Event -01 segregated 3:1 (R:S) for Finale™ resistance in the $T_2$ generation. Event -05 segregated 15:1 (R:S) (data not shown).

Two Events of ME08317 Showed Significantly Enhanced Growth Under Low Nitrate Growth Conditions in Both Generations.

Seeds representing two events of ME08317 from each of the $T_2$ and the $T_3$ generations were sown under conditions described in the Low Nitrate Assay. Both events, -01 and -05, showed a significant increase in growth in both generations at p=0.05 as measured using a one-tailed t-test and assuming unequal variance (Table 3-1).

TABLE 3-1

T-test comparison of seedling area between transgenic seedlings and pooled non-transgenic segregants after 14 days of growth on low nitrate.

| Line | Events | Transgenic Avg (cm²) | n | Pooled Non-Transgenics Avg (cm²) | n | t-test p-value |
|---|---|---|---|---|---|---|
| ME08317 | ME08317-01 ($T_2$) | 0.076 | 41 | 0.058 | 32 | $6.8 \times 10^{-7}$ |
| ME08317 | ME08317-01 ($T_3$) | 0.074 | 27 | 0.058 | 32 | $1.7 \times 10^{-8}$ |

TABLE 3-1-continued

T-test comparison of seedling area between transgenic seedlings
and pooled non-transgenic segregants after 14 days of growth
on low nitrate.

| Line | Events | Transgenic Avg (cm$^2$) | n | Pooled Non-Transgenics Avg (cm$^2$) | n | t-test p-value |
|---|---|---|---|---|---|---|
| ME08317 | ME08317-05 (T$_2$) | 0.081 | 47 | 0.055 | 18 | $5.5 \times 10^{-8}$ |
| ME08317 | ME08317-05 (T$_3$) | 0.078 | 35 | 0.055 | 18 | $3.6 \times 10^{-8}$ |

Qualitative Analysis of the T$_1$ Plants:

All events appeared wild-type. It is possible the T$_2$ morphological phenotype below was present in the T$_1$ generation, but too subtle to be noted.

Qualitative and Quantitative Analysis of the T$_2$ Plants:

Events -01 and -05 of ME08317 had flat inflorescences and slightly elongated hypocotyls and rosette leaves.

EXAMPLE 4

Lead 114 (ME10686); Clone 336524
(SEQ ID NO: 82)

| Construct | Event/Generation | Plant Stage | Assay | Result |
|---|---|---|---|---|
| 35S::336524 | -01/T$_3$ segregating plants | Seedling | Low Ammonium Nitrate Tolerance | Significant at p ≤ .05 |
| 35S::336524 | -08/T$_2$ segregating plants | Seedling | Low Ammonium Nitrate Tolerance | Significant at p ≤ .05 |
| 35S::336524 | -01/T$_4$ segregating plants | Seedling | Low Ammonium Nitrate Tolerance | Significant at p ≤ .05 |
| 35S::336524 | -08/T$_3$ segregating plants | Seedling | Low Ammonium Nitrate Tolerance | Significant at p ≤ .05 |

Ectopic expression of Clone 336524 under the control of the 35S promoter results in enhanced growth on low nitrate-containing media after 14 days compared to controls.

ME10686 is Homologous to Leads 80 & 81.

ME10686 was identified from a reciprocal BLAST algorithm as having approximately 60% identity to Leads 80 & 81.

Two Events of ME10686 Segregate for a Single Insert.

Events -01 and -08 segregated 3:1 (R:S) for Finale® resistance in the T$_2$ generation (data not shown).

Two Events of ME10686 Showed Significantly Enhanced Growth Under Low Ammonium Nitrate Growth Conditions in Both Generations.

Seeds representing two events of ME10686 from each of the T$_2$ and the T$_3$ generations (or T$_3$ and T$_4$ generations, as is the case for Event -01) were sown under conditions described in the Low Ammonium Nitrate Assay. Both events, -01 and -08, showed a significant increase in growth in both generations at p=0.05 as measured using a one-tailed t-test and assuming unequal variance (Table 4-1).

TABLE 4-1

T-test comparison of seedling area between transgenic
seedlings and pooled non-transgenic segregants after
14 days of growth on low ammonium nitrate.

| Line | Events | Transgenic Avg (cm$^2$) | n | Pooled Non-Transgenics Avg (cm$^2$) | n | t-test p-value |
|---|---|---|---|---|---|---|
| ME10686 | ME10686-01 (T$_3$) | 0.081 | 44 | 0.063 | 6 | $1.36 \times 10^{-5}$ |
| ME10686 | ME10686-01 (T$_4$) | 0.078 | 50 | 0.063 | 6 | $9.06 \times 10^{-5}$ |
| ME10686 | ME10686-08 (T$_2$) | 0.111 | 31 | 0.084 | 20 | $5.73 \times 10^{-4}$ |
| ME10686 | ME10686-08 (T$_3$) | 0.103 | 41 | 0.084 | 20 | $1.15 \times 10^{-3}$ |

Qualitative Analysis of the T$_1$ Plants:

All events appeared wild-type. It is possible the T$_2$ morphological phenotype below was present in the T$_1$ generation, but too subtle to be noted.

Qualitative and Quantitative Analysis of the T$_2$ Plants:

Events -01 and -08 of ME08317 flat inflorescences and slightly elongated hypocotyls and rosette leaves.

EXAMPLE 5

Lead ME08328: Clone 560681 (SEQ ID NO:88)

| Construct | Event/Generation | Plant Stage | Assay | Result |
|---|---|---|---|---|
| 35S::560681 | -05/T$_2$ segregating plants | Seedling | Low Ammonium Nitrate Tolerance | Significant at p ≤ .05 |
| 35S::560681 | -05/T$_2$ segregating plants | Seedling | Low Nitrate Tolerance | Significant at p ≤ .05 |

ME08328 was identified from a reciprocal BLAST algorithm as having approximately 70% identity to Leads 80 & 81.

ME08328-05 Segregates for a Single Insert.

Event -05 segregated 3:1 (R:S) for Finales resistance in the T$_2$ generation (data not shown).

One Event of ME08328 Showed Significantly Enhanced Growth Under Both Low Ammonium Nitrate and Low Nitrate Growth Conditions.

Seeds representing one event of ME08328 were sown under conditions described in the Low Ammonium Nitrate and Low Nitrate Assays. Event -05 showed a significant increase in growth in both generations at p=0.05 as measured using a one-tailed t-test and assuming unequal variance (Tables 5-1 and 5-2).

TABLE 5-1

T-test comparison of seedling area between transgenic seedlings and pooled non-transgenic segregants after 17 days of growth on low ammonium nitrate.

| Line | Events | Transgenic Avg (cm$^2$) | n | Pooled Non-Transgenics Avg (cm$^2$) | n | t-test p-value |
|---|---|---|---|---|---|---|
| ME08328 | ME08328-05($T_2$) | 0.107 | 16 | 0.081 | 25 | $5.11 \times 10^{-5}$ |

TABLE 5-2

T-test comparison of seedling area between transgenic seedlings and pooled non-transgenic segregants after 17 days of growth on low nitrate.

| Line | Events | Transgenic Avg (cm$^2$) | n | Pooled Non-Transgenics Avg (cm$^2$) | n | t-test p-value |
|---|---|---|---|---|---|---|
| ME08328 | ME08328-05($T_2$) | 0.069 | 14 | 0.057 | 18 | 0.048 |

Qualitative Analysis of the $T_1$ Plants:
All events appeared wild-type.

EXAMPLE 6

Lead ME01905; Clone 4734 (SEQ ID NO: 84)

| Construct | Event/Generation | Plant Stage | Assay | Result |
|---|---|---|---|---|
| 35S::4734 | -03/$T_2$ segregating plants | Seedling | Low Ammonium Nitrate Tolerance | Significant at p ≦ .05 |
| 35S::4734 | -05/$T_2$ segregating plants | Seedling | Low Ammonium Nitrate Tolerance | Significant at p ≦ .05 |
| 35S::4734 | -03/$T_2$ segregating plants | Seedling | Low Nitrate Tolerance | Significant at p ≦ .05 |
| 35S::4734 | -05/$T_2$ segregating plants | Seedling | Low Nitrate Tolerance | Significant at p ≦ .05 |

ME01905 is Homologous to Leads 80 & 81.

ME01905 was identified from a reciprocal BLAST algorithm as having approximately 60% identity to Leads 80 & 81.

Two Events of ME01905 Show 3:1 Segregation for Finale™ Resistance.

Events -03 and -05 segregated 3:1 (R:S) for Finale™ resistance in the $T_2$ generation (data not shown).

Two Events of ME01905 Showed Significantly Enhanced Growth Under Both Low Ammonium Nitrate and Low Nitrate Growth Conditions.

Seeds representing two events of ME01905 were sown under conditions described in the Low Ammonium Nitrate and Low Nitrate Assays. Events -03 and -05 showed a significant increase in growth in both generations at p=0.05 as measured using a one-tailed t-test and assuming unequal variance (Tables 6-1 and 6-2).

TABLE 6-1

T-test comparison of seedling area between transgenic seedlings and pooled non-transgenic segregants after 17 days of growth on low ammonium nitrate.

| Line | Events | Transgenic Avg (cm$^2$) | n | Pooled Non-Transgenics Avg (cm$^2$) | n | t-test p-value |
|---|---|---|---|---|---|---|
| ME01905 | ME08328-03($T_2$) | 0.119 | 13 | 0.088 | 34 | 0.0012 |
| ME01905 | ME08328-05($T_2$) | 0.107 | 17 | 0.096 | 32 | 0.0041 |

TABLE 6-2

T-test comparison of seedling area between transgenic seedlings and pooled non-transgenic segregants after 17 days of growth on low nitrate.

| Line | Events | Transgenic Avg (cm$^2$) | n | Pooled Non-Transgenics Avg (cm$^2$) | n | t-test p-value |
|---|---|---|---|---|---|---|
| ME01905 | ME08328-03($T_2$) | 0.086 | 12 | 0.058 | 31 | $1.58 \times 10^{-5}$ |
| ME01905 | ME08328-05($T_2$) | 0.075 | 17 | 0.06 | 33 | $8.91 \times 10^{-5}$ |

Qualitative Analysis of the $T_1$ Plants:

Events -01, -02, -03 and -05 had flat inflorescences, but were still fully fertile. Event -03 was also noted as having a glossy appearance.

Qualitative and Quantitative Analysis of the $T_2$ Plants:

Events -01, -02, -03 and -05 of ME01905 had flat inflorescences and slightly elongated hypocotyls and rosette leaves. Events -01, -03 and -05 had a smaller rosette size and less seed yield compared to the control. Event -02 had a normal rosette size and seed yield.

EXAMPLE 7

Lead ME01770: Clone 519 (SEQ ID NO: 86)

| Construct | Event/Generation | Plant Stage | Assay | Result |
|---|---|---|---|---|
| 35S::519 | -02/$T_3$ segregating plants | Seedling | Low Ammonium Nitrate Tolerance | Significant at p ≦ .05 |
| 35S::4734 | -07/$T_3$ segregating plants | Seedling | Low Ammonium Nitrate Tolerance | Significant at p ≦ .05 |
| 35S::519 | -02/$T_3$ segregating plants | Seedling | Low Nitrate Tolerance | Significant at p ≦ .05 |
| 35S::4734 | -07/$T_3$ segregating plants | Seedling | Low Nitrate Tolerance | Significant at p ≦ .05 |

ME01770 is Homologous to Leads 80 & 81.

ME01770 was identified from a reciprocal BLAST algorithm as having approximately 70% identity to Leads 80 & 81.

Two Events of ME01770 Show 3:1 Segregation for Finale™ Resistance.

Events -02 and -07 segregated 3:1 (R:S) for Finale™ resistance in the $T_2$ generation (data not shown).

Two Events of ME01770 Showed Significantly Enhanced Growth Under Both Low Ammonium Nitrate and Low Nitrate Growth Conditions.

Seeds representing two events of ME01770 were sown under conditions described in the Low Ammonium Nitrate and Low Nitrate Assays. Events -02 and -07 showed a significant increase in growth in both generations at p=0.05 as measured using a one-tailed t-test and assuming unequal variance (Tables 7-1 and 7-2).

TABLE 7-1

T-test comparison of seedling area between transgenic seedlings and pooled non-transgenic segregants after 17 days of growth on low ammonium nitrate.

| Line | Events | Transgenic Avg (cm²) | n | Pooled Non-Transgenics Avg (cm²) | n | t-test p-value |
|---|---|---|---|---|---|---|
| ME01770 | ME01770-02($T_3$) | 0.125 | 12 | 0.106 | 17 | 0.0025 |
| ME01770 | ME01770-07($T_3$) | 0.121 | 11 | 0.088 | 34 | $1.74 \times 10^{-4}$ |

TABLE 7-2

T-test comparison of seedling area between transgenic seedlings and pooled non-transgenic segregants after 17 days of growth on low nitrate.

| Line | Events | Transgenic Avg (cm²) | n | Pooled Non-Transgenics Avg (cm²) | n | t-test p-value |
|---|---|---|---|---|---|---|
| ME01770 | ME01770-02($T_3$) | 0.115 | 12 | 0.083 | 11 | $5.85 \times 10^{-4}$ |
| ME01770 | ME01770-07($T_3$) | 0.083 | 10 | 0.058 | 31 | 0.0013 |

Qualitative Analysis of the $T_1$ Plants:

Event -01 was small with a long hypocotyl and died before flowering. Events -08 and -09 had long hypocotyls and died before flowering. Events -03 and -04 were small. Events -02 and -05 had long hypocotyls. Events -06 and -07 were small with long hypocotyls.

Qualitative and Quantitative Analysis of the $T_2$ Plants:

Events -02, -04, -05, -06 and -07 of ME01770 had flat inflorescences and slightly elongated hypocotyls and rosette leaves. These events also had smaller rosettes and less seed yield compared to controls.

EXAMPLE 8

Lead ME21445: Clone 653656 (SEQ ID NO: 92)

| Construct | Generation | Plant Stage | Assay | Result |
|---|---|---|---|---|
| 326::653656 | $T_1$ plants | Seedling | Morphological Phenotyping | Significant |

ME21445 is Homologous to Leads 80 & 81.

ME21445 was identified from a reciprocal BLAST algorithm as having approximately 80% identity to Leads 80 & 81.

Multiple Events of ME21445 Showed Significantly Enhanced Growth as $T_1$ Seedlings, with No Apparent Negative Phenotypes.

Transformed seeds containing the 326::653656 construct were sown under conditions described in the High Throughput Screening—T1 Generation protocol. Multiple seedlings/events appeared much larger than the control, but exhibited no apparent negative phenotypes, such as reduced rosette size or seed yield, as mature plants.

EXAMPLE 9

Lead ME20023; Genomic Locus At1g226945 (SEQ ID NO: 80)

| Construct | Generation | Plant Stage | Assay | Result |
|---|---|---|---|---|
| 35S::At1g26945 | $T_1$ plants | Seedling | Morphological Phenotyping | Significant |

ME20023 is Homologous to Leads 80 & 81.

ME20023 was identified from a reciprocal BLAST algorithm as having approximately 80% identity to Leads 80 & 81.

Multiple Events of ME21445 Showed Significantly Enhanced Growth as $T_1$ Seedlings, with Elongated Hypocotyls, Flat Inflorescences, and Oblong Leaves.

Transformed seeds containing the 35S::At1g26945 construct were sown under conditions described in the High Throughput Screening—T1 Generation protocol. Multiple seedlings/events appeared much larger and with elongated hypocotyls compared to the control. The plants exhibited flat inflorescences and oblong leaves at maturity.

EXAMPLE 10

Determination of Functional Homolog Sequences

The "Lead" sequences described in above Examples are utilized to identify functional homologs of the lead sequences and, together with those sequences, are utilized to determine a consensus sequence for a given group of lead and functional homolog sequences.

A subject sequence is considered a functional homolog of a query sequence if the subject and query sequences encode proteins having a similar function and/or activity. A process known as Reciprocal BLAST (Rivera et al, *Proc. Natl Acad. Sci. USA,* 1998, 95:6239-6244) is used to identify potential functional homolog sequences from databases consisting of all available public and proprietary peptide sequences, including NR from NCBI and peptide translations from Ceres clones.

Before starting a Reciprocal BLAST process, a specific query polypeptide is searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides are designated as a cluster.

The main Reciprocal BLAST process consists of two rounds of BLAST searches; forward search and reverse search. In the forward search step, a query polypeptide sequence, "polypeptide A," from source species $S^A$ is BLASTed against all protein sequences from a species of interest. Top hits are determined using an E-value cutoff of 10-5 and an identity cutoff of 35%. Among the top hits, the sequence having the lowest E-value is designated as the best hit, and considered a potential functional homolog. Any other top hit that had a sequence identity of 80% or greater to the best hit or to the original query polypeptide is considered a potential functional homolog as well. This process is repeated for all species of interest.

In the reverse search round, the top hits identified in the forward search from all species are used to perform a BLAST search against all protein or polypeptide sequences from the source species $S^A$. A top hit from the forward search that returned a polypeptide from the aforementioned cluster as its best hit is also considered as a potential functional homolog.

Functional homologs are identified by manual inspection of potential functional homolog sequences. Representative functional homologs are shown in FIG. 1. The Figure represents a grouping of a lead/query sequence aligned with the corresponding identified functional homolog subject sequences. Lead sequences and their corresponding functional homolog sequences are aligned to identify conserved amino acids and to determine a consensus sequence that contains a frequently occurring amino acid residue at particular positions in the aligned sequences, as shown in FIG. 1.

Each consensus sequence then is comprised of the identified and numbered conserved regions or domains, with some of the conserved regions being separated by one or more amino acid residues, represented by a dash (-), between conserved regions.

Useful polypeptides of the inventions, therefore, include each of the lead and functional homolog sequences shown in FIG. 1, as well as the consensus sequences shown in the Figure. The invention also encompasses other useful polypeptides constructed based upon the consensus sequence and the identified conserved regions. Thus, useful polypeptides include those which comprise one or more of the numbered conserved regions in each alignment table in FIG. 1, wherein the conserved regions may be separated by dashes. Useful polypeptides also include those which comprise all of the numbered conserved regions in FIG. 1, alternatively comprising all of the numbered conserved regions in an individual alignment table and in the order as depicted in FIG. 1. Useful polypeptides also include those which comprise all of the numbered conserved regions in the alignment table and in the order as depicted in FIG. 1, wherein the conserved regions are separated by dashes, wherein each dash between two adjacent conserved regions is comprised of the amino acids depicted in the alignment table for lead and/or functional homolog sequences at the positions which define the particular dash. Such dashes in the consensus sequence can be of a length ranging from length of the smallest number of dashes in one of the aligned sequences up to the length of the highest number of dashes in one of the aligned sequences.

Such useful polypeptides can also have a length (a total number of amino acid residues) equal to the length identified for a consensus sequence or of a length ranging from the shortest to the longest sequence in any given family of lead and functional homolog sequences identified in FIG. 1.

The present invention further encompasses nucleotides that encode the above described polypeptides, as well as the complements thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

TABLE 2 summarizes the sequences found in FIG. 1.

Each of the references from the patent and periodical literature cited herein is hereby expressly incorporated in its entirety by such citation.

TABLE 2

| FUNCTIONAL HOMOLOG ID | % IDENTITY | E-VALUE | SPECIES | SEQ_ID_NO |
|---|---|---|---|---|
| QUERY HOMOLOG ID: CeresClone 519 SEQ ID NO 87 | | | | |
| 663844 | 76.00 | 3.30E-30 | *Glycine max* | SEQ ID NO 99 |
| 703180 | 72.70 | 9.19E-26 | Triticum aestivum | SEQ ID NO 102 |
| 945972 | 69.80 | 4.60E-24 | Brassica napus | SEQ ID NO 103 |
| 22331645 | 69.50 | 3.00E-27 | Arabidopsis thaliana | SEQ ID NO 106 |
| 31431968 | 65.80 | 1.99E-16 | Oryza sativa subsp. *japonica* | SEQ ID NO 109 |
| 50912765 | 58.50 | 2.49E-16 | Oryza sativa subsp. *japonica* | SEQ ID NO 110 |
| 486120 | 53.57 | 1.20E-16 | Zea mays | SEQ ID NO 111 |
| 503296 | 55.42 | 2.50E-16 | Zea mays | SEQ ID NO 112 |

TABLE 2-continued

| FUNCTIONAL HOMOLOG ID | % IDENTITY | E-VALUE | SPECIES | SEQ_ID_NO |
|---|---|---|---|---|
| QUERY HOMOLOG ID: CeresClone 4734 SEQ ID NO 85 | | | | |
| 663844 | 69.60 | 2.49E−23 | Glycine max | SEQ ID NO 99 |
| 703180 | 76.60 | 1.09E−29 | Triticum aestivum | SEQ ID NO 102 |
| 945972 | 68.60 | 1.60E−21 | Brassica napus | SEQ ID NO 103 |
| 22331645 | 64.40 | 3.70E−22 | Arabidopsis thaliana | SEQ ID NO 106 |
| 31431968 | 51.10 | 1.49E−16 | Oryza sativa subsp. *japonica* | SEQ ID NO 109 |
| 50912765 | 53.40 | 2.80E−17 | Oryza sativa subsp. *japonica* | SEQ ID NO 110 |
| 486120 | 54.65 | 1.50E−18 | Zea mays | SEQ ID NO 111 |
| 503296 | 50.59 | 9.40E−17 | Zea mays | SEQ ID NO 112 |
| QUERY HOMOLOG ID: CeresClone 8607 SEQ ID NO 97 | | | | |
| 663844 | 67.40 | 5.29E−23 | Glycine max | SEQ ID NO 99 |
| 703180 | 75.50 | 4.79E−29 | Triticum aestivum | SEQ ID NO 102 |
| 945972 | 68.60 | 4.69E−22 | Brassica napus | SEQ ID NO 103 |
| 1449794 | 73.80 | 5.69E−26 | Populus balsamifera subsp. *trichocarpa* | SEQ ID NO 107 |
| 1468218 | 67.80 | 4.09E−23 | Populus balsamifera subsp. *trichocarpa* | SEQ ID NO 100 |
| 1530225 | 75.00 | 2.10E−26 | Populus balsamifera subsp. *trichocarpa* | SEQ ID NO 104 |
| 22331645 | 63.60 | 9.79E−22 | Arabidopsis thaliana | SEQ ID NO 106 |
| 31431968 | 50.60 | 2.49E−16 | Oryza sativa subsp. *japonica* | SEQ ID NO 109 |
| 50912765 | 52.90 | 1.49E−16 | Oryza sativa subsp. *japonica* | SEQ ID NO 110 |
| 78708592 | 56.80 | 7.09E−19 | Oryza sativa subsp. *japonica* | SEQ ID NO 98 |
| 486120 | 48.61 | 5.40E−14 | Zea mays | SEQ ID NO 111 |
| 503296 | 50.59 | 9.40E−17 | Zea mays | SEQ ID NO 112 |
| QUERY HOMOLOG ID: CeresClone 336524 SEQ ID NO 83 | | | | |
| 663844 | 64.80 | 1.70E−17 | Glycine max | SEQ ID NO 99 |
| 703180 | 64.90 | 9.99E−20 | Triticum aestivum | SEQ ID NO 102 |
| 945972 | 56.50 | 3.70E−15 | Brassica napus | SEQ ID NO 102 |
| 22331645 | 54.60 | 1.09E−15 | Arabidopsis thaliana | SEQ ID NO 106 |
| 31431968 | 84.30 | 1.60E−28 | Oryza sativa subsp. *japonica* | SEQ ID NO 109 |
| 50912765 | 73.20 | 3.99E−25 | Oryza sativa subsp. *japonica* | SEQ ID NO 110 |
| 486120 | 67.82 | 1.10E−24 | Zea mays | SEQ ID NO 111 |
| 503296 | 77.50 | 4.40E−26 | Zea mays | SEQ ID NO 112 |
| QUERY HOMOLOG ID: CeresClone 560681 SEQ ID NO 89 | | | | |
| 663844 | 80.60 | 6.99E−28 | Glycine max | SEQ ID NO 99 |
| 703180 | 100.00 | 5.79E−40 | Triticum aestivum | SEQ ID NO 102 |
| 945972 | 73.80 | 3.99E−25 | Brassica napus | SEQ ID NO 103 |
| 22331645 | 64.70 | 4.30E−21 | Arabidopsis thaliana | SEQ ID NO 106 |
| 31431968 | 62.30 | 1.29E−19 | Oryza sativa subsp. *japonica* | SEQ ID NO 109 |
| 50912765 | 60.40 | 4.90E−20 | Oryza sativa subsp. *japonica* | SEQ ID NO 110 |
| 486120 | 59.77 | 1.20E−18 | Zea mays | SEQ ID NO 111 |
| 503296 | 56.47 | 2.10E−19 | Zea mays | SEQ ID NO 112 |
| QUERY HOMOLOG ID: CeresClone 560948 SEQ ID NO 91 | | | | |
| 663844 | 77.70 | 3.90E−27 | Glycine max | SEQ ID NO 99 |
| 703180 | 89.00 | 4.39E−35 | Triticum aestivum | SEQ ID NO 102 |
| 945972 | 71.90 | 5.90E−24 | Brassica napus | SEQ ID NO 103 |
| 22331645 | 64.40 | 3.30E−21 | Arabidopsis thaliana | SEQ ID NO 106 |
| 31431968 | 60.00 | 6.39E−18 | Oryza sativa subsp. *japonica* | SEQ ID NO 109 |
| 50912765 | 59.30 | 1.90E−18 | Oryza sativa subsp. *japonica* | SEQ ID NO 110 |
| 486120 | 58.62 | 6.40E−18 | Zea mays | SEQ ID NO 111 |
| 503296 | 56.32 | 1.30E−17 | Zea mays | SEQ ID NO 112 |
| QUERY HOMOLOG ID: CeresClone 653656 SEQ ID NO 93 | | | | |
| 663844 | 96.70 | 8.60E−39 | Glycine max | SEQ ID NO 99 |
| 703180 | 81.80 | 1.29E−28 | Triticum aestivum | SEQ ID NO 102 |
| 945972 | 76.80 | 8.29E−25 | Brassica napus | SEQ ID NO 103 |
| 1449794 | 79.50 | 1.70E−26 | Populus balsamifera subsp. *trichocarpa* | SEQ ID NO 107 |
| 1468218 | 87.90 | 6.40E−34 | Populus balsamifera subsp. *trichocarpa* | SEQ ID NO 100 |
| 1530225 | 80.60 | 8.10E−27 | Populus balsamifera subsp. *trichocarpa* | SEQ ID NO 104 |
| 22331645 | 72.50 | 1.29E−26 | Arabidopsis thaliana | SEQ ID NO 106 |
| 31431968 | 64.10 | 8.20E−18 | Oryza sativa subsp. *japonica* | SEQ ID NO 109 |
| 50912765 | 60.70 | 5.00E−18 | Oryza sativa subsp. *japonica* | SEQ ID NO 110 |
| 78708592 | 73.80 | 1.49E−25 | Oryza sativa subsp. *japonica* | SEQ ID NO 98 |
| 486120 | 60.87 | 8.70E−14 | Zea mays | SEQ ID NO 111 |
| 503296 | 59.04 | 9.10E−19 | Zea mays | SEQ ID NO 112 |
| QUERY HOMOLOG ID: CeresClone 733804 SEQ ID NO 95 | | | | |
| 663844 | 78.80 | 1.49E−27 | Glycine max | SEQ ID NO 99 |
| 703180 | 72.20 | 4.39E−26 | Triticum aestivum | SEQ ID NO 102 |
| 945972 | 71.70 | 1.39E−24 | Brassica napus | SEQ ID NO 103 |
| 1449794 | 70.00 | 1.70E−24 | Populus balsamifera subsp. *trichocarpa* | SEQ ID NO 107 |
| 1468218 | 74.40 | 3.00E−27 | Populus balsamifera subsp. *trichocarpa* | SEQ ID NO 100 |
| 1530225 | 71.10 | 6.50E−25 | Populus balsamifera subsp. *trichocarpa* | SEQ ID NO 104 |

TABLE 2-continued

| FUNCTIONAL HOMOLOG ID | % IDENTITY | E-VALUE | SPECIES | SEQ_ID_NO |
|---|---|---|---|---|
| 22331645 | 71.10 | 3.60E−24 | Arabidopsis thaliana | SEQ ID NO 106 |
| 31431968 | 64.20 | 8.79E−21 | Oryza sativa subsp. *japonica* | SEQ ID NO 109 |
| 50912765 | 62.70 | 4.90E−20 | Oryza sativa subsp. *japonica* | SEQ ID NO 110 |
| 78708592 | 82.20 | 2.50E−32 | Oryza sativa subsp. *japonica* | SEQ ID NO 98 |
| 486120 | 57.75 | 9.70E−15 | Zea mays | SEQ ID NO 111 |
| 503296 | 57.47 | 1.70E−19 | Zea mays | SEQ ID NO 112 |

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J.* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981) *Adv. App. Math.* 2:482.
(9) Needleman and Wunsch (1970) *J. Mol. Biol.* 48:443.
(10) Pearson and Lipman (1988) *Proc. Natl. Acad. Sci. (USA)* 85: 2444.
(11) Yamauchi et al. (1996) *Plant Mol. Biol.* 30:321-9.
(12) Xu et al. (1995) *Plant Mol. Biol.* 27:237.
(13) Yamamoto et al. (1991) *Plant Cell* 3:371.
(14) P. Tijessen, "Hybridization with Nucleic Acid Probes" In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., Molecular Cloning: A Laboratory Manual, Second Edition, Cold Spring Harbor Laboratory Press, 1989, New York.
(17) Shizuya et al. (1992) *Proc. Natl. Acad. Sci. USA,* 89: 8794-8797.
(18) Hamilton et al. (1996) *Proc. Natl. Acad. Sci. USA,* 93: 9975-9979.
(19) Burke et al. (1987) *Science,* 236:806-812.
(20) Sternberg N. et al. (1990) *Proc Natl Acad Sci USA.,* 87:103-7.
(21) Bradshaw et al. (1995) *Nucl Acids Res,* 23: 4850-4856.
(22) Frischauf et al. (1983) *J. Mol Biol,* 170: 827-842.
(23) Huynh et al., Glover N. Mex. (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J* 28:455.
(28) Weising et al. (1988) *Ann. Rev. Genet.,* 22:421.
(29) Christou (1995) *Euphytica,* v. 85, n. 1-3:13-27.
(30) Newell (2000)
(31) Griesbach (1987) *Plant Sci* 50:69-77.
(32) Fromm et al. (1985) *Proc. Natl. Acad. Sci. USA* 82:5824.
(33) Paszkowski et al. (1984) *EMBO J.* 3:2717.
(34) Klein et al. (1987) *Nature* 327:773.
(35) Willmitzer, L. (1993) Transgenic Plants. In: Iotechnology, A Multi-Volume Comprehensive Treatise (H. J. Rehm, G. Reed, A. Püler, P. Stadler, eds., Vol. 2, 627-659, VCH Weinheim-New York-Basel-Cambridge).
(36) *Crit. Rev. Plant. Sci.* 4:146.
(37) Fromm et al. (1990) *Biotechnology* 8:833-844.
(38) Cho et al. (2000) *Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), "Genetically Engineered Viruses" (C. J. A. Ring and E. D. Blair, Eds). Pp. 59-99, BIOS Scientific Publishers, Ltd. Oxford, UK.

What is claimed is:

1. A method of increasing size, vegetative growth, photosynthetic capacity, biomass or seedling vigor of a plant grown in low nitrate conditions, said method comprising:
   (a) introducing into a plant cell an isolated nucleic acid molecule comprising a nucleotide sequence that encodes an amino acid sequence that is at least 95% identical to the amino acid sequence set forth in SEQ ID NO: 95;
   (b) generating from said plant cell a transformed plant in which said nucleic acid molecule is overexpressed; and
   (c) selecting from a plurality of said transformed plants a transformed plant having at least one characteristics selected from the group consisting of increased size, increased vegetative growth, increased seedling vigor, increased photosynthetic capacity and increased biomass when grown in low nitrate conditions as compared to a control plant grown under the same conditions.

2. The method of claim 1, wherein said isolated nucleic acid is operably linked to a regulatory region.

3. The method of claim 2, wherein said regulatory region is a promoter selected from the group consisting of YP0092 (SEQ ID NO: 38), PT0676 (SEQ ID NO: 12), PT0708 (SEQ ID NO: 17), PT0613 (SEQ ID NO: 5), PT0672 (SEQ ID NO: 11), PT0678 (SEQ ID NO: 13), PT0688 (SEQ ID NO: 15), PT0837 (SEQ ID NO: 24), a napin promoter, an Arcelin-5 promoter, a phaseolin gene promoter, a soybean trypsin inhibitor promoter, an ACP promoter, a stearoyl-ACP desaturase gene promoter, a soybean α' subunit of β-conglycinin promoter, a 15 kD zein promoter, a 16 kD zein promoter, a 19 kD zein promoter, a 22 kD zein promoter, a 27 kD zein promoter, an Osgt-1 promoter, a beta-amylase gene promoter, and a barley hordein gene promoter.

4. The method of claim 2, wherein said regulatory region is a promoter selected from the group consisting of p326 (SEQ ID NO: 76), YP0144 (SEQ ID NO: 55), YP0190 (SEQ ID NO: 59), p13879 (SEQ ID NO: 75), YP0050 (SEQ ID NO: 35), p32449 (SEQ ID NO: 77), 21876 (SEQ ID NO: 1), YP0158 (SEQ ID NO: 57), YP0214 (SEQ ID NO: 61), YP0380 (SEQ ID NO: 70), PT0848 (SEQ ID NO: 26), PT0633 (SEQ ID NO:7), a cauliflower mosaic virus (CaMV) 35S promoter, a mannopine synthase (MAS) promoter, 1' or 2' promoters derived from T-DNA of *Agrobacterium tumefaciens*, a figwort mosaic virus 34S promoter, a rice actin promoter, and a maize ubiquitin-1 promoter.

5. The method of claim 2, wherein said regulatory region is a promoter selected from the group consisting of ribulose-1,5-bisphosphate carboxylase (RbcS) promoters, a pine cab6 promoter, a Cab-1 gene promoter from wheat, a CAB-1 promoter from spinach, a cab 1R promoter from rice, a pyruvate orthophosphate dikinase (PPDK) promoter from corn, a tobacco Lhcb1*2 promoter, an *Arabidopsis thaliana* SUC2 sucrose-H+ symporter promoter, thylakoid membrane protein promoters from spinach, PT0535 (SEQ ID NO: 3), PT0668 (SEQ ID NO: 2), PT0886 (SEQ ID NO: 29), PR0924 (SEQ ID NO: 78), YP0144 (SEQ ID NO: 55), YP0380 (SEQ ID NO: 70) and PT0585 (SEQ ID NO: 4).

6. A method for promoting increased biomass in a plant grown in low nitrate conditions, said method comprising:
   (a) transforming a plant cell with a nucleic acid molecule comprising a nucleotide sequence encoding an amino acid sequence that is at least 95% identical to the sequence set forth in SEQ ID NO: 95;
   (b) regenerating from said plant cell a transformed plant in which said nucleic acid molecule is overexpressed; and
   (c) selecting from a plurality of said transformed plants a transformed plant having an increased biomass as compared to a plant that has not been transformed with said nucleotide sequence and is grown under the same conditions.

7. A method for increasing biomass of a plant grown in low nitrate conditions, said method comprising:
   a) introducing into a plant cell a vector construct comprising
      a first nucleic acid molecule that is a regulatory sequence which causes transcription in a plant; and
      a second nucleic acid molecule encoding an amino acid sequence that is at least 95% identical to the sequence set forth in SEQ ID NO: 95, wherein said first and second nucleic acid molecules are operably linked;
   b) regenerating from said plant cell a transformed plant in which said second nucleic acid molecule is overexpressed; and
   c) selecting from a plurality of said transformed plants a transformed plant having increased biomass when grown in low nitrate conditions as compared to a control plant that does not comprise said overexpressed nucleic acid and is grown under the same conditions.

8. A method of modulating architecture of a plant grown in low nitrate conditions, said method comprising:
   (a) introducing into a plant cell an isolated nucleic acid molecule comprising a nucleotide sequence that encodes an amino acid sequence that is at least 95% identical to the amino acid sequence set forth in SEQ ID NO: 95;
   (b) regenerating from said plant cell a transformed plant in which said nucleic acid molecule is overexpressed; and
   (c) selecting from a plurality of said transformed plants a transformed plant having modulated plant architecture when grown in low nitrate conditions as compared to a control plant grown under the same conditions.

9. The method of claim 8, wherein said modulated plant architecture has at least one characteristics selected from the group consisting of flat inflorescences, elongated hypocotyls, elongated rosette leaves and flat bolts.

10. The method of any one of claims 1, 6 and 8, wherein said isolated nucleic acid molecule comprises a nucleotide sequence that encodes an amino acid sequence that is at least 96% identical to the amino acid sequence set forth in SEQ ID NO: 95.

11. The method of any one of claims 1, 6 and 8, wherein said isolated nucleic acid molecule comprises a nucleotide sequence that encodes an amino acid sequence that is at least 97% identical to the amino acid sequence set forth in SEQ ID NO: 95.

12. The method of any one of claims 1, 6 and 8, wherein said isolated nucleic acid molecule comprises encodes the amino acid sequence set forth in SEQ ID NO: 95.

13. The method of claim 1, wherein said photosynthetic capacity is increased.

14. The method of claim 8, wherein said isolated nucleic acid is operably linked to a regulatory region.

* * * * *

SEQUENCE LISTING

```
<160> NUMBER OF SEQ ID NOS: 112

<210> SEQ ID NO 1
<211> LENGTH: 1823
<212> TYPE: DNA
<213> ORGANISM: Arabidopsis thaliana
<220> FEATURE:
<221> NAME/KEY: misc_feature
<222> LOCATION: (1)..(1823)
<223> OTHER INFORMATION: Ceres Promoter 21876

<400> SEQUENCE: 1
gtctcttaaa aaggatgaac aaacacgaaa ctggtggatt atacaaatgt cgccttatac        60
atatatcggt tattggccaa aagagctatt ttaccttatg gataatggtg ctactatggt       120
tggagttgga ggtgtagttc aggcttcacc ttctggttta agccctccaa tgggtaatgg       180
taaatttccg gcaaaaggtc ctttgagatc agccatgttt tccaatgttg aggtcttata       240
ttccaagtat gagaaaggta aaataaatgc gtttcctata gtggagttgc tagatagtag       300
```

```
tagatgttat gggctacgaa ttggtaagag agttcgattt tggactagtc cactcggata    360
cttttttcaat tatggtggtc ctggaggaat ctcttgtgga gtttgatatt tgcgagtata   420
atctttgaac ttgtgtagat tgtacccaaa accgaaaaca tatcctatat aaatttcatt    480
atgagagtaa aattgtttgt tttatgtatc atttctcaac tgtgattgag ttgactattg    540
aaaacatatc ttagataagt ttcgttatga gagttaatga tgattgatga catacacact    600
cctttatgat ggtgattcaa cgttttggag aaaatttatt tataatctct cataaattct    660
ccgttattag ttgaataaaa tcttaaatgt ctcctttaac catagcaaac caacttaaaa    720
atttagattt taaagttaag atggatattg tgattcaacg attaattatc gtaatgcata    780
ttgattatgt aaaataaaat ctaactaccg gaatttattc ataactcca ttgtgtgact     840
gcatttaaat atatgtttta tgtcccatta attaggctgt aatttcgatt tatcaattta    900
tatactagta ttaatttaat tccatagatt tatcaaagcc aactcatgac ggctagggtt    960
ttccgtcacc ttttcgatca tcaagagagt tttttttataa aaaatttat acaattatac   1020
aatttcttaa ccaaacaaca cataattata agctatttaa catttcaaat tgaaaaaaaa   1080
aatgtatgag aattttgtgg atccatttt gtaattcttt gttgggtaaa ttcacaacca    1140
aaaaaataga aaggcccaaa acgcgtaagg gcaaattagt aaaagtagaa ccacaaagag   1200
aaagcgaaaa ccctagacac ctcgtagcta taagtaccct cgagtcgacc aggattaggg   1260
tgcgctctca tatttctcac atttttcgtag ccgcaagact cctttcagat tcttacttgc  1320
aggttagata ttttctctct ttagtgtctc cgatcttcat cttcttatga ttattgtagc   1380
tgtttagggt ttagattctt agttttagct ctatattgac tgtgattatc gcttattctt   1440
tgctgttgtt atactgcttt tgattctcta gctttagatc cgtttactcg tcgatcaata   1500
ttgttcctat tgagtctgat gtataatcct ctgattaatt gatagcgttt agttttgata   1560
tcgtcttcgc atgttttttta tcatgtcgat ctgtatctgc tctggttata gttgattctg   1620
atgtatttgg ttggtgatgt tccttagatt tgatatacct gttgtctcgt ggtttgatat   1680
gatagctcaa ctggtgatat gtggttttgt ttcagtggat ctgtgtttga ttatattgtt   1740
gacgttttgg ttgttgtatg gttgatggtt gatgtatttt tgttgattct gatgtttcga   1800
ttttttgttttt tgttttgaca gct                                          1823

<210> SEQ ID NO 2
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0668

<400> SEQUENCE: 2
atagagtttt actatgcttt tggaatcttt cttctaatgt gccaactaca gagaaataca     60
tgtattacca ctaggaatcg gaccatatca tagatatcag gattagataa ctagttctcg    120
tcgctatcac ttcgcattaa gttctagtaa ttgttaaaga ttctaatttt ttactaaaca    180
aaaactaaat caacatcaaa tatgcaaagt gtgtgttgtc cacacaagtg actcaaagta    240
tacgcaggtg ggattggacc atattattgc aaatcgtttc cgaaccactc atatttcttt    300
ttttctctcc ttttttttatc cggagaatta tggaaccact tcatttcaac ttcaaaacta    360
attttttggt tcagtgatca aatacaaaaa aaaaaaaaaa gttatagata ttaaatagaa    420
aactattcca atcttaaaaa tacaaatgaa accataattt taatttatac aaaactatttt   480
```

```
aattagctaa gggttgtctt aacgtttaga aaataaaaaa ttatgattgt ctgtttaaaa      540
ttacaatgaa tgaataaaaa aaatatgcaa tgaatgaaag ataaaatttt gtacatccga      600
tagaatgaga aaatgaattt tgtacaaacc actcaagaat tcaaaacaat tgtcaaagtt      660
ttcttctcag ccgtgtgtcc tcctctccta gccgccacat ctcacacact aatgctaacc      720
acgcgatgta accgtaagcg ctgagttttt gcatttcaga tttcacttcc accaaacaaa      780
actcgccacg tcatcaatac gaatcattcc gtataaacgt ctagattctt tacagcctac      840
aatgttctct tctttggtcg gccattattt aacgctttga acctaaatct agcccagcca      900
acgaagaaga cgaagcaaat ccaaaccaaa gttctccatt tcgtagcttc ctttaagctt      960
tttcagtatc atagagacac ttttttttt ttgattagaa                             1000
```

<210> SEQ ID NO 3
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0535

<400> SEQUENCE: 3

```
ttagtgaaat tatgcacatta agtaaggttt tcttagttag ctaatgtatg gctattcaat      60
tgttatgtta ggctattta gttagtatat gaatttaggc agtctatgca aatgatttcg      120
ttttcatttt ttcatatgta aacatcaaga tcaagtaacg ccattcgagt tgatatttt      180 tttttaaatt agtgtgtgta aattttggac cgcttatttg agtttgctaa tgaagttgca     240
tatatattac gttaaaccat aggcaaacta atttgaaaca tccgattcga tttcctgtaa      300
tttttcttgg ttaattgacc aaaatcaaga tcttcagaaa taaaataaaa gacgaaagaa      360
agctgtcgca aagcagattg tgttaaaaaa aagtggattg ggctcaaacg caacttgtcc      420
agcccgtgac aattacccta tacgcaagta agagtaacgt atcactggca aaagttggta     480
ttagttacga tatctttgtc atgggggcat gcatgggcat ggcttaagag ttaagcctta      540
agaagagtcc cacactcgtg actctcatga tcacttgttg tttcttacgg gcaaatacat      600
ttaactttat tcttcattta ttcacctata ttctttttgga taataacttt tctctatata    660
aaataacaaa catcgtacgt ttcatttatt tacaacaagc gatgagaatt aaaaggagac      720
cttaattgat gatactcttc ttttctctcg gttacaacgg gattattaca gataatgata      780
atctatatgg atgctgacgt ggaaaaacaa aatttggtga aacacgtcaa ttaagcacga      840
cttttccatg gctagtggct aagatcgttt catcacatgg ctatatcata taatacttgg      900
atgaattcaa aataaacgac tgagaaaatg tccacgtcac ggcgcaccgc tttggactta      960
agtctcctat aataaataca acaccaaaca ttgcattcca                            1000
```

<210> SEQ ID NO 4
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0585

<400> SEQUENCE: 4

```
tgaagtcatt taatatgagt ttgacattag gtaaacctaa tctatgagat tatagaatgt      60
agcaaaacta tcaatgtttc ttttccaaaa tattttgtgg ttttttctttt tggttcatta   120
```

```
tgttttgtta tttgtgaatt attttaatat gaagtaatta tattgatttt atatgatata      180
catattattt tgatataaaa tttaacactt atccattaaa atagcatggg cataatcaaa      240
atcgggacta ttacgatgaa aaagatagtt aaattgtatg ataaaataaa atgtgtaaga     300
ttaaaatttt gggttttaga aaattactaa acaaaatata gacaaagtat gttgactatt      360
atttaaaatt taaatatcat caataagata tagttaaagt cattaagtgt atagcaaaat     420
gaaaattcta agattaaaat tcgattaaaa ttttttttac taaattaaat attttaaaaat    480 agggattatc atttactatt tacaattcta atatcatggg taaaaattga taacttttttt   540 taaacccgcc tatctaggtg ggcctaacct agtttactaa ttactatatg attaacttat     600
taccactttt acttcttctt ttttggtcaa attactttat tgttttttat aaagtcaaat      660
tactctttgc attgtaaata atagtagtaa ctaaaatctt aaaacaaaat attcaacctt      720
tcccattatt ggaatggtaa tgtcttcaac accattgacc aacgttaagg aatgtctttt      780 aatattttttg gaacctaaat gctaatactg tataccacaa tcacttatga gtattgaagt    840
tgagatagag gaggtacaag gagaccttat ctgcagaaga caaaaagcca ttttttagcaa    900 aactaaagaa agaaaaaaga ttgaaacaca aatatgcgcc actcgtagtc caccccctatc  960 tctttggcaa aagccacttc actctttttc ccttttttat                           999

<210> SEQ ID NO 5
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0613

<400> SEQUENCE: 5
ttaatactaa cattgtagaa agccacaaaa aagaaattga aatgtgagta gatgctgagt      60
cagaggtttg gtcaatacac aacagctaat tgagataata ttatacacgt cacgatgact     120
tgttttttct cctcccaact tgttaatttc tttattctta aaattaaacc atcgcaaaaa     180
cagaagaaca cagctgtttt tctcgactcc caatttctat tttgctgcta aggacatttc     240
atttcattat ttcccaattc aggactcctt agattttcct aaatttgttt tcctaacttg     300
ctctctctca ttctaacatt ttctcatttt tttagattat cttgtacttt ttagtagatt     360
attttatcag gttttacaaa catacattga cattctaaaa agggcttcta aaaattcagt     420
gtggaatgct gatatactaa aaaaaggtca tgcaaaatta tctacgattt atctaaaatt     480
agataatttg ccatatataa ctattaacta ataatcgatc ctttgatttt ttgtttagat     540
aaaacgaaac agctatatct tttttttttg ttatcggatt ttaatcgaat aaaagctgaa     600
aaataacagt tatatcttct tctttttttaa ctaatgaaac agttatatct taaacaaaca    660
acagaaacag taaatatatta atgcaaatcc gcgtcaagag ataaattttta acaaactaat   720 aacaattgag ataagattag cgcaaaagaa actctaatttt tagagcgtgt aaacacaaac   780
acgtcttgaa agtaaacgtg aattacacgc ttctaaaacg agcgtgagtt ttggttataa    840
cgaagatacg gtgaagtgtg acaccttttct acgttaattt cagtttgagg acacaactca   900
agttatgttt gatatctaag gacttgcact gtctccaaat ctgcaggaag gacttttttga  960 ttggatcaat ataaataacca tctccattct cgtctccttc                         1000
```

```
<210> SEQ ID NO 6
<211> LENGTH: 351
<212> TYPE: DNA
<213> ORGANISM: Arabidopsis thaliana
<220> FEATURE:
<221> NAME/KEY: misc_feature
<222> LOCATION: (1)..(351)
<223> OTHER INFORMATION: Ceres Promoter PT0625

<400> SEQUENCE: 6
gatcatgatc agtttcaact cgctgtgccc acgtgtcgag agatcggcac gtgcctgagc      60
tctcagccgc tcataaatac acttgtttag tagcaacagt atactatagt agtcctctcc     120
tgtttggctt ttagcttgca tcgatggatg gatggatgga tcgcatgaga gggcttcgcg     180
aaggtacgga accttacaca acgcgtgtcc tttctacgtg gccatcgtgt aggcgtctcg     240
ccatgctacg tgtcccggag gatgtctcga tgccaacccct tataaatact gttccattcc     300
aatcccatcg ccacagccag tgcaaatctg atcgatcaag ataatcgagc a              351

<210> SEQ ID NO 7
<211> LENGTH: 1022
<212> TYPE: DNA
<213> ORGANISM: Arabidopsis thaliana
<220> FEATURE:
<221> NAME/KEY: misc_feature
<222> LOCATION: (1)..(1022)
<223> OTHER INFORMATION: Ceres Promoter PT0633

<400> SEQUENCE: 7
cccgatcggc cttaatctga gtcctaaaaa ctgttatact taacagttaa cgcatgattt      60
gatggaggag ccatagatgc aattcaatca aactgaaatt tctgcaagaa tctcaaacac     120
ggagatctca aagtttgaaa gaaaatttat ttcttcgact caaaacaaac ttacgaaatt     180
taggtagaac ttatatacat tatattgtaa ttttttgtaa caaaatgttt ttattattat     240
tatagaattt tactggttaa attaaaaatg aatagaaaag gtgaattaag aggagagagg     300
aggtaaacat tttcttctat tttttcatat tttcaggata aattattgta aaagtttaca     360
agatttccat ttgactagtg taaatgagga atattctcta gtaagatcat tatttcatct     420
acttctttta tcttctacca gtagaggaat aaacaatatt tagctccttt gtaaatacaa     480
attaattttc gttcttgaca tcattcaatt ttaattttac gtataaaata aaagatcata     540
cctattagaa cgattaagga gaaatacaat tcgaatgaga aggatgtgcc gtttgttata     600
ataaacagcc acacgacgta aacgtaaaat gaccacatga tgggccaata gacatggacc     660
gactactaat aatagtaagt tacattttag gatggaataa atatcatacc gacatcagtt     720
tgaaagaaaa gggaaaaaaa gaaaaaataa ataaaagata tactaccgac atgagttcca     780
aaaagcaaaa aaaagatca agccgacaca gacacgcgta gagagcaaaa tgactttgac     840
gtcacaccac gaaaacagac gcttcatacg tgtccctta tctctctcag tctctctata     900
aacttagtga gaccctcctc tgttttactc acaaatatgc aaactagaaa acaatcatca     960
ggaataaagg gtttgattac ttctattgga aagaaaaaaa tctttggaaa aggcctgcag    1020
gg                                                                    1022

<210> SEQ ID NO 8
<211> LENGTH: 1000
<212> TYPE: DNA
<213> ORGANISM: Arabidopsis thaliana
```

```
<220> FEATURE:
<221> NAME/KEY: misc_feature
<222> LOCATION: (1)..(1000)
<223> OTHER INFORMATION: Ceres Promoter PT0650

<400> SEQUENCE: 8
catacttaat tctaaaaaaa caacacttat agtttataag cagctcttat gataaaaatc      60
tttctgagtt atagctctgt taaacttgta ttcaccccaa aaacggatgt ttcatttctt     120
attttttact tggagtattt tattgtaatt tgtaaaaaaa aatgtaaagt gggggatatc     180
atgaaaaaca acgtcacttt gtttggtcac aatatacatt tgataaaata atggtcgtcg     240
cgtgatttag ttgattttg ttttatcaac cacgtgtttc acttgatgag tagtttatat      300
agttaacatg attcggccac ttcagatttg ggtttgccca catatgacat accgacatag     360
aaggttaaat ccacgtggga aatgccaata ttcaatgttt ggttttcaaa agagaatcat     420
ttctttatat gatctcaaaa gtatggaatt gaaatgacta atgagcacat gcaattggtg     480
ctatcttaaa aaccgaacgt ctttgaattt aatttgtttt tcaccaaagg tacctaatga     540 aacccttca ttaaaaaata aaggtaacaa acaaaatttt gtattggaaa aaacattttt      600
tggaatatat aatttggtaa tagaattatg agcaaaaaag aaaagaaaa gaaagaataa      660 tgagcataat aaagccttta cagtattact aattgggccg agcagttttg ggctcttgat     720
catgtctagt aatcttaaac agacgataaa gttaactgca atttagttgg ttcaggtgag     780
ctaccaaatc caaaaatacg cagattaggt tcaccgtacc ggaacaaacc ggatttatca     840
aaatccttaa gttatacgaa atcacgcttt tccttcgatt tctccgctct tctccactct     900
tcttctctgt tctatcgcag acattttgt ttatatgcat acataataat aatacactct      960
tgtcaggatt tttgattctc tctttggttt tctcggaaaa                          1000

<210> SEQ ID NO 9
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0660

<400> SEQUENCE: 9
caagtcaagt tccaatattc taaggagaaa taatagtata ctaaacatac attagagagg      60
ttaaacttct ttttggatt aagtgtgtat gcataggcta tttattctta agtataacta     120
ttaactgtag ctagatttat acaagaaata cataaaactt tatgcatgtg aggtagccat     180
gaatatacgt acatgttgca atcgattata catgttgtat ttggatttct ctatacatgt     240
tttaacttgt cattctctaa gtatatacat accattaata ctgtgggcat gagtttatga     300
taagactttt cttttggaga ccagttttgt tttcctttcc acctatattt gtctataggc     360
ttcacggtac actagtttac aagtgttttt atatgttcta aataaaattg agattttccg     420
gaacggtatg atctgtttgc aaataaggac gtatatataa cagtatcaaa tatatttgtt     480
gttataaggc aataatatat tttctgagat attgcgtgtt acaaaaaga aatatttgtt      540 aagaaaaaaa aagatggtcg aaaaagggga gtaggtgggg gcggtcggct tttgattagt     600
aataaaagaa accacacgag tgacctaccg attcgactca acgagtctac cgagctaaca     660
cagattcaac tcgctcgagc ttcgttttat gacaagttgg tttttttttt ttttttaat      720 tttttcatct tcttgggttt ggttgggtca ctcttcaggt caggtgtgta aaaaagaaag     780
```

```
aaagaaaaga gagattgttg tgttgtaacc cctttgacta aaatctaatg aactttttta      840
acacaacaaa actccttcag atctgaaagg gttcttcttc tctcttagtc tcttcgtcct      900
tttattctcc gtcgtcgttt catgatctga ctctctggtc ttctcttctt cttcttcttc      960
ttctattttt tcttacttcg tcactgttgt gtctgaac                             998
```

<210> SEQ ID NO 10
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0665

<400> SEQUENCE: 10

```
aaaaaggatg ggtaatggga cctatttttcc ccaacatccc acatgcacac ttccctctcc      60
attctctcac atttatttct ttcattctaa tttatccatt ccgtgtgtaa catattcact     120
aataatctca tctcactaac tcattcattg attgtgatat gtttatctag aattagtgtt     180
ttaacactgt gtctacatat gatttccttt tcattgtatg tgaacatgtt aactcactaa     240
tcattttgta ttttcgagtt aacatgagtc tccacttcgg tagactaaag taaagatagg     300
tttgagtata ataagtttta aaatttgctt taaaatcaat atttataaat aagttttttat    360 cataagtgat ttttgtatgt tatattggac cttgtataaa cagactacag aagaaaatta    420
tttatgagaa cttgtaatgt tagagtggac ctcgtataaa ctaattatgt gggcttttac     480
cataaactat ttatgaaaat tattatggcc cacaccacta taactaaagc ccacatattt     540
agcagcccag tttcattgta agagacatgt tcgctctgga actagaattt tctggttttt     600
gggtatttgt tttcttatgt gtagagaaat gatggtaacg attaaatgtt gtgtattaca     660
atttacaatg gtaagacgat taatatattt acacacaatt ttgttgttgc tgtaacacgt     720
tagtgtgtgt gatgatagaa tttcataaag ctttaactac gaggggcaaa atgttaattc     780
taaatagttg acagcagaaa aagatatgta tacataatat aaggattaaa acgtaaataa     840
taataaataa ggcgagttaa attaaaaccc tgttaaaacc ctagcttgaa acacatgtat    900
aaaaacactt gcgagcgcag cttcatcgcc atcgccattc tctctctcat caaaagcttt    960
tctccttgat tttcgcattc tttagagtct taacgcaaag                           1000
```

<210> SEQ ID NO 11
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter PT0672

<400> SEQUENCE: 11

```
cagccgtaaa tcctccataa atttattttg caagttttgc tcattatata atgagcggaa      60
tttatgatat aatcgtttgt aataatgtta tgttttgatc aaaatttgaa attaaaagta     120
ggtgagaact tgttatacag tgtagataag gtggatcttg aatataaaaa taaaatttat     180
aagatgtatt taaagcagaa aagcataaaa ctttagataa aataatgtaa aaatgtgtta     240
gcatcaatgt tgggatattg gccgacccga acttaatcaa tgtcggaagc cattacttct     300
ctcccaaaag accttttttcc ttcggagaac taggaacttc ctcactacct ttcgcttaac     360
gtgaaagcca taaatttcat atattcataa aaatcagaaa atctaaaact gtttagtatc     420
```

-continued

```
acctgttttt ggtatagact attggttttg tgttacttcc taaactatat gatttcgtac      480
ttcattggat cttatagaga tgaatattcg taaaaagata agttatctgg tgaaacgtta      540
cttcagtcat gttgggtcta gatttacata ctactatgaa acattttaag ataataatta      600
tcctagccaa ctatatgttc tatattatgg gccaagaaga tatagaacta aaagttcaga      660
atttaacgat ataaattact agtatattct aatacttgaa tgattactgt tttagttgtt      720
tagaataaat agtagcgtgt tggttaagat accatctatc cacatctata tttgtgtggg      780
ttacataaaa tgtacataat attatataca tatatgtta tattttgat aaagccatat        840 attactcctt gacctctgcc cccatttcct tttactataa ataggaatac tcatgatcct      900
ctaattcagc aatcaacacc aacgaacaca accttttcca aagccaataa taaaagaaca      960
aaagctttta gtttcatcaa agacgaagct gccttagaa                             999
```

<210> SEQ ID NO 12
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0676

<400> SEQUENCE: 12

```
aagatagtac agtttcagtg ttttgagaaa aaaagctgaa ctaaaactaa aatgtttaag       60
gacacaatat ttagtttcaa ttagataatt caacagtttg aacaattttt tttttttttt      120
tttgaagtca tttatttata caatgttta aaacgcatta agcatttagg cagccgacaa       180
acgcctattg tctaactgta aataggcgct tccacttagg ttcatattgc atatttacta      240
tatgtgtata gtgacaaaaa ccaatatttc tcttattttg gatgaaggta tagtagttgt      300
taaatgttca atataattaa gcattaatga caaataaaat aaaattaatt tagttgataa      360
aaagataatc ttataaaag atcgatgaat agatataatg gtttactgaa ttctatagct      420
cttaccttgc acgactatgt cccaaggaga ggaagtacct taactataat tctgaacata      480
attttgtcta tcttggtgag tattatatga cctaaaccct ttaataagaa aaagtataat      540
actggcgtaa cgtaataaat taacacaatc ataagttgtt gacaagcaaa aaaacataca      600
taatttgttt aatgagatat attagttata gttcttatgt caaagtacaa ttatgcctac      660
caaaattaat taatgatttc aacaggaagt ctgagatgat gggccgacgt gtagttacgt      720
ttcttgaatt gtgagagatg gtatttatta tactgaagaa acattattt actaaataaa      780 ttttcatttc acatcttctg taatcaatgc gggtagatga agaagttgtt aatacgatgg      840
ccaaccatat ggatctcttt tttggcgttt ctatatatag taacctcgac tccaaaggca      900
ttacgtgact caataaaatc aagtcttttg tttccttta tccaaaaaaa aaaaaaagtc      960
ttgtgtttct cttaggttgg ttgagaatca tttcatttca                           1000
```

<210> SEQ ID NO 13
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter PT0678

<400> SEQUENCE: 13

```
aattaaatga aaccgcccct aaattaggag ggatttgggt aagtggtaac acattcactg        60
gaaacatgtg aagaaggag gatgtcaagt agctgaaaac tcagtatagt aaccaacggc       120
ttctcaccaa cctttcatta ataatttggt catccctata tttttattca acattttgtt       180
tttcaatagc ttagagcacc ttaataccct tcagtgtttt tttataaaaa aaacaaaaat       240
tgggattaat catcaatccc caaatgtaac gtttacttag attatgttca tttttctata       300
cacacaaatc atattctttt gttttaatct tcgaaaaacg agaggacatt aaataccoct       360
aaaaaggag gggacattac taccaacgta cattaacatg tttgatagca aacgattttat      420
tttgttcgtt ttgaaaaggg gaaagtaatg tgtaaattat gtaaagatta ataaactttt       480
atggtatagt aacattttcg aataataaga gagggaaaac actcgccatt gtcggcaatt       540
tagaaccaat attagaaggg ttttttttaga gaaaaaggac ttaaaagttt agagaccta      600
acaacaactt atttagaaat agacatgctt aagttgacaa cagcgagttt attttctata       660
tcgaagaaaa atacgaactt tttcttaatt agatttcgaa tgcatgcact atcgagaatc       720
gaccgtcaca agaaaaaact aatatacata ctgtacatat ctatatcaa tattggtggg       780
gatgggttta atgtgtattt ataattcatg gataaattca cacaataagg tccatgaaac       840
tagaaggtac caaaaataag cattaatgac tctttgccac ttatatatat gattctctca       900
tagtaccatt ttattctccc aaacctatct tcttcttcct ctcttgtctc tctcgctctc       960
tctcttctac attgtttctt gaggtcaatc tattaaaa                              998
```

<210> SEQ ID NO 14
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0683

<400> SEQUENCE: 14

```
gattgaatga tgagtgtgca cccttgtatt actaataaaa aatttagcaa cagttataag        60
ctaacgtcat ccatgagtca ttcattagat tcactatttg cgttctcaaa aatcgaattg       120
ttaaaatttg agaagctcta atatacgagt caatgagatg tggcaaaagc atgtccttga       180
ccataaaatt tcgagggggtc aactcattag ataaggacaa gaatcaacca attgaaggcg      240
tcttctataa caagtttctt tattactaat attaaagtcc aatggggtga gggggagaag       300
aacttaaata aaaggaaata attggtaagt gaataaaatc taaatacgat actagatgat       360
tgatttgtgc tagtgcatgg tattagatca gatatgtgtt actattcgaa ttcaaattgg       420
catattccat gttgttgata agaaaattgt agaagtgtaa aagctgagtt actatattca       480
aactagtggt ttacataaag tgagacaaca actgtttcac aaaaatgact ataaaatagt       540
aagtagtatt aggtcaattg attttaaaat tttaatcaaa ttcaaatttg tgatataatc       600
aaatttgttt atagaaaatg ttaagaaatc aattttggca gaactaattc agtgagaaac       660
aatcatttac aaaaacaatt ttaacattat ttaacagtaa gatttgacat ttaacccgtt       720
cgtgtgaacc catcatatct aacatggctc tacccatgac gcctccatgc catggacaat       780
tttgacagat cagaagttct gaacgtggac gaggtaagaa caccatgatg atacgattgg       840
agttagttat gtcgccaccg acatcactgc caatctcatt aataaaagtg gtactaaatc       900
```

-continued

```
tctaatctct attaactata aatataacaa agaaccaaaa gaaagtttct tatctctctt    960
atctttcata atttccaaga aacacaaacc ttttctacta                         1000
```

<210> SEQ ID NO 15
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0688

<400> SEQUENCE: 15

```
acgttcagag gcatcgcttt tgtacaaatt gaagcgggtt tgttcaatat ttaaaataac     60
acaggaaaca ttcaaatgta ttattgatgt tgcttaggtt tgtgaaatga tatgaaccat    120
atcgtatata ttactagatt tttcttatat gttttaaggg tagtggggct gacctatcat    180
tctgtttggc attaccaatc agactatcag agtattcacc attcaggatt ccataactag    240
aaaaagaagg ggtttacatt ttctcatact gtataatttt ctactatcag agattttatc    300
gattacatta atctcatagt gattattctg atttataaaa aagttgacaa aataattaaa    360
accagtattt tataacaaga ttgtctctct cccatggcca ttattttgac ctctgactta    420
tttaaatctt aattaacagc ataatactgt attaagcgta tttaaatgaa acaaaataaa    480
agaaaaaaag aacaaaacga aagagtggac cacatgcgtg tcaagaaagg ccggtcgtta    540
ccgttaaggt gtgtcgaact gtgattgggc cacgttaacg gcgtatccaa agaaagaaa    600 gggcacgtgt atagatctag gaaaaaagaa agaatggacg gtttagattg tatctaggta    660
ccaggaaatg gaacgtcaca ccaaacggta cgtgtcggat cctgcccgtt gatgctgacg    720
gtcagcaact tccccttatt catgccccc tgcccgttaa ttacgtgtaa cccttccatg    780
cgaaaatcaa acccttttt tttttgcgt tcttcttcaa cttttctttt taaatcaaac    840
cttttctttt taaatcaca ttgcatttcc taacgctcaa caaaatctct ctctactaat    900
atctctctct ctctctctct attgttgaag aagactcata atcggagatt gtttgttttt    960
ggtttgctct gtaaattgga gaagttttgt tagagatcaa                         1000
```

<210> SEQ ID NO 16
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0695

<400> SEQUENCE: 16

```
aacattttct ttaacttact cttaaatttt aatagtaagt tgatgcatgt tatgttgatc     60
cgtcttgatc acaaatattg tttatggac gaattctttg acagtaaatg gctatagtga    120
ctcagcttgg agcatcccga tatgaaaaca aagtgcagta ttgtgtcgtg gtcatcacta    180
acgcactttc ctagaactat cgcgcgtgtt tgacctatgc aacacaccag atgtcatgaa    240
cgtatactta aatagaaaca atgatataga caattggcta tattctgtca tggaacgcaa    300
accggataac atgtctatta gattcatcgg acttgatcat ggttatgtct aatagacga    360 attcttttgtt aacgattggt taaacggct cacgttagag catcctacta tgacttcaaa    420
attgataaat attacatgga aatcacttta attttagtta gaaggtagtt aatttagata    480 ttcttatttta ataaattaaa aaatagaaga aaaaagatg agaagagttt tgttttataa    540
```

```
aataagaaat atcttttatt gtaattttaa aattaaacaa atttaatttta tattaaaatt      600 atctttgttt tattgttaag gcaataatta ttttttttggt gggaattgtt aaaacaataa      660
ttagtatact gttaagtggt cctttaataa taagataacg tgatttaaaa aagaacgaga      720
caggctaata tagtagagag gaaaaaatac aatttaggcc caataaagcc caatatagag      780
ttgtgctcaa acacaggtct tcgccagatt tcctatgacg ccgtgtgtca atcatgacgc      840
caagtgtcat tcaagaccgt cacgtggcgt tgtttctaca cataggcgat ccatacaaat      900
cagtaacaaa cacgaaaaga gcattcatat gtacgaaagt agaaagaag agactctttg      960 tgataaaact aagtaagaaa tagcataaaa gtaaaaggga                            1000
```

<210> SEQ ID NO 17
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0708

<400> SEQUENCE: 17

```
gtttccaaaa ctagtattct ttatttgctc tattcattat attttatat ttgtaacgtc        60 ccgaccgtct ttattaggtt tcgacaatca cttctcggaa ggtcgtccat cctgaaatta      120
ctctatccta aacatgttta actataaaat tctctcgaaa cttttgtaac gtatataacc      180
acataaattc tcttaaactt atttgcatac accattatat ttctgaaatc gatatgttac      240
aatattattt aatatttaga ttacttttac tgaatcgaat taaatatcaa atcgaaacaa      300
atctaatcta ccaaaaataa ttttgttata aacatttctt gcctagttct acctcatata      360
cattttagtt aaagaaagaa atcacaacaa ttcccataat tcaataatta aatccacaaa      420
atcttggagt aagtaagaga aataaaaaga tagtatctta acataaacaa ttcaaagatg      480
ctctctcaca caattcacac acacttacaa aacaaaagac agaaacaatg ttttcattca      540
aatcaaaaga agttataaca ctagtacaaa aaaagctcaa attctaatag taactctttt      600
tatttcccaa ttacccaaag attctctctc acttcacaaa actagctttg agagtcgtgt      660
tccacaaaat ccattaaagc tgaaacggtt ttgctcacca ttcaaacaaa tacaaaattg      720
caaaacccca aattataaca aaataatata aaaattaaac cgctaaaaag agtgaaccaa      780
caaaaatcgc cgaatgtgtg tgtaatgaga aaaccgaccc atcatcccaa tcatctcttc      840
ccgtgtcact ctcttcctct cccacgtttc ttctctcttc cctttatggg ttttaacttc      900
tccttcttct tcttcttcaa tcttcagttt tcaaattcaa caacaattca cattttgatt      960
tcttcatcat ctctctctct ctcgcttctc tctcaaatcg                            1000
```

<210> SEQ ID NO 18
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0710

<400> SEQUENCE: 18

```
tagtgcgcgt ggggagaggg aatggtgaaa ccttagtggt taagttatga ggaaaatgat       60
aaaaggataa aacaatcaaa tgcagcttga aacggccata acataaagta ccttatggtg      120
gtgcgaatat ttttgtgttt ctttcactct tttattgctg aaagctacga cacttgtctt      180
```

```
aatatattgt tccgcaagt cacatgatct acttttttatt taacgtctag aaacgccgag    240
atatatgatg attagtatat cacgtctatg caaattgtta gttcgtgttt ggccaaaaga    300
tatcgagaca tgtctgaaga accgagtctg gttttgagat atttcttcaa gcattactat    360
acaatagaaa aaggagacac gcgaatatga taatagcaaa aggcataaaa aggcgaaaat    420
taaagaaaaa cgtaaagtga tttggcctca atcaacggga acgtatctta atttagagg     480 ttcttcttt acttttgaga cgagagagtt tgcgtctttg cgagctgctt tggttgacta    540
aacattatca tattgaaaac caaaatacaa cggaggaata tttgtcacag tttcactttc    600
acattgtttc cttaacgttt aatcaacctt gttcaaaatt tctatagttg taatcatcat    660
tgtttacaaa attttcgttc aaagatgatt ttaaataaaa ttgtgaaaga aaacctttc    720 tgaaataagg attggatgat agtgttaaaa gaaaatatg aactgaggca aaagaggag     780 tggtccccgg aagattgtga aatgtgtcat ctaaaccagc cagacgtagt cacgtgttct    840
ctctagcttt atgaacttcc ttagccagca ccatcattgt gattgtagta tatatgtaac    900
cctaccttca tctctcccat tttccattct ccatatagac tcctttacaa tatacaaaac    960
ctatccaaaa gcgaagaagc caagcaaaca tattataaaa                         1000
```

<210> SEQ ID NO 19
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter PT0723

<400> SEQUENCE: 19

```
gtcatatctt atcaacacgt caacgatcaa aacctttagc ctattaaatt caacggctta     60
gatcaaaacg aaactaggtg ggtcccactt ttaatatcgt ggctgcataa catttcctcg    120
ataactgaag ccgttgtggt ctttctcaga atctggtgct taaacactct ggtgagttct    180
agtacttctg ctatgatcga tctcattacc atttcttaaa tttctctccc taaatattcc    240
gagttcttga tttttgataa cttcaggttt tctcttttg ataaatctgg tctttccatt    300 ttttttttt tgtggttaat ttagtttcct atgttcttcg attgtattat gcatgatctg    360
tgtttggatt ctgttagatt atgttattgg tgaatatgta tgtgttttg catgtctggt    420 tttggtctta aaaatgttca aatctgatga tttgattgaa gcttttttag tgttggtttg    480
attcttctca aaactactgt taatttacta tcatgttttc caactttgat tcatgatgac    540
acttttgttc tgctttgtta taaaattttg gttggtttga ttttgtaatt atagtgtaat    600
tttgttagga atgaacatgt tttaatactc tgttttrcga tttgtcacac attcgaatta    660
ttaatcgata atttaactga aaattcatgg ttctagatct tgttgtcatc agattatttg    720
tttcgataat tcatcaaata tgtagtcctt ttgctgattt gcgactgttt catttttct    780 caaaattgtt ttttgttaag tttatctaac agttatcgtt gtcaaaagtc tctttcattt    840
tgcaaaatct tctttttttt tttgtttgta actttgtttt ttaagctaca catttagtct    900
gtaaaatagc atcgaggaac agttgtctta gtagacttgc atgttcttgt aacttctatt    960
tgtttcagtt tgttgatgac tgctttgatt ttgtaggtca aa                      1002
```

<210> SEQ ID NO 20
<211> LENGTH: 1001
<212> TYPE: DNA
<213> ORGANISM: Arabidopsis thaliana

```
<220> FEATURE:
<221> NAME/KEY: misc_feature
<222> LOCATION: (1)..(1001)
<223> OTHER INFORMATION: Ceres Promoter PT0740

<400> SEQUENCE: 20
tgtggccact aaagatttac ccttaaccgg gcccatataa gcccacgtca agtggcgctt      60
atacgctctc cgtaagagag ccaacatttg gtatgtaatg ttgcaaatta ttcttcaaga    120
caataaattc aaatataatt caatattgtc caaatatagt gatgtacttc agttgtgcac    180
atagaaactc cactaaacca acttttagat agatgcattc acaaattttc aacaatgtcg    240
cgaaagtcta atccatcacc agattctaac attttaatta ttatatttaa ctatacatac    300
tctaatcagc atgagtcaaa cgtgtacaat agcccaagca tataataaga ccaaagtcaa    360
actcaaataa atgtctccaa actcaaaact tgaaaaagac ctaattatta catggtagat    420
atgactttgt cgacaagtaa accaactaat cctcgaagct accttctctt cccagttatt    480
atgtgtgatc gatttataaa tctcttcttc taataacacc tatattttc ttatgatgtg    540 aataaatata aaacttttaa ctttaaaaca tatttatccg aaatattgca cttagatttc    600
aaatagataa ataatagtac tatctaactg atattgaaaa gacctaacac ggaaaacagt    660
tttataaaaa atcccaaatg tgggtaatta tcttgatttc ttgggggaaa cagaaaatgg    720
attaagatta atcggagtcg tgtcaagcag ctcgttaata actgtagcaa gttgactgag    780
taagcatcaa cgtgtcatct ccgtaaagcc cattatttct agtctcgccg cgtcttctct    840
tccacgtagc acttcacttt ttctctcctt ttgtttcctt tggaacacaa acgtttctat    900
ttataggaat aattacgtcg tccgtatctg tgtcggaaca tagatccaaa ttaaaagcga    960
cttacttaat tacatatcgt tcgtgttttt ttcttcaaaa a                        1001

<210> SEQ ID NO 21
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter PT0743

<400> SEQUENCE: 21
tcgattggcc cgatcggccc caaaatcaag ctgagccgct tcaaacttca gcttttgaaa     60 tcaccccccaa actcatgtcc tcttatcatt ataactaaag gatctttcat tttatttaac   120
tcatcgtctt gcactaccca acccaaaggt tccaactata cccgaagctt tctaaaggtc    180
caaagacttt tttttcgag ccagactatt caagccaaga aaagccaaac cccacaagcc    240 agtactttc aattccatat tataaactta tctgtcttgt tttagtccca ctaaaaacaa    300
cagaatttaa tttaggttga gctaaaaccc ttgacaaaag tgtatagtcg tcgattcagt    360
agcacactca tcactcatca gatttgatag ttgacctaaa gtatgactac tccatttcaa    420
ctaacaaatg aaaataaaag agacctaagg gttagaggat tgaaactata ctctcaagtc    480
ttttatcact aggctactac cagctagtta acttgatgga tttaagcaag aaaacgtaga    540
atttatattc gagcagattg tttagctaaa aaagcttggg tttgaaattg ccttttctcc    600
catataagca cgtcggttcc taaataactc tttctagcgg agagtgtctt tccaataatt    660
taataaaaat ggtgtttgta tatcaaaaaa aaagaaaaa agaaactgat cgagatagaa    720
cgtttgcagt tttataaaca atttaaaaaa caaaaaaaat taaactcaat gtattttta    780
```

```
ttaattcaca acaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

```
<210> SEQ ID NO 22
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0758

<400> SEQUENCE: 22
```

```
agctagccac atcagtgacc aaaaaagata attaacaaac caaataaaat aacaaatttt     60
gatcatttgg aataaaattt ataaaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
tacatgatat ttagttatta tagcgtaatt aactaagata agaaattaac taaagtgata    600
ttctgattat tattattttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
taatcatttt ttcgtgaata attctctctc ccattccatt atttctcagt atctctcttt    900 cttccccta ctttattgtt gcttttaaac cttcaatttg ctcataaacc aaatatataa    960
tatcaaaaca acaaacaaa aaatcagaat tccctaata                          1000
```

```
<210> SEQ ID NO 23
<211> LENGTH: 921
<212> TYPE: DNA
<213> ORGANISM: Arabidopsis thaliana
<220> FEATURE:
<221> NAME/KEY: misc_feature
<222> LOCATION: (1)..(921)
<223> OTHER INFORMATION: Ceres Promoter PT0829

<400> SEQUENCE: 23
```

```
aaagttttga attattggga atcaatttcg aagttttgta attctttggg ggctaatagg     60
atattttatt ttcttggttt cgtctattgt tgttttccta tttatggttg ggcttttaga    120
actctggaca ggcccatgtc atatgttttc ccttctcctt atattttca tttttcattt     180 tgttaaatta atgcataata tccaaaaaca atttaaattt tgaaggaac cctttagtta     240 cggctccgaa gctttcacaa gtgagaatgt gagatcaaag aaggcaaatg gaggatttta    300
aaagttaaaa tcatctttta tctgcaaaag ttgacaattt ttttgtatca aatctaaatc    360
```

```
atcaaactct cttaaactac aagagcataa caacctctat gtaatccatg aaataatctg    420
cttgaaggac ataacataaa tcattatggc tagagtgact aacttcaatc aaatcctctt    480
aactctagct cccttacaat ggtatcgtaa acattatgc attagggatt gttgtcctag     540
gaaaataaaa taaaatccc cacagaccaa ctaccatttt aacttaaaaa taagcttcgt     600
ccgcgacgaa ttgttttcca tcctaaaaat agaatggtgt aatctgctaa tggtttagtt    660
ccattaactt gcaagttcta ttgaaagcct aaatgtcaat aaagatatta aaattcggag    720
tcaaaagaca atgaatcaa aagcaacaag acaagtcagc tccattcttc actacccatc     780
ttttacaata aatcatctct cttttcacaa atttcaaact actctcattg cccttttagct   840 ttgttataga gccaacacta cagagagact cacacacttg tttcaataat taaatctgaa    900
tttggctctt cttataaact a                                              921
```

<210> SEQ ID NO 24
<211> LENGTH: 763
<212> TYPE: DNA
<213> ORGANISM: Arabidopsis thaliana
<220> FEATURE:
<221> NAME/KEY: misc_feature
<222> LOCATION: (1)..(763)
<223> OTHER INFORMATION: Ceres Promoter PT0837

<400> SEQUENCE: 24

```
aactacaagg gagacataat atcaccatct ggttcctgtt atcatctgaa gatttcttgt     60
tttaccttcc agtgataaaa tgatccttat aatacatata gatatattaa attgctgtat    120
tttaagatta tagatatata aggtacatga gagtgtttat ttaaaaaaat tcacttggaa    180
ttcatgtttt gtgatacgtt agattggaat ccatttggga aaagaagaat catctgttct    240
tatgtctcaa attttgactt cattcacttt tcttcttgtc ttttaagaaa gcttccacaa    300
tctaactgtt cgatgtgaaa actgagattc gagtaagaaa atgtgaactg tgttatactg    360
ttttttaatt agataattta gattgcactc agataaatta ataacattcc tcgaatactt    420
ttatgtgatt ggatatatta ggtatatctg ccaaccaacc aataaactgc tatgtttaaa    480
caaattaaat aaattagtat atgtttactc aagaataaag aagatagaaa agaaaattct    540
atatgagcta aatttgctgg aggaggcatc ggacgtgggt accagacctt tccaagcaca    600
cgagtagtgc ttagccatgt catgctaaca tacaccattt ggttcataca aaatccaaat    660
caaaatctat ttttaaaatc ttttgcacac gtctttgaaa aacacctctc atactatagc    720
tacggaagct tcaatttcaa ggtttgtcta aaagctaacg att                      763
```

<210> SEQ ID NO 25
<211> LENGTH: 751
<212> TYPE: DNA
<213> ORGANISM: Arabidopsis thaliana
<220> FEATURE:
<221> NAME/KEY: misc_feature
<222> LOCATION: (1)..(751)
<223> OTHER INFORMATION: Ceres Promoter PT0838

<400> SEQUENCE: 25

```
atactggtat gcttaaggtt gaagccaaga tctctgtctt acccaagtaa ccactttcta     60
ttagaaggga tcaacactaa gaatatggag atttaagcct aagggctaag gcggttctca    120
acaatacatg atgtgaatac aatcacagac gatttactga ggtttgttga taagatcttg    180
atcagtctct gcatcatctg ttcaacaatc tcaatctttg actgtttgct ttcggagcca    240
taaacagagg aatcccttat tccctgttat aggagcaata caccaagtat tatttccatg    300
```

```
gctgaaattc tcttatggaa acctaattgt tccattgaag ctgtaaaatc gaatctggtg    360
aatattctcg agcaaagccg catgctaatt atgtcaattc agaagagttt gattaggaga    420
ctcgaagcga gtttgatgat cttcttgat gttcaactcc gattgtaagg gtataattga    480
cttttcatgt attacggctc caccacctga cactaaggca ctctttgtcc atctcgttgg    540
tatcatcgga ttcggatggt aaaaataaaa agagcagagg aaacttgtta ctcatgcaag    600
cttctcaggt gccacgtcac tccattacgt gtcatcttca cacaccatct cgctcaaaac    660
cgatctcatt tttcaaacct taaaggcaga agcaactgat taagttaaca ctcttgagaa    720
gctctcgatt aagcttgaac ttggaggatc a                                   751

<210> SEQ ID NO 26
<211> LENGTH: 669
<212> TYPE: DNA
<213> ORGANISM: Arabidopsis thaliana
<220> FEATURE:
<221> NAME/KEY: misc_feature
<222> LOCATION: (1)..(669)
<223> OTHER INFORMATION: Ceres Promoter PT0848

<400> SEQUENCE: 26
tctctttaaa tcagttaact aaccgtttat atatttacga taaggtttga agagattatt     60
gataaaataa tacatttcat aatcccgcgt tcaaccgttt aaagtaacat ttaagttgac    120
tatatctaat ttttttttcca ttaaatatgg agctggtaaa ctttatcaac ttctaaaaag   180
tgtaacaaca aaaattaggt caatcacaat tctgtttttt ttattatttt ggattgactt    240
ccaattgcaa atagtcttag tgatcaccat tatcatacat atatacatca gtaggtttc     300 atcatgatat accacaaagt atttgacaag ccatatggtt ttggatcaaa aagtcggtcc    360
aaaattaatg ttttatgtgc aagaaccgac ccattgtaca cacgtgttaa catcttcaag    420
actttcatct ctatttttct tttggtcatt aagatacccca ttgatccgaa tctgttacat   480
tcccacctac ttttttaatt tttactatcc actccaaatt aaacacaacc gatgatttta   540
ataattggaa gcttttaaaa atatttcaaa acaagcctct ttgtgtttgt ctatatatat    600
acacgtaata agaaggtgaa tgaatctcac agcttacttg ttctaaggct tccaataacg   660
aaaacagta                                                           669

<210> SEQ ID NO 27
<211> LENGTH: 702
<212> TYPE: DNA
<213> ORGANISM: Arabidopsis thaliana
<220> FEATURE:
<221> NAME/KEY: misc_feature
<222> LOCATION: (1)..(702)
<223> OTHER INFORMATION: Ceres Promoter PT0863

<400> SEQUENCE: 27
cgggaaacga caatctgatc tctagtccag tcgattggcc cgatcggccg attataaact     60
tacatgagac aagtataaat aattattata aacttattaa gtttaagatc aaggcttttg   120
tgcaatgtat caatgaatgt tagatgtgat atgatgaaag caatgttta aacacataca    180 tagtcattga tcggaatgtg tgttattaga aatgcatgcc taagccgata gggttatcta   240
tgtttggtct tggacattat agccaaattt cgaatctaat tcttccaata tatatttttt    300 ttttttttgct tagggccact actagtattg cttatcaatt ttaagagctc atgaaaatgc   360
aacaatatag tagttgcaaa tccttgtttc aagagaaatc aaagggccac ttgtgaattg    420
aataataata atatttgcaa ataacctttc actaaaccat accaacaaaa ccacacagat   480
```

```
ttggcaaaga cataaccttt gggagacgtg aaaaggctca aaatttgaca attgtcctta      540
caaattcgct cattagtgca attgtgagat ttgtttgcat ccaaatccaa ttcataactc      600
acactcgtct caaattcgaa aaggcctgca gggccagtgc actgggatcc aacaatgtcc      660
tccgactcgt ccaagatcaa gaggaagcgg aaccgcaccg cg                        702
```

```
<210> SEQ ID NO 28
<211> LENGTH: 435
<212> TYPE: DNA
<213> ORGANISM: Arabidopsis thaliana
<220> FEATURE:
<221> NAME/KEY: misc_feature
<222> LOCATION: (1)..(435)
<223> OTHER INFORMATION: Ceres Promoter PT0879

<400> SEQUENCE: 28
ttctaggaag actggtcaag ctaagctgtt tctgtttttt gttttgtac tttacttttt       60 gtttgctagt gggaactggg tttattgggc cttgaagttg ataaaagatg aataaaagac     120
atatcgccta agcccatat gagaagcaga agacaaaaac ctccaacttt gggcataaat     180
tttgattata gttaaaagtc cagacccaat ttggcacctg gcttagttac gattctaagg     240
catgacacct gcctaatatg tttattacag aaaataaaga gaatcagcta ggtgtccctt     300
attgaacaca ttaacaaact ccaacgcac tacgtgtctt cgtgactctt actatatcca     360
aaaacctata gctaaagctg aatttttccat gattagtata gtcccaacca aaaaaatact    420
gaagaaggca taagc                                                      435
```

```
<210> SEQ ID NO 29
<211> LENGTH: 397
<212> TYPE: DNA
<213> ORGANISM: Arabidopsis thaliana
<220> FEATURE:
<221> NAME/KEY: misc_feature
<222> LOCATION: (1)..(397)
<223> OTHER INFORMATION: Ceres Promoter PT0886

<400> SEQUENCE: 29
agtgtatttg aaaacgacat tgaagaatta atatattttt ttttaattt agttttttat      60 agtacaaata ttaaaacaaa caatcctacc atatcataac atttgtaaat aacattttaa    120
gttttgtttt gagttttaat taattttcta tgacaaaaaa atgaagtcaa tagactaagt    180
gaatcatata gtataaataa acacaattta aatagtttca aataaattta gaaagaataa    240
aacaaataga aatcagaagg tgtctgtttc ctcctcgcaa catacgatca aagagaaaca    300
acttgaccct ttacattgct caagagctca tctcttccct ctacaaaaat ggccgcacgt    360
ctccaacctt ctcccaactc cttcttccgc catcatc                              397
```

```
<210> SEQ ID NO 30
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0007

<400> SEQUENCE: 30
agcagaacaa ctatatttat tgtgtcacat aaatctgaga tcatttataa ccaccaaaga      60
acctatacac agtaaatgac aaatgtatct ccctctatct ctattgccca tatgtagatg    120
ctaaagtaag atttctcttt tttttaatgt acttttttt gtataaagta tattccataa    180
```

```
gaaaaaggaa aagcttgttt atggatcaat tgaccccaaa aaagttttt agatcaaagc      240 ccaatataaa aaaaaaacac agtagtgaca caaaggaact taaataaacc atgaattgat      300
ctataaacag tagagatcga taaggcgaac attttccatg tgaagtgtct tctttcatct      360
ataatatttt tgacatccaa taatttcctc tataatatca ttcacataat tgatagaaac      420
attatgttag aattgtccac atcatttgag ctgtaatata ttctgtttta acaaattata      480
tggtagttgc ttaatcttat gtccatcttc ttctatgcat cgttttcgcg cctagttgtc      540
cagtccattt caactaccta cctctaattc ttatcttaaa acaacatttt ttaatttaag      600
tattatgctc aaagactaac tagatagaaa accgttatta acattaaac gaattaaaag       660 tcttacatgg aaaatgtagg tttataaacc acgagttatg attgacaata aaaaaaatgc      720
aaatcatcaa tcaaaagaga cttgagtgcg actctatatc aaccattgca attaaaatta      780
tctatcacaa aaattttaga cagattaagt taatttagtc taaattcact aatttatttt      840
ctataattag taattaacta tatttattta tttacacatt ttctgataat ttagaaattt      900
gcatgaataa caaatataag attttggaaa ttagtagcaa atttaattaa taattatttt      960
tgcctaaatg aaccaaacta taaaacctcc acatacacca gtcatcaaat ttacagagac     1020
aaca                                                                 1024

<210> SEQ ID NO 31
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0008

<400> SEQUENCE: 31
ctcgagagat gaagtcttag taatgtttga acaaacaata atcacgtttt ccatcaaatt       60
cgagcattta aagtttatat tactacatgc cccaagatga taccgtccat ctcatccgaa      120
aatatttctg aaattgcgct aagacaacaa tgtttgctca aattcgatca tttaaagttt      180
acaaatctct catcaatctt acaaacttct cacactaaac agaggtacat attttcttat      240
aaagacaaaa ggttcgaaca gctggcttct caactcgagt tgtttgtcag ggcctctctt      300
cactaactac aagttggtac ttcaaatatt ggtggctagc ttcacgtgat attgtctaca      360
aattaaaccc atgaaaaagc tgcattaatt gttccaagtg aaccctgagg agtgtcaata      420
gtctttgctt tagtgtgatc attaaaccaa atctctaaat tcctaatttg tactaacatt      480
tggaacgtat ttcctactct tctccctgct ccaactccca aaaataagat tagttagatt      540
tctataacta atatacatgt atactcccaa aaacagtaaa accatattaa taaagctaat      600
tttgcataga tttatttcgg taaaccggcg gttcaagttg gggaaaaaaa agacaaacgg      660
tctaaagtca tccaaagaca aaaaccaaa gacaagttga gagagacgag accaatcaca       720
acattgcttc gtagattgcg tgacatcatc cttgacggct actttcattt gtgtcttatt      780
tggataaaac gcacgtgttt aattcacgaa ccttcatagc aataagaaat ttccattact      840
ttcatatttt caactttttt tattacccat tacatgctta aaatattaat tcacaagtct      900
ttgtcaaaat tcaatatttt ccaggttcat gaacccttt tatctcaatc tactctataa       960
tatctcccta taaattacaa caaaacctct ttattttttca                         1000
```

```
<210> SEQ ID NO 32
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0019

<400> SEQUENCE: 32
gatataagta gaatcatttt ttgccgccgt ttctcgctaa cacaccgaaa actgaatcaa      60
atctcctagc tcttctacgc aaaatcgagt gcatcgacaa tggcggaacg tggtgtcgaa     120
cgtggtggag atcgcggcga tttcggacgt ggattcggtg gtcgcggcgg tggaagaggt     180
ggtccgagag gtcgtggtcg ccgtgcaggt cgtgctccag aggaggagaa atgggtgcca     240
gtgactaagc ttggtcgtct cgtaaaggaa ggtaagatca caaagattga gcagatctac     300
ctccattctc tcccagtcaa ggagtaccag atcatagatt tactcgtcgg tccttcattg     360
aaagacgaag tgatgaaaat catgccggtt caaaaacaaa ccagagccgg tcagagaacg     420
agattcaagg ccttcatcgt cgtcggagat agtaacggtc acgtcggatt aggagtcaaa     480
tgctccaagg aagttgcgac ggcgatcaga ggcgcgatca ttctcgcgaa attgtctgtg     540
gttccgatac gaagaggtta ttggggtaac aagattggaa accacatac ggttccgtgt      600 aaggtaaccg ggaaatgtgg atctgttact gtacgtatgg ttccagctcc gagaggttct     660
ggtattgtgg cggctagagt tcctaagaag gttcttcaat cgctggaat tgatgatgtc      720 tttacttctt ctagaggatc caccaaaact cttggaaact tcgtcaaggt atgtactttc     780
acaatggctg ttttggtttg atgaactctg aattaggcag tgaaaagta atcattacca      840 gttaagtgaa tttatattga agattaggat ttagctgatt gtattggttt gagcatgtga     900
gtttgtgttt aagattgctt gaattgaaat gctttaggtt gtttgattac gctaaattct     960
gactaatgta attcaaattg ttgttgtttt ttttggtc                             999

<210> SEQ ID NO 33
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0028

<400> SEQUENCE: 33
gtcagtgaag tcgattggta gtacttgaaa cacttggttg gtttcatgta tttggcctat      60
atataaacaa acatcgtaat tatatacgga ttttttttcgg aatttttacgc catatctgta   120 agtatatata acatgcatgt cgttttcaaa ttcatatgat gaacgatcca cgtaagtgct     180
actactccta caatattgca tgagagagat atgtatttat aaattttatt ttgaagaaga    240
aataagaggg aaggttactt gggtggatcg atgtgaaaac aaaagaagaa aaagcgaaac     300
ccactaagcc attacatgat atcgaccttc ttatcttttt cctctttatt ttattttttct    360 catcttcttt ttgtcaggac ttttttctac ttaatgaaac ctccaaacta tctaactaat    420
acactcccat gtagaataaa gaaaattata taagatattg ttgatatttt gtaactagaa    480
aatatatttg ctctgtaatt tttcgtaagt taaatcaaca ttttaaagta gaaacaaata    540
ttactgcaaa aagtaggatc attattttttg tccaaaatct cagttagcta tagggttgta    600
gtaaaaacaa aacacattct tgatttgccc caaaaaataa agagagagaa gaatattgtt     660
```

```
caaaagtggt ctcttctctc tctaattatg ttttcactaa acccaattag attcaaacag    720
tctacaaagt ccaaaagata aacatgggac aacaattcga tgcaaaaaat cctcttttca    780
tgctcttttt ttattctcta gtcttttaaa ttactaataa aaactcacaa atccaccaaa    840
cccattctct acaactcacc ttcatctaga tttacccact cccaccgaga aacacaagaa    900
aaaaaatata catatataaa tatacaagac aacacatgat gctgatgcaa tatacacaac    960
aaagtattaa atcttagata ttgtgggtct ccctttcttc tattcatttt cttattcatt   1020
aaaa                                                                1024

<210> SEQ ID NO 34
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0039

<400> SEQUENCE: 34
ccgttcgagt atttgaaaat ttcgggtaca cccgcctaaa taggcggacc ttatctagta     60
tatatataca tttgaactat attgtttact ttttagttga tttaggctat gtcatgacat    120
tgacataaat ctacctgtta tttatcacgt gtaattcgtg taaagtgtaa actagaaagt    180
tcaaatacgt atttgttttt gttctgttat ataggattgt catagttgta aatctacaat    240
ttattacaac atgaataagt acacaagcaa tgtaattgga tttaattgct aaactcttta    300
catggtcaat ctaaatttga taagaaatac gtcacatatt actaagactg atagtttttt    360
tgttgtcacc aattattttt gttaaattga cgaaaacaat tccaaaaact caaatgtaca    420
aaatcataca gtctcacaaa catctcatag agaaagatat aaatctccca tatgggaacg    480
ataacacgag gtcgaaatac tattcgtaaa actaaaacgc cttagttata aatcgttagt    540
tgtaaccgcg gtcgagaata catacagatc cacgaaacta ctactacaca tgctgctgaa    600
ttggaatttg gaaaagacca tcttctttag gaagagctca cccaatgagt gacaaaggtg    660
tcggtggctt gttttctacc catatgtata catcaaatgg tagtttcatt aacgtttggt    720
tttgagaaaa gtaagacttt ggctagtagc taggttcgta tataataaac tcttttgaga    780
aagttcatca ctggtggaaa atgttaaacc ggtttttttct cattttttcc gccatgttaa    840
ccaccggttt aaaagaccg taacacattg aaagattaat aagggtatat ttgtaattac    900
ggtttgctgg caattttttaa ttattatttt aattagagaa aatagagaag ccctatcaat    960
gtacatggta tatatataaa aggcaaaacc ctagaaaacg atactattcg actcagccgt   1020
cctt                                                                1024

<210> SEQ ID NO 35
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0050

<400> SEQUENCE: 35
aatctgatct ctagtccagt cgattggtac ttgagggaaa catcatattt ttaaaccttg     60
tctcagtaag ctaacacaca ccccttgtga ttacttatcc atgtttatcc acaagaatgc    120
agttggattg agatattttc ttctttgttg aaatcaggcc tcaaggtgtt catgtggtct    180
```

-continued

```
gcaaaaaaat tcccaaaaat aaagatagtg acatctgaaa tcgataatgg attagacgaa    240
gagtttcgtg ttattccttg gtatgggcgg gtttggggac agatattttg gcacagacga    300
ggactaggcc actgtggtcc tgcagcatta ggtgtccctt ccatgtcctg cattacattt    360
tattgatgga ttcatcaccc tatctactac aacggctaca caaactatga agagttttgt    420
ttactaataa atgcccaagt gaggggtcga tcgaacccgg gacacgtttt tcagtttacc    480
atatagaatt atccttggaa cccttgatac tccatagaac atcaccacct ctgttgtcat    540
ctcaggaatc caggttcaaa cctagtctct ctctccctag tgggaggtat atggccactg    600
ggccaatgat gacaaaatgc aaaaaaaata aaatacattt gggttcatta tctaaaatat    660
ctcttgtgtt tgtaagtttt ggttgcacac tcgtgtggtt gaagtgtgtg tgagaggtac    720
tatacaatac actctgcttt tgttttgtac ctatctcttt ctcttctcca catatccaag    780
actttgggga taaagctgag atcattggtt gccatttggt tgtgtagaag caatcaccca    840
tttgctttat ccgaggttga taaatttcct cgggttctcc ttctgacacg tatgacaaat    900
tctaatagta tattcctcgt agatattacc tatatattct caatagttgc aggtacttaa    960
ggctttgtct tggcatcctc gtcctcttca gcaaaactcg tctctcttgc actccaaaaa   1020
gcaa                                                                1024
```

<210> SEQ ID NO 36
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0086

<400> SEQUENCE: 36

```
cttatccttt aacaatgaac aggttttag aggtagcttg atgattcctg cacatgtgat     60
cttggcttca ggcttaattt tccaggtaaa gcattatgag atactcttat atctcttaca    120
tacttttgag ataatgcaca agaacttcat aactatatgc tttagtttct gcatttgaca    180
ctgccaaatt cattaatctc taatatcttt gttgttgatc tttggtagac atgggtacta    240
gaaaaagcaa actacaccaa ggtaaaatac ttttgtacaa acataaactc gttatcacgg    300
aacatcaatg gagtgtatat ctaacggagt gtagaaacat ttgattattg caggaagcta    360
tctcaggata ttatcggttt atatggaatc tcttctacgc agagtatctg ttattcccct    420
tcctctagct ttcaatttca tggtgaggat atgcagtttt ctttgtatat cattcttctt    480
cttctttgta gcttggagtc aaaatcggtt ccttcatgta catacatcaa ggatatgtcc    540
ttctgaattt ttatatcttg caataaaaat gcttgtacca attgaaacac cagcttttg     600 agttctatga tcactgactt ggttctaacc aaaaaaaaaa aaatgtttaa tttacatatc    660
taaaagtagg tttagggaaa cctaaacagt aaaatatttg tatattattc gaatttcact    720
catcataaaa acttaaattg caccataaaa ttttgtttta ctattaatga tgtaatttgt    780
gtaacttaag ataaaaataa tattccgtaa gttaaccggc taaaaccacg tataaaccag    840
ggaacctgtt aaaccggttc tttactggat aaagaaatga agcccatgt agacagctcc     900 attagagccc aaaccctaaa tttctcatct atataaaagg agtgacatta gggttttgt     960 tcgtcctctt aaagcttctc gttttctctg ccgtctctc                           999
```

<210> SEQ ID NO 37
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0088

<400> SEQUENCE: 37

```
tcgattggga ttactacttc atctagtaag gttctgaaaa cgtttgttgt tgataaggaa        60
gattcgtctc aggttattac tgttgatctt caaggtttgt gattgtgacg cttatacatg       120
tgctgaaact gtggtgttta tttattgaaa acaaaaaaaa agtctctctt gtagtttcat       180
tgtactaaat agaaaacaag aaacgttttt ttctttaatc ttctacattg ataatattgg       240
atcaaaggat tgtttctgca agacacaaca caaacatact tatactagtt tacttctact       300
aagtactaac tacataccca tacacacact tgcacctaga ctttacttct agacatcatt       360
accctaaggt agaaccaagc ttacaagcaa gttttaccga caactcttac attacaactc       420
tagtctgtag tctttaacgt agacttacta actagtcatt agtggtttaa ttttttaaat       480
tttcatccat atgttttgt tgtagatata aactaaagtc ggtcacattt aataattgtc        540
attatgtccg cgtaaaagtc aattcagcta ttggacattt atgaaatgta agattttctc       600
tctcatttcc ccgtgcgtga agacatgcat tggttttct gtaataatca acaaatccaa        660
accccttttc gatctttatt tggacattgt tagagacaaa atttctctat agtctttttc       720
ctaatttgat accatgtttt tgtttctgca caaatttact cactggttta actaactatc       780
cacttattta tgattttacc attaggcgtc agctagccct agtcaaattt gtaaacaagc       840
caagctatct acataaatcg agatgtcatt aacgttaatc gtcgttaatt cgaatttgaa       900
aacatagata gctttagcag tacaatgggc aatggtaaga agaatagcaa aaggcccaat       960
atttggtttg cagaaattaa agccttaaaa aaaagcccac agatatttgt caaagaaccc      1020
taat                                                                    1024
```

<210> SEQ ID NO 38
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0092

<400> SEQUENCE: 38

```
aaagattgag ttgagagaga tggtggagac gcagaacaga caaagggagt ttaccatata        60
gtgctctaaa gggcaatgag attgcagtga tgtggctatc cggggaatca tcgcaggtta       120
ttccttccca tgagcaacaa tcaatggatg ggttccaatt cagaggagaa acagaagaag       180
aaacgttttcc agagaaccac agtagggatt ctcgatcttg cgagttgcag agagcctctg      240
aaactgcaat agaaaggaca ctgatgaaaa gaacacactg aaggagtatg ccaatcatgt       300
gaaaactcag agcttgtatt ggtcttgtgg ttgatgaagt tctcacaaaa cctttggctt       360
tgaatctccc ctcattagtc atggtgagaa caagaacaag acgagaaaca gacaaagaag       420
atgaaaaaac ttgttggcca gtgttgacta agggggaata gccccagaca taacaaaatt       480
agacttgtcg tacatcttta atattttttt atctgtttct ttgtcctgac gctttcatta       540
ttcctgtgat caattttctc ataccattgg tccatcgtta atcctttctt aatttcattt       600
```

```
tctacgtaac atgagaggag accaagtcct atgagaacag ttgacgtaac agtggttgtt      660
aagttaagtt aaaagagga agctagtgag agtgaccgtt aggtagagaa gtgagatctt      720
taaccactct tctttctctc tctctctgct tttttcgtcg tctttcacat ctactgttcg      780
caaactctct tatgcttcca ataatggtga taccaattga gacttgcagg agaatctcct     840
cttctccaca ctctatcaac tggtcagcca tggaatggtc gtttcagttt caatattcct     900
ggattctttt taaggattcc tgtttctctt ctgttcctgg tatattctta acgacgaaat     960
tagtatcgga tcctggtaat acattttgaa gcttttaagt accattgcac tgggatccaa     1020
caat                                                                  1024

<210> SEQ ID NO 39
<211> LENGTH: 1020
<212> TYPE: DNA
<213> ORGANISM: Arabidopsis thaliana
<220> FEATURE:
<221> NAME/KEY: misc_feature
<222> LOCATION: (1)..(1020)
<223> OTHER INFORMATION: Ceres Promoter YP0096

<400> SEQUENCE: 39
gaggtcagtg agtcgattgg tgcaaaattg aaaaattgaa gggtgaaaca aatttaaaga      60
taatatctat taaatcctct aattttaaaa atttagcaaa aattgtattt tcttatggat     120
ctgttagttc acacgtatct taattagtac caaatcatat ctaatgatta gtgataaaac     180
tagttagata tctatatgtg tctttaccat ttaacttgaa tccttcttct ttttttttacg    240 taaacaactt gaatccttcg ttaatacata aatttaaagc attttttctt taattctatt    300
gatcggtata tatttactat aagttttagc tcatatgcaa tttcaaatga tatgctttta    360
aattttgtct aggtgtgata gttgtatctt taacataaat cttatagcaa aattatactt    420
gatattctaa atttatctat ttgctcttgt gaacctcata ttagtctaga gaaactttga    480
aatcctttca attagttgta tgtccaatac attttttacta acatttatta gtctttttaa    540
ttaagattat tgttagaaaa aaaaagattt tttaaaaata aataatatgt tttagataca    600
atgtgagtta ggcttcttat atttttaaaaa ataaatttat ttcatactta aaaatagttt    660
ggaatttcaa tttatttggc tgaataccat aaaaatatgtc aatttgaacc ttatacccat    720
tgactatttg gtgttagaaa ccctttaaca aaaaaaaact atttggtgtt agatatcaaa    780
ataaaaaaag tttaaccatt ggtttcttat attgaattgg atattgttac atgtattaaa    840 gttttttttgg tttaattttg aaacgttgat agaaactatt aagtttaagt ttggtagtat    900
atttatttgt ggaaaattta attgccatta aatataacgt caactttttt tggttttttt    960
tgagaagtta cgttgtgatt ttgatttcct atataaaagt tagattacgt cattttttaa    1020

1020

<210> SEQ ID NO 40
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0097

<400> SEQUENCE: 40
ttcatcttta tatttaagag tttaaaaact gcaacttttg ttttttctttc actaagtctt     60 atggccacag ttaattaaaa gcagatgaaa ggtggtccaa tggaaaagga gaatgtgatt    120
```

-continued

| | |
|---|---|
| gggctagttg ggagagttct gatgtctagt gttgggtaca cgtgtccgtc agttacacat | 180 |
| agcattaaat cagacggcat gtcattattc aaatctagtt cacatagtac gactaatagc | 240 |
| tgataaatta atgattatac agcatatgaa ttatgaattc aaaaaaaaaa aaaaattgaa | 300 |
| aatgttaagg agatgctata ttttacaaaa ttcatcgcaa tgctttctac taatttgcta | 360 |
| agtggtcttc tccagttagt cttgtcgatt ccaagcgata ttattaaatc ttgaagcatc | 420 |
| gctcaaagca ttatagctta agataaccaa attgttatta aaacaccta gtgaaatttt | 480 |
| taaattaaaa caattttgat atctttgtaa tatctaatac tactctttct gtgtctaaaa | 540 |
| ggattaattt tcaaaaattt cacacatatt aaaaaaaaaa aaaaattact agctaaacaa | 600 |
| ttttcaataa tcataaaaca atagtaactt ataattttt ttttattttc aaaatagtcc | 660 |
| ttcaagttta caattcattt tagtattata atcaacaaaa tttgtattaa aagttggaa | 720 |
| aattaatctt tgtggaacaa aaaaatctag aaatcatttt ttagaattag agagaggttt | 780 |
| gataaaaaa aataaaaaaa aatagagaga ggtagtacat actaaacgat gtgatactac | 840 |
| tattgacaaa atcttaattc tcagtttagt agaataaact agaaggaatg aatgaagtaa | 900 |
| atgcgaatcc aactactaac aaaccctact tagtcatcat attttcccat atgaaatccc | 960 |
| tatataaacc catcatcatc tcccactttt ttcatatcca | 1000 |

<210> SEQ ID NO 41
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0101

<400> SEQUENCE: 41

| | |
|---|---|
| ttctcgttct ctagaatatt gctggaccgg attaggtcaa tattattggg ccagattaga | 60 |
| tattgaattg tcgacgttgc ttacgttacg ttatatcttg tttaagaatt aaacctatcg | 120 |
| acttagtctt aattaagaaa acattgcctt aaattctctg gtctgcgacc gttttttga | 180 |
| ccgttaaccc ctaattaaag aaacaaaata attatagaaa gagcactgaa atgtgattat | 240 |
| tttaacagta ctcttatgag aaaattcgta cttttttagtt ttttttttgt acaaatctct | 300 |
| aagaaaaaca ctactactaa ttaagaaacg tttcaaacaa ttttatttc gttggctcat | 360 |
| aatctttctt tctcggtccg ggactaaccg ttggcaaaaa aaaaaaaaa gttgacaata | 420 |
| attattaaag cgtaaatcat acctctcaaa taaaaacttg aatttggaaa caagacaac | 480 |
| taaaaaactc gaatttaaga gaattcctaa aatcaagtga agtatcatca cttggtaaaa | 540 |
| tttcataacc gttggcttct atttctatgt gtgccttggt ttgcaggaga taatatttca | 600 |
| tttccaacca atgatattcg tacacatagt caaacaaatg tttgtctttg ttattatatt | 660 |
| gagaaagaaa caagaaagag agagagagat agataagacg aaggaagtga agcttccaag | 720 |
| cgcccaccgt taaaatctc gtgtgcaagt ttcaaataca agtggccggt ggtctccata | 780 |
| atttgatcgt catccaatta aaaaggaaga aaaagcgtgt tttatacaag aaaactcatt | 840 |
| aaaatagcaa gtctagaaat atctcaacac taatctacca cgtctattac acacacacac | 900 |
| acacacactt gatcttaatt tattttcaag attcaagaaa atacccattc cattaccaca | 960 |
| acttgaccac acgcctatat ataaaacata aaagcccttt cccc | 1004 |

```
<210> SEQ ID NO 42
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0102

<400> SEQUENCE: 42
atttggttga taacgttttc actcgactaa ttatatactt cagaaggata gtaatagaat      60
accaaaataa ttaaatgatt ggttagtgcc ttagtggaga cttttttaacc gattctaata    120 gactaatgat gtagctaagc atttatttgg gatcatcact gtttgaaaac gtgaaatgtg    180
ataaaagtta tgaaacgatt aaatataaa ataaccgtac aaaacattat gtaccgtttt     240
tttctctgtt cttttggcga tttggtttag ttcgttacac tctaaatgtt attgcagata    300
tatatataat gatgcatttg catctgagga acatataatt ccggttaaca cttccaaatc    360
ttatatccgt ctaggtaggg attttataaa tcatttgtgt catcatgcgt tatgcttgtc    420
ggctttgacc ataacgcaga gatatagaac tagcttttac ttaacttta gatttattat    480 ttgatctaga gttaagtgga gatatatagt gtttttgtta gattattggt ggatgtgaga    540
gtttgtcttt agtttcaagt tgagaatata aggcaagagg agactctgag gcaatcagag    600
gttttgattg gcaaaatatc caaaaggccc aaaccaagtc gaagcccatc tcgtacaaaa    660
aaagaaagag atctgtaaga aaaaatattc tttgatattc ttacaaaaat aagtgtaaaa    720
cttttattag tcaaaatctt caatctttaa aaactctcat cactcctacg aaagcgcgtg    780
agagttatga gacattcctt aatagcatta ctcacaagtc acaagttcaa aacgtctgac    840
tgaaacagaa acaagccttt gttgaagtct tgaagaagag acattagtac tcgtcgtata    900
gccataaaag gtaatatacg aaatttcttc gctaatctct tcaccttcct ctacgcgttt    960
cactttcact ttataaatcc aaatctcccct tcgaaaacat                        1000

<210> SEQ ID NO 43
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0103

<400> SEQUENCE: 43
gttttgaaga acaatctgga tcgaaatcta acataaggtc atcgtattca agttacgcag      60
tcaaggactt gacatcatcc tactctggtc tgaggttacc acttccaaag atgggatttt    120
tcgactcggt atgcttccta agaaattcgt tttattgaac ctagcaaata tcttgtaatg    180
taagattcct gagatgatga agaaaaaaca aactttttgtt acagcaggag aacggagaga    240
aagaaaacag agaaccaaat gctcttgaag caaacagaag aagaagacac aaatccaaac    300
ttgagacttc ttctacacca gaaaaccgca gcattctggg acaacgcaaa acacgaaagt    360
gaaacgggca atgatatata tgtcttgggt gcgttacaag gcatcgtttg caactgttga    420
gttggataag tcaactgtct tcttttcctt tggttgtagt agctgccttt ttttttccttt    480 gttgctttaa gaaatagccc gaaaaaaaga atgttctaca tttcggagca gaaaactaac    540
cgaatgagtt tttggtcgga tcatcggatc gatcagatat attttgagtt acgaactgtt    600
ataaaaaaag ccataatttt gtgttgagtt tgcaaaatac cttataactt gttatttgag    660
```

```
attgcacctc catatatatt aattcgtaag agtatttatt aagtaagctt tagtataaat      720 cctttttcc tttaaagtaa gttaatgttc tactaaataa tagtaaagtt gaagaaccgc       780
tccgttttta caccatgcac gtgttatcta acaaagaaaa tatggtacac ctaatggcta      840
atgcaaagga caacacaatg aaactaactt gactctgtgt tatagaaacc catagacatc      900
tgcatacatc ctagtatttg tataaattgg actcaaattc ctgaggacaa tcatagcaaa      960
caatcacatc atcgcaatat acataaacaa aagaggaaga aaaa                      1004
```

<210> SEQ ID NO 44
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0107

<400> SEQUENCE: 44

```
taacaatcct tgggaacatt gcatccatag atatccggtt aagatcgatc tttgaactca       60
taaaaactag tagattggtt ggttggtttc catgtaccag aaggcttacc ctattagttg      120
aaagttgaaa ctttgttccc tactcaattc ctagttgtgt aaatgtatgt atatgtaatg      180
tgtataaaac gtagtactta aatgactagg agtggttctt gagaccgatg agagatggga      240
gcagaactaa agatgatgac ataattaaga acgaatttga aaggctctta ggtttgaatc      300
ctattcgaga atgttttgt caaagatagt ggcgattttg aaccaaagaa acatttaaa       360 aaatcagtat ccggttacgt tcatgcaaat agaaagtggt ctaggatctg attgtaattt      420
tagacttaaa gagtctctta agattcaatc ctggctgtgt acaaaactac aaataatcta      480
ttttagacta tttgggcctt aactaaactt ccactccatt atttactgag gttagagaat      540
agacttgcga ataaacacat tccccgagaa atactcatga tcccataatt agtcggaggg      600
tatgccaatc agatctaaga acacacattc cctcaaattt taatgcacat gtaatcatag      660
tttagcacaa ttcaaaaata atgtagtatt aaagacagaa atttgtagac tttttttggg      720
cgttaaaaga agactaagtt tatacgtaca ttttatttta agtggaaaac cgaaattttc      780
catcgaaata tatgaatta gtatatatat ttctgcaatg tactattttg ctattttggc       840
aactttcagt ggactactac tttattacaa tgtgtatgga tgcatgagtt tgagtataca      900
catgtctaaa tgcatgcttt gtaaaacgta acggaccaca aaagaggatc catacaaata      960
catctcatag cttcctccat tattttccga cacaaacaga gca                       1003
```

<210> SEQ ID NO 45
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0110

<400> SEQUENCE: 45

```
gggatgcggt tccgcttcct cttgatcttg gacgagtcgg aggacattgt tggatcccag       60
tgcaatggta atataaaaca agaaaacaag agattttata ggacaatcac taatgacat       120 ttaattgatt aaacatttat tcattaataa ttgtatgtta ctaacttcaa catttaataa      180
ttttgtttaa gatacgttta catcagagac tattaatatt tttacaggtt gtaactttaa      240
actttgtctt gaatcgaaca tgactataga ttttgggcaa acttaaagat aacaacattt      300
```

```
ccgttttttt tcaaattatt acaaatcaaa ctgatatatt agacacaaca cgattacacg      360
taatgaaaaa agaaaaagat aaaaagataa aagaagggat cgattctgtt tggtctggtt      420
tagtgagatt caaagttaag ctcttccttt caagacatgc cttcttaaac cgggaatgtg      480
aacgtttgta atgtagtccg tccagttaat gcttccaaca tcaaatccaa attctctctt      540
ctcgtcctct gacatattct ccattaatct ctggggtatt gctgttatca aatctgtaaa      600
agaaaccaaa aaaaaagat gaaaactttg cgggtaccgg ttttgtctgc tctaagaatt       660
agaatgttaa tgagttctgt cttaccttcc accatagaaa gtgtatggct cataaatagt      720
agcaaggtgt ttggcttgtt caacagattt cttgcatata aactttagct tctgcatcat      780
cttactatcc actgaactca taccactcat caacccactc cgttcttgag catctctcca      840
caaatgatcc gagaaatcat caacggaatt gaaaagtttc atcaaacgca ccataatagg      900 atcacccttta gagtccatgc atggagatgt tttgtagtgg ttataaagaa gctccgctaa     960
gtcttcgaaa accagcgggt ttatcgccga agaagcgatc tgatacacgt ttatttcagg     1020
ttcc                                                                  1024

<210> SEQ ID NO 46
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0111

<400> SEQUENCE: 46
cgattggatt tagtctatac attatagggc gcaagtttgt ggatttaaga attatataaa       60
aacttgaaat atatagttttt tatgcattct cctcttgtgt aatacataaa ccaaatatga    120
gataggttaa tctgtatttc agataatatt aaattccaaa caatattttt acttgttata    180
agaaggcaat taatatctct ctgttaatgg caagtggtac caagtagtat taaactatta    240
atgcaatgga agagtactgt tggaaattat aatcctctat cacacattca aacagatctc    300
ctgaaatctt ctcttccaaa cttgtacttc tctgatccaa atgtaggctc caaaatatag    360
acatttacca tttactaagt ccacaactcc tttcttgtct ccttcaaaaa tgactcttgt    420
gtaaccacca tatgactccg acagttcggc attgccatga tgagagctta aaaattcacc    480
ttcctgagca tttcaagtct tcactccctt agcttgacct gaaccaagat aaaatgcctt    540
tgtcgtcccg taatatccat cctgctttgg acggcatcat agttacattc gatccatcct    600
atttacaatg ttattttagt attaaaaaca tgacaataaa tttgttgtta aacatattca    660
aatacaatat gattggattt ataagtaatt gtaatatgaa atgtccttag taatatgtta    720
aaaaatacat agatacacac acgtactaaa agaggcaacg cgggagatgt cattagagga    780
agaactagga agcagagcgt tcatgcaaaa tgctaccaaa aacgttaatg caatatctca    840
actaatcagc acagtccatt tcatactgag aatgtaaaaa ccaatcagca tcgtccattt    900
tttcatctaa ttattttgtta actcttaatt ggccacaact tccaaccaca tgacgctctt    960
tctattccct ttatatattc ccatctcaaa tgttcttgga gacacaaaat atcataaaca   1020
tata                                                                 1024

<210> SEQ ID NO 47
<211> LENGTH: 996
<212> TYPE: DNA
<213> ORGANISM: Arabidopsis thaliana
```

```
<220> FEATURE:
<221> NAME/KEY: misc_feature
<222> LOCATION: (1)..(996)
<223> OTHER INFORMATION: Ceres Promoter YP0115

<400> SEQUENCE: 47
gtcgattgga tgatgaacat tctacatata taattattat gtttaagcac ttagacagca      60
taaattcttt ctaattatat aaatctaacc ttgttacatt gtacatctat aaattacttg     120
aagaaataac gagttctatt tcttttaaa aattaaaaat actataccat atctcagtga      180
ttaagttgaa ccaaaaggta cggaggagaa acaagcattt gattcttcct tattttattt     240
tattcatctc tcactaatga tggtggagaa aaaagaaaa tacctaacaa acaaatatat      300
attgtcatac aaaatatttt ctatattttt agtaattag tttatattcc tcacttttca      360
gggcttatat aagaaagtga gcaaacacaa atcaaaatgc agcagcaaat actatcatca    420
cccatctcct tagttctatt ttataattcc tcttcttttt gttcatagct ttgtaattat     480
agtcttattt ctctttaagg ctcaataaga ggaggtacta ttactacact tctctctact    540
tttacttgta ttttagcatt aaaatcctaa aatccgtttt aaattcaaaa ataaacttag    600
agatgtttaa tctcgattcg gttttcggc tttaggagaa taattatatg aaattagtat     660
ggatatcttt actagtttcc attcaaatga ttctgatttc aatctaatac tctcactctt     720
taattaaact atatgtagtg taatttcaca ctgttaaatt tctaccatgt catgtatatt    780
agagttgcat agaaaattgt aaaacatcca tttgaattcg aatgaaacaa aatgttttaa    840
aataaaattt tggtttttaa aagaaaaatc taaaactgaa ttatatcgtt taaccaagtt    900
gtaaaagtca taaaacgtag tatcttgtaa atcgctcttc cacggtccaa atagacttct     960
agtaataaac aagtaaaact aattttggtt tcttac                              996

<210> SEQ ID NO 48
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0117

<400> SEQUENCE: 48
gtcagtgagt cgattggatc acagtccttt atgataaaac aaactcataa ttattccacc     60
gacaacatgc gttttaaatt attttttctt aaattatatt atattatatt gatatcaacc    120
tagctaaaat aattcggatg gcgaaatcgg acaatttta atagaaaaaa tgggtatgaa      180
gatagtctat gattccgttc ttagcgacta gagggacctg ctcaaatctc ccgggtgata     240
cgcgatgtca agctcaatag aaccccacaa ccgacgagac cgagaaatcc ttgatttggg    300
ctagaagatt ttgaaataaa tttaatatat tctaagtaac ttgcttaaat tttttttcaa    360
actctaaaga cataactaac ataaagtaaa aaaaaaaag ttaatacatg ggaagaaaaa     420
aattaaacta atgattagct ctctaacgtg tttaatctcg tatcaagttt tttttttaaaa   480 attatattgc tattaaaaca ttgtactatt gtttctattt tgtttagcta ttattcttgt    540
gaaatgaaaa gttgtgttta ttcaattact aaatggcaat atttatcttg gaaaactata    600
cctctaattg gattaggccc tagacatcct ctttagctta ttgacgttaa aattattccc    660 aaactatta aagtttagta gtttgaaaga tgcatcaaga cctactcaga taggtaaaag     720
tagaaaacta cagttagtgt gattatattt taaaatatat aaaacaatct tattaaacta    780
```

-continued

| | |
|---|---|
| aatattcaag atatatactc aaatggaaga taaaaacatt tagtctgtta ccactaccag | 840 |
| cctagctagt cactaatagt cactttggaa ctgagtagat atttgcatct tgagttacca | 900 |
| tggactcaaa agtccaaaaa gagaccccga gtgaaaatgc taccaactta ataacaaaga | 960 |
| agcatttaca gcggtcaaaa agtatctata aatgtttaca caacagtagt cataagcacc | 1020 |
| attg | 1024 |

<210> SEQ ID NO 49
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0119

<400> SEQUENCE: 49

| | |
|---|---|
| taccaaaaat aaggagtttc caaaagatgg ttctgatgag aaacagagcc catccctctc | 60 |
| cttttcccct tcccatgaaa gaaatcggat ggtcctcctt caatgtcctc cacctactct | 120 |
| tctcttcttt ctttttttct ttcttattat taaccattta attaatttcc ccttcaattt | 180 |
| cagtttctag ttctgtaaaa agaaaataca catctcactt atagatatcc atatctattt | 240 |
| atatgcatgt atagaaaata aaaaagtgtg agtttctagg tatgttgagt atgtgctgtt | 300 |
| tggacaattg ttagatgatc tgtccatttt tttcttttt cttctgtgta taaatatatt | 360 |
| tgagcacaaa gaaaaactaa taaccttctg ttttcagcaa gtagggtctt ataaccttca | 420 |
| aagaaatatt ccttcaattg aaaacccata aaccaaaata gatattacaa aaggaaagag | 480 |
| agatattttc aagaacaaca taattagaaa agcagaagca gcagttaagt ggtactgaga | 540 |
| taaatgatat agtttctctt caagaacagt ttctcattac ccaccttctc cttttgctg | 600 |
| atctatcgta atcttgagaa ctcaggtaag gttgtgaata ttatgcacca ttcattaacc | 660 |
| ctaaaaataa gagatttaaa ataaatgttt cttctttctc tgattcttgt gtaaccaatt | 720 |
| catgggtttg atatgtttct tggttattgc ttatcaacaa agagatttga tcattataaa | 780 |
| gtagattaat aactcttaaa cacacaaagt ttctttattt tttagttaca tccctaattc | 840 |
| tagaccagaa catggatttg atctatttct tggttatgta ttcttgatca ggaaaaggga | 900 |
| tttgatcatc aagattagcc ttctctctct ctctctagat atctttcttg aatttagaaa | 960 |
| tctttattta attatttggt gatgtcatat ataggatcaa | 1000 |

<210> SEQ ID NO 50
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0120

<400> SEQUENCE: 50

| | |
|---|---|
| tagtttttga tttaatctac gttttctta atcataaatg ggtaattatt agttttgca | 60 |
| aaatcaaaat ccaaaaattg ttctaaacac tgcaaccatt taaggcctat atcactcaga | 120 |
| aaatttctgg tgggagaact aatcgttgt cctttctaaa tctcacatat tagaatttag | 180 |
| aattagtgtg ctacataaga atattagttc agctcggaac aactattttt tggtaaaaca | 240 |
| gagaacttaa acaaatgcat tatttttatca acatgcattt tgaattgaat ataaaatttc | 300 |
| ataattgtaa agacataaat tacataaaat tttacatgaa aaaatagata tagaaagaaa | 360 |

```
atgaaactaa ctgatgatat gctctctaaa ttttttaatc tcataacaag aattcaaatt    420
aattagttca tattttggt taatataaca tttacctgtc taagttggaa ctttcatttt    480
tttctgtttt gtttagtcag tattcttaat gtgaaacgga agttgaatt tattcaaact    540 taaattcaat agcattaatt aaaggcgaaa gctattatct ctacatgtgg ttcaaactag    600
acatccaatt taattagctt attgacgttg aaatgttttc caaaactact atagtttggc    660
aatttgaaag atgcatcaga actactcaga caggtaaaag tagaacctct agctgtgtga    720
attgtatgtt agtccataaa gaacatcttg taaacttcat acttaagata tatattacaa    780
tatatacttg aatggtagat aaaaacgatt agtctgattg ctagcatact cacaactatt    840
tggaaatgag taagatattg gcattctaga gttactacta tggagacaaa agtcgaataa    900
aagagacctc acgtgaaaat gttacgagct agtaaaaaaa gcatttacac taacggtaaa    960
aaaagtatct ataaatgttt acacaaggta gtagtcatt                           999
```

<210> SEQ ID NO 51
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0121

<400> SEQUENCE: 51

```
ttggattttt tttttgttga gtcagcagac catctaatct ctcttttcc accacagcct     60 gctttctatg aagcatttgg gcttacggtt gtggaatcaa tgacttgtgc actcccaacg    120
tttgctacct gtcatggtgg acccgcagag attatcgaaa acggagtttc tgggttccac    180
attgacccat atcatccaga ccaggttgca gctaccttgg tcagcttctt tgagacctgt    240
aacaccaatc caaatcattg ggttaaaatc tctgaaggag ggctcaagcg aatctatgaa    300
aggttggccc attctccttg acaggcttaa caatacaact tgtatcgctt caacaagatg    360
atggcttaat aaggattttt gcatgtatag gtacacatgg aagaagtact cagagagact    420
gcttaccctg gctggagtct atgcattctg gaaacatgtg tctaagctcg aaaggagaga    480
aacacgacgt tacctagaga tgttttactc attgaaattt cgtgatttgg ttagtgtaac    540
ccactgttat tcttttgatg tctacatcta ctttacttac attattcttt tcttcggttt    600
gcaggccaat tcaatcccgc tggcaacaga tgagaactga tcatgacagg gtaggattt     660 atttcctgca ctttctttag atcttttgtt tgtgttatct tgaataaaaa ttgttgggtt    720
ttgtttcctt cagtggtttg attttggact tatttgtgtt aatgttgttt tggctgttct    780
cttaatatca ataacaaata aatttactgg ttggtatcta agatctaaca atagttacta    840
tttttagagg taaagacacc aaccttgtta tattggtcag agagctaaaa ccttgacttg    900
ttgggaaaac aaaactctaa tgacagaaaa tctgacatga tgccttataa ttcacagcct    960
catgttctac ataaatccta acaatagcac tttgtttct                           999
```

<210> SEQ ID NO 52
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0128

<400> SEQUENCE: 52

```
gataaactga taatggaaaa gaacaaagaa accagttttt aactatttgc atatgtaatt        60
tatttgttgc aaattatatt tagttaaaat gtttcctcta tttatatata tatatatcag       120
tcaagcacta tgtataagaa atgtcaattt ataaattttt acatgtcctt aacagaaag        180
aaaatgaatt tttacatgtc attcatagag agtcactcgt ttatttctta tatagagaat       240
aacacactca catgcatatg catgcaatat gatacatttt atgacaaaga taatcaacgg       300
aaacggtcaa gacataattt gataaacaac ttgcacgatg cacagatctg atcaaatata       360
taactcttta acatatccaa aatattcaaa aagaaaaact cgatccaaac tagcaacatc       420
acgctcacgc ggtaggctaa aaatttatta atctccaaaa gtctttctta tgaacactgc       480
aaacacaaca acttgaaaag tcataggt ttagatgatg acgcgtattg gctatcgctt        540
accggagtgg ctcataaata caataaacaa tacgtaaaag tcaaagtcaa atatatttag       600
tcaactataa ccattaatcg ggcaaaacct ttagctgtca aaacaacgtg aaaacgatat       660
ttgtatatat catcaagaat cagtagataa gagaatgatt taatcccctg actattacaa       720
ttttggtgta ataaacagtc tctattggtt tttattcttt gttttaattt ctcatgacct       780
atagagagaa ttaggtagtt tcgaaaattg gctaatcaac ttttgaaaac tactgtctac       840
tttgcttaaa ttctctacac ttagtttcgg ataagataat tgtcggacta atagttaatc       900
ccttgacaat ctttgatatt ataaaaggtt tagttaatct cttctctata taaatattca       960
tacaccagct ttcaaaaata tataatccaa acaccaaaaa caaa                      1004
```

<210> SEQ ID NO 53
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0137

<400> SEQUENCE: 53

```
gtggcacatg ctgaaacccc gagcatctct ccggaagaca cgcgtcgttc gctccaaaga        60
aaacagtcac agctgccgga gaatctccgc cgtcttcttc tgccaccgga aaaactctct       120
ccaccacttt cagtgcccac ctcgtgttat atccactgta tcctcgtagc accatatcag       180
cctaataaaa ttttatgtat caaattttaa gacatagccg aaactacact atactagaca       240
ataataatat gatttgtttc ctgaaaaatt atggtttcat gagaaacatt aatcatctat       300
aaaacaaatt agctatggca tcgaagagtt atcaatcaaa actgatgaat ctttacttaa       360
tatatacaac atatctttac cttgcggcgg agaagatcgg cgagagaagc accccagcca       420
ccgtcactaa aggattcttc agtgatggaa tcaccaaaga gaaaaacctt ccgtctcatc       480
atcttccaca caatcttctt gagaaaatct gagagataag aaaggtgtag tggttttgct       540
gaagtgatcg tgtttgattt agtaaagaaa tgctttatt attgttgggg gaaacataaa        600
taaataaagt aaaagtggat gcactaaatg ctttcaccca ctaatcaccg acctttcatg       660
gtttattgtg aaatacactc atagatagac atacaatacc ttatgtacgt aaataacatt       720
ttatttgtcg acacttatgt aagtaacgca tagattattt tctatgtgat tgccactctc       780
agactctcag tttcaaccaa taataacaat aactacaaca acattaatca taaacatatg       840
ctctggttta caattaaagc ttagattaag aaactgtaac aacgttacag aaaaaaaatg       900
```

```
ttatttacgt tttgtaagat tagtctctag aatcatcacc gttttttata tattaatgat    960
tctttcttat atataaaacc tttctcgaaa tacccatgaa a                       1001

<210> SEQ ID NO 54
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter YP0143

<400> SEQUENCE: 54
atacaacaga tggcagatat cgagttaaat acgtgaatca gccgttacga tattttaaaa     60
ctagaaaatt atttaaaaat attgcaaaat accatttaat ttcattgttc ataaaaaaaa    120
gaaattcaaa aacttaaaaa ctgattcaaa aatttggatt aattctcatt aacagtcttc    180
aacactacaa caacatgttt ctaatttatt ttatatttta ataattaaac aatatatacg    240
tctgcacatt gttgctccga cataatctag tataaaaata gttgcagcat atgtgaaaag    300
caagcagcat ttatcactca atactttaa ttttatctgt tgtatgtatt aaggttttgt     360
agctttaaga aaacgcttat aatataaaat aacttctaaa agatatttca tgcgtataca    420
ataaatattt gtgaaaaaac atttcgaaaa cgtgtacaat atataaacta ttgtgttatc    480
ttttgacatt caaacaaatg ttgacaatgt aatttttatcc atgatatgat tggccaatta   540
gctgcgaggt aaaaatccgt atacgagtaa aagtaagata aaatttcgca agaagatttt   600
tagcaggaaa tctaagacaa gtgtcatgaa cgtgtcaatc aacaaacgaa aaggagaatt    660
atagaatcca gattcgacgt accacattaa taaatatcaa aacattttat gttattttat    720
ttttgctctg gcagttacac tcttttttcat tgctccaata aaaaaatcac tcgcatgcat    780
gcatatatat acaccatagt aaaactccgcc tcttcttcat tttaaaagta tcagtttaca   840
ctgacacaat ccttaactat tttcctttgt tcttcttcat ctttattaca catttttttc    900
aaggtaacaa ataatcttt taagtcactt ttatactctt taaatcttag attgatatat    960
gaatgcatgt taatatttca agatttatag gtctaccaaa c                       1001

<210> SEQ ID NO 55
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter YP0144

<400> SEQUENCE: 55
aaacgttgca agattattga ttgtgagaaa gagtgctcaa ggtagtactg atttctgtaa     60
agctcacggt ggtgggaaac gatgttcttg gggagatggg aaatgtgaga aaatttgcta    120
gaggaaagaa gcggtttatg cgctgcgcat aacactatta tgtctcggga gaacaaagat    180
ggaagcaaga gcggtttgat tggaccggga ctctttagtg gccttgtttt tggctctact    240
tctgatcatt ctcagtctgg agctagcgct gtctctgatt gtactgattc tgttgaacga    300
atacagtttg agaataggca gaagaacaag aagatgatga taccgatgca ggttctagta    360
ccttcatcaa tgaaatctcc aagtaattca catgaaggag aaacaaacat ctatgacttc    420
atggttccgg aggagagagt tcacggcggt gggctagtaa tgtctttact tggtggctcc    480
attgatcgaa actgaaagcc atttatggta aaagtgtcac attctcagca aaaacctgtg    540
```

```
taaagctgta aaatgtgtgg gaatctccga atctgtttgt agccggttac gttatgctgg      600
atcaaaaact caagatttgt tggatattgt tatgctggat cggtggtgaa accacttccc      660
ggttgctaaa taaataaacg ttttgtttt ataatctttt tcactaaacg gcagtatggg      720
cctttagtgg gcttccttta agcgaccaat acaatcgtcg caccggaatc tactaccatt      780
tataggttta ttcatgtaaa acctcggaaa atttgagagc cacaacggtc aagagacaaa      840
aacaacttga agataaaggg ataaggaagg cttcctacat gatggacaac atttctttcc      900
acacaaattc tcataataaa aatcttataa tacaaatact tacgtcataa tcattcaatc      960
tagtccccat gttttaaggt cctgtttctt gtctgataca aat                     1003
```

<210> SEQ ID NO 56
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter YP0156

<400> SEQUENCE: 56

```
ttggtttgca ttgtgaagat ttgtattaac tatagaacat tgaattgatg gtgttaagtt       60
cttacacaag cgtgcttctc ggtttgaact gtttcttttg tatgttgaat cagagcttag      120
tttataggaa ccagagtatc tacttagtca ttctctgatg ctaagtgcta aggttctacc      180
tagttgccct ctaggccctt atgttattga taacttatga agctatttga acacttgatt      240
cttaggagac ctaagttggt acagccagat agagtgtatg ttcttgttct ctatgtgaca      300
ggatcaagct gccacacata gttcaagggt atgctctgtg tgggtttgct cagattgagg      360
acaaatctat acaaggaagt agagtctttg acattttgat gttgtatgat aagaagaaga      420
aaggagagta ataaagaaag agaaaaggga aacagaaaca cgtgggagaa catcccaaag      480
aggaagcaca cgcggatctt catgcaaagc tccccgattc tcccatgtgg tcccttctc       540 cctttgtccc cctcctcttt cttctttcct cattttactc cttttttac cattatacaa      600 cgaatctttt ttatcataat ttttggttt tggtttattt tccaataaca ctttcttggt      660
tacttcccat tctcactttt tcatataaga aactcacttt gggaaactta tgtttgagaa      720
tgacaagtct ttttagagaa agtgatgtaa caaatctaaa gtgattatat aataaccttg      780
cacaatgttt ttgatttttt gtaagattcg aatattaggt ttattattcg tagggaataa      840
acttactttc aaaagcgttc ataagttaat actttcatat atgatcataa gtacggacac      900
tattgttttt tgtttgtttg tgtttattct aaaagaaagt agcttttaat tgaaatgtcc      960
tcggaggcac agtttaaagt tcgagtgtaa cagtttctaa ggca                    1004
```

<210> SEQ ID NO 57
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0158

<400> SEQUENCE: 57

```
ttattagatt aatagattgc attgcattgc ttgtgctttc aatttacaaa ttgtctccca       60
actccatcga cacatctctt tttgtgtata taagattcag acttgttata ttttttttat      120
aaatatgtta ttagcatctt aagttaaatt gatttttat atctgcatta aggattacac      180
```

```
gactatattt gcgattgtgt gttggttaaa atataattta ggattgtctt taactacatt        240
taggattata tgactatatt tggttaaata taaaatctag ctgtgattat tagtattcaa        300
aaataagtag cctaaccaat taaaacaacg gctattgggg caaattagaa cattttagtg        360
tgtccaaaat ataatggtca ttaggtcata ttcctcctag cttcatcgca gcataattga        420
atgattgcct tatttagaag agcttttcca ctttcccaaa atctaggtgg gatcttttg         480 ttttgacctt cattttctt gtttaccatt tttagctaaa ttatttacga ttacaaaaga        540
tatcaaaagt tggatcataa tacaatttat agacttactg tagaaaattc gtatgtacaa        600
gtacaacaaa ttcttcataa taaattttga aaattctatt acaaatgttg taagaaatag        660
aatttgaaat atatataaac taaggagaaa aaaaagaga acatgcattg ctctagtcag         720
agtggaccaa catcaacgag ataagataac ataaaaacca actcaccata actaaaaaca        780
tcccaagaga tccaacgatt catatcaaac acaaaaacat cgaacgatca gatttaaacc       840
atctctggta tctccaaaac acaaacactt ttttttttct tttgtctgaa tggaacaaaa        900
gcatgcgaca tctctgtgtc tttatcttct ctctcctctt cttgaaaaac tgaacctta         960 attctttctt cacatctcct ttagctttct gaagctgcta                              1000
```

<210> SEQ ID NO 58
<211> LENGTH: 1005
<212> TYPE: DNA
<213> ORGANISM: Arabidopsis thaliana
<220> FEATURE:
<221> NAME/KEY: misc_feature
<222> LOCATION: (1)..(1005)
<223> OTHER INFORMATION: Ceres Promoter YP0188

<400> SEQUENCE: 58

```
gattggtatg aaatttcgga gaccaacaaa aaaaacttta ttgagcttgg agtgaagcta         60
tatatatggg gcaagatcat aatatgttta tatcggcctt ttcgttaact gaaaataata        120
gttttgagaa atatatcaaa tggtaaacag acatcatctt tgaaaaatac catcaatgaa       180
gttaatattg ttattggcat atggtttacc catcttaatt ttaatgcaac caaacaaaca        240
agaaacaaaa actgtataag atacaaggtg ttttacgatt ttccgtctta aaaccgaaat        300 attttgttc ctacgacttt aaacggactt tgcttaagtt gtgtgcatgt aagctcgtcg        360
tccctcgatt gtcatcaaca ttcaccaata tcagcctcta tcacacgagt gaaggtggtg       420
attcggctta atgaaaacag agaaatattt caatatgatt cctattaaat tttaaatctt      480
ttttctcaat ctctagattt tcattaaaag catcatgatt ttttttccact atgttcatat     540 atctctatca cagttttagg tacattgtag aaattggata agatacgtca tacgtctaac       600
atgaatttgg tctagcaagg aaggtttgag ataataagtg aaaagaaaac acaagataat       660
aaattataat ttataaatgc tttatagtat tgaaaaataa gatgattttt tttttttta        720 ataccggatt ggctgatcca cttatgatga ctcaaatgtt attaagtttc aagacaattt      780
atgatgacac aaatcacaat gagtcaatag tagccacgaa gccagaaaaa aaaaatgtac       840
tacaaaaaga taatgatagt acaaaatgat acgtcgtact gccacatgta cgacacaact      900
cgattaccaa aaagcagagc catccaacca taaaactcaa aacacacaga ttccactggc       960
gtgtgctctc ctcacttcac tcgtccttga aacttgaggt actga                      1005
```

<210> SEQ ID NO 59
<211> LENGTH: 1002
<212> TYPE: DNA
<213> ORGANISM: Arabidopsis thaliana

```
<220> FEATURE:
<221> NAME/KEY: misc_feature
<222> LOCATION: (1)..(1002)
<223> OTHER INFORMATION: Ceres Promoter YP0190

<400> SEQUENCE: 59
taaatagtga cattggtaag aagaaaaaaa acactattaa atagtgaaaa aatggtttat    60
aactctctta attaacatta cttattattg ctagcaccta aaatctccca caaatatttt   120
gttgtaaaac acaaatttac aaaatgattt tgttttaaa ttagtaacac atgttcatat    180
atacgttaat aagaacatac cctatatgat tttatataaa aaaatttctt tgagacgtct   240
tattcttttt tctttaataa tatgcaattg tgagagtttg gatttgaatg gtagcattag   300
aagcaaactt gaaccaaaca tatttcatga agtcaaactt gaaccaatgt gatcactaat   360
cacagtgttc gcagtgtaag gcatcagaaa atagaagaag ggacatagct atgaatcata   420
taatcttgac acatgtttta taggttttag gtgtgtatgc taacaaaaaa tgagacagct   480
ttcttctaat agacttaata tttgggctaa atgtaccaca gttgtgaatt tcttacaaaa   540
atgggccgag ctacaaaaaa ctacaggccc actctcaact cttatcaaac gacagcgttt   600
tactttttta aaagcacaca cttttgttt ggtgtcggtg acggtgagtt tcgtccgctc    660
ttcctttaaa ttgaagcaac ggttttgatc cgatcaaatc caacggtgct gattacacaa   720
agcccgagac gaaacgttg actattaagt taggttttaa tctcagccgt taatctacaa    780
atcaacggtt ccctgtaaaa cgaatcttcc ttccttcttc acttccgcgt cttctctctc   840
aatcacctca aaaaatcga tttcatcaaa atattcaccc gcccgaattt gactctccga   900
tcatcgtctc cgaatctaga tcgacgagat caaaacccta gaaatctaaa tcggaatgag   960
aaattgattt tgatacgaat tagggatctg tgtgttgagg ac                     1002

<210> SEQ ID NO 60
<211> LENGTH: 995
<212> TYPE: DNA
<213> ORGANISM: Arabidopsis thaliana
<220> FEATURE:
<221> NAME/KEY: misc_feature
<222> LOCATION: (1)..(995)
<223> OTHER INFORMATION: Ceres Promoter YP0212

<400> SEQUENCE: 60
agtcgattgg tacactctta atttaattag agtaagagat caacaaaaat atagaattt    60 ctttatatcg aagtgctacg accttatata tatagaaaaa aaagcatagg tgaatctcta   120
aattgagatt gtgctgtagt aaacatatta agttttagt ttttttaaga aatgaatctt    180
tttgttgatt aattcaaact agtagtcatt aagattccgg agattccaat ttagaaaagt   240
caaagattca agaacaagt ccaggtccac atgttgaatc cgattcatca tccactcatc    300
cttcatatct tcctccaccg tctccgccca aaaaatcaat aacaataaaa aatcctaaaa   360
aaacatattt gattttgaaa aaactttatc atatattata ttaattaaat agttatccga   420
tgactcatcc tatggtcagg gccttgctgt ctctgacgtc cttaattatc attatttta    480 aatttgtctc tctcagaaaa ttacgccaca atcttcctct ttcccttttc cgaaaacagc   540
taatatttgt ggacctaaac taaataacgt agcctctaga ttttatataa ttactaatac   600
tatatgctac tacttgttat tatttactcc aatcatatat gataccaatc aagaatcact   660
acataagtag aaaactttgc aatgagtcca ttaattaaaa ttaagaataa acttaaaatt   720
ttatggtatt ttaagattcc ctttggattg taatgacaag aaatcagcaa attagtcgta   780
```

| | |
|---|---|
| actcgtaaga ataaacaaga tcaattttta ctttctttac aaagattccg ttgtaatttt | 840 |
| agaaattttt ttttgtcact gttttttttat agattaattt atctgcatca atccgattaa | 900 |
| gaagtgtaca catgggcatc tatatatatc taacaggtaa aacgtgtatg tacatgcata | 960 |
| aggttttacg tgcttctata aatatatgtg gcagt | 995 |

<210> SEQ ID NO 61
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter YP0214

<400> SEQUENCE: 61

| | |
|---|---|
| ccagtcgatt ggcgcctcgc atgcctatca tatttaaccg tcaataatgg atttggcggt | 60 |
| tttggtaggc cgggtcaacc ggattaaaag aaaacggttt ggagtccttc cttgcaattg | 120 |
| aattttcaca cattcgggtt ttgtgatttc tctgtcataa tgggcccggc acatatggtt | 180 |
| cataacccat gtgggcctat ggtataattt ttccaattaa aactattgtt aggtcgataa | 240 |
| aacaaaaaac aataaaaacg agtggaatac acataccaaa agaatgtga tgaacattag | 300 |
| taattttatt ttgatggtta atgaaaaaca aaataaatgc atcttggcat cttccgttgg | 360 |
| aaagcgcaaa tagggcagat tttcagacag atatcactat gatgggggt gagagaaaga | 420 |
| aaacgaggcg tacctaatgt aacactactt aattagtcgt tagttatagg actttttttt | 480 |
| tgtttgggcc tagttatagg atcataaggt aaaaatgaag aatgaatatt agattagtag | 540 |
| gagctaatga tggagttaag tatgcacgtg taagaactgg gaagtgaaac ctcctgtatg | 600 |
| gtgaagaaac tatacaacaa agccctttgt tggtgtatac gtattaattt ttattcttt | 660 |
| atcacaagcg atacgtatct taagacataa taaatatata tcttactcat aataaatatc | 720 |
| ttaagatata tatacagtat acacctgtat atatataata aataggcata tagtagaaat | 780 |
| taatatgagt tgttgttgtt gcaaatatat aaatcaatca aaagatttaa acccaccat | 840 |
| tcaatcttgg taagtaacga aaaaaaggg aagcaagaag aaccacagaa aaggggcta | 900 |
| acaactagac acgtagatct tcatctgccc gtccatctaa cctaccacac tctcatcttc | 960 |
| ttttttcccgt gtcagtttgt tatataagct ctcactctcc ggtatatttc cccattgcac | 1020 |
| tgga | 1024 |

<210> SEQ ID NO 62
<211> LENGTH: 911
<212> TYPE: DNA
<213> ORGANISM: Arabidopsis thaliana
<220> FEATURE:
<221> NAME/KEY: misc_feature
<222> LOCATION: (1)..(911)
<223> OTHER INFORMATION: Ceres Promoter YP0263

<400> SEQUENCE: 62

| | |
|---|---|
| atctagctgt ggattccacc aaaattctgg cagggccatg atctaaaaac tgagactgcg | 60 |
| cgtgttgttt tgcagtgatt tgtatttcat atttgcacca tcctacacag tccacttggt | 120 |
| atcgtaacca aacataagga gaacctaatt acattattgt tttaatttcg tcaaactggt | 180 |
| ttttaccttt tagttacata gttgattctt catttgtttt agtagttatg gagcacaata | 240 |
| atgtgcaaca agaaagatc atagtggatt aatatgttga gaggtcagaa attcttggtt | 300 |
| aacaaaaaaa agttacaagg actgagattt tgggtgggag aaagccatag cttttaaaac | 360 |

```
atgattgaac ttaaaagtga tgttatggtt tgaggggaaa aaggttgatg tcaactaaga      420
tagttgaagt aatgtcttaa actaaagtaa accaccggtc caaccgtggt ccggaagcat      480
ctctggtatg atttatccta aaaatcaaaa tagtagaaac atactttaaa tatatacatt      540
gatcggacga aaattgtaaa ctagtatagt ttcaaaaact agttgaacag gttatgtacc      600
ttaaacattt atttcaaact taaacactaa agaacatata tgaatagaag tttatataaa      660
ttactatata tctaccataa atctcttata attatgatgt cacgatgagg aagtgttgaa      720
acgttaaaat gccaaaatat aagcatgcga cggaattttg gcagaagatt gtagagttgt      780
aatctgtcgc aatcattact cgtgctagca tttttcattt tcccttcatt tgtggataac      840
gcacgatata acattctaca caccaacaag attctataaa aacgcaaagg ttgtctccat      900
agaatatcgt c                                                           911
```

<210> SEQ ID NO 63
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0275

<400> SEQUENCE: 63

```
aaacattaat atgtagtaac tatgggcgta tgctttactt tttaaaatgg gcctatgcta       60
taattgaatg acaaggatta aacaactaat aaaattgtag atgggttaag atgacttatt      120
tttttactta ccaatttata aatgggcttc gatgtactga aatatatcgc gcctattaac      180
gaggccattc aacgaatgtt ttaagggccc tatttcgaca ttttaaagaa cacctaggtc      240
atcattccag aaatggatat tataggattt agataatttc ccacgtttgg tttatttatc      300
tattttttga cgttgaccaa cataatcgtg cccaaccgtt tcacgcaacg aatttatata      360
cgaaatatat atattttttca aattaagata ccacaatcaa acagctgtt gattaacaaa      420 gagattttt ttttttggtt ttgagttaca ataacgttag aggataaggt ttcttgcaac      480
gattaggaaa tcgtataaaa taaaatatgt tataattaag tgttttattt tataatgagt      540
attaatataa ataaaacctg caaaaggata gggatattga ataataaaga gaaacgaaag      600
agcaatttta cttctttata attgaaatta tgtgaatgtt atgtttacaa tgaatgattc      660
atcgttctat atattgaagt aaagaatgag tttattgtgc ttgcataatg acgttaactt      720
cacatataca cttattacat aacatttatc acatgtgcgt ctttttttt tttttacttttg     780 taaaatttcc tcactttttaa gacttttata acaattacta gtaaaataaa gttgcttggg    840
gctacaccct ttctccctcc aacaactcta tttatagata acattatatc aaaatcaaaa      900
catagtccct ttcttctata aaggttttt cacaaccaaa tttccattat aaatcaaaaa       960
ataaaaactt aattagtttt tacagaagaa aagaaaaca                             999
```

<210> SEQ ID NO 64
<211> LENGTH: 981
<212> TYPE: DNA
<213> ORGANISM: Arabidopsis thaliana
<220> FEATURE:
<221> NAME/KEY: misc_feature
<222> LOCATION: (1)..(981)
<223> OTHER INFORMATION: Ceres Promoter YP0285

-continued

```
<400> SEQUENCE: 64
gggattatat atgatagacg attgtatttg cgggacattg agatgtttcc gaaaatagtc      60
atcaaatatc aaaccagaat ttgatgtgaa aacactaatt aaaacatata attgacaact     120
agactatatc atttgttaag ttgagcgttg aaagaaaatg aaagagtgta gactgtagta     180
cgtatgagtt tcccaaaaga tggtgcttga atattattgg gaagagactt tggttggttc     240
ggttgaatga agattttac ctgccatgtt gatagagaaa ggcaaataaa tgtaggggtc      300
gatgtctaac gtaaagactg gatcaaccaa gagtcctcct cctcgtcttc accaaaaaaa     360
aagagtcctc ctcgtggaaa cttatttctt ctccagccaa gatctcatct catctcttca     420
ctctatgaaa tataaaggaa tcttatggtt tttctaaaaa ctatagtacg tctatatacc     480
aaaggaaaca atataaaatc agttaatctg ataaattttg agtaaataat aaagttaact     540
ttgtacttac ctatatcaaa ctaattcaca aaataaagta ataataacaa agaatttta      600 gtagatccac aatatacaca cacactatga gaaatcataa tagagaattt taatgatttt     660
gtctaactca tagcaacaag tcgctttggc cgagtggtta aggcgtgtgc ctgctaagta     720
catgggctct gcccgcgaga gttcgaatct ctcaggcgac gtttcttttg ttttcggcca     780
taaggaaaaa agcccaatta acacgtctcg cttataagcc cataaagcaa acaatgggct     840
gtctctgtct cactcacaca cgcgttttcc tacttttttga ctattttttat aaccggcggg    900 tctgacttaa ttagggtttt ctttaataat cagacactct ctcactcgtt tcgtcaacat     960
tgaacacaga caaaaccgcg t                                                981

<210> SEQ ID NO 65
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter YP0286

<400> SEQUENCE: 65 gaaacaatc ataggttacg ctattatcat cgaaaggtat gtgatgcata ttcccattga       60
accagatttc catatatttt atttgtaaag tgataatgaa tcacaagatg attcaatatt     120
aaaaatgggt aactcacttt gacgtgtagt acgtggaaga atagttagct atcacgcata     180
catatatcta tgaataagtg tgtatgacat aagaaactaa aatatttacc taaagtccag     240
ttactcatac tgatttcatg catatatgta ttatttattt attttttaata aagaagcgat     300 tggtgttttc atagaaatca tgatagattg ataggtattt cagttccaca aatctagatc     360
tgtgtgctat acatgcatgt attaattttt tcccttaaa tcatttcagt tgataatatt     420
gctctttgtt ccaactttag aaaaggtatg aaccaacctg acgattaaca agtaaacatt     480
aattaatctt tatatgagat aaaaccgagg atatatatga ttgtgttgct gtctattgat     540
gatgtgtcga tattatgctt gttgtaccaa tgctcgagcc gagcgtgatc gatgccttga     600
caaactatat atgtttcccg aattaattaa gttttgtatc ttaattagaa taacattttt     660
atacaatgta atttctcaag cagacaagat atgtatccta tattaattac tatatatgaa     720
ttgccgggca cctaccagga tgtttcaaat acgagagccc attagtttcc acgtaaatca     780
caatgacgcg acaaaatcta gaatcgtgtc aaaactctat caatacaata atatatatttt    840 caagggcaat ttcgacttct cctcaactca atgattcaac gccatgaatc tctatataaa     900
```

-continued

```
ggctacaaca ccacaaagga tcatcagtca tcacaaccac attaactctt caccactatc    960
tctcaatctc tcgtttcatt tcttgacgcg tgaaaa                              996

<210> SEQ ID NO 66
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0337

<400> SEQUENCE: 66 taatttttt attttgaaa ctaacactta ttagtttagg tttccatcac ctatttaatt       60
cgtaattctt atacatgcat ataatagaga tacatatata caaatttatg atcattttg     120 cacaacatgt gatctcattc attagtatgc attatgcgaa aacctcgacg cgcaaaagac    180
acgtaatagc taataatgtt actcatttat aatgattgaa gcaagacgaa acaacaaca    240 tatatatcaa attgtaaact agatatttct taaaagtgaa aaaaaacaaa gaaatataaa    300
ggacaatttt gagtcagtct cttaatatta aaacatatat acataaataa gcacaaacgt    360
ggttacctgt cttcatgcaa tgtggacttt agtttatcta atcaaaatca aataaaagg     420 tgtaatagtt ctcgtcattt ttcaaatttt aaaaatcaga accaagtgat ttttgtttga    480
gtattgatcc attgtttaaa caatttaaca cagtatatac gtctcttgag atgttgacat    540
gatgataaaa tacgagatcg tctcttggtt ttcgaatttt gaactttaat agttttcttt    600
tttagggaaa ctttaatagt tgtttatcat aagattagtc acctaatggt tacgttgcag    660
taccgaacca attttttacc cttttttcta aatgtggtcg tggcataatt tccaaaagag    720
atccaaaacc cggtttgctc aactgataag ccggtcggtt ctggtttgaa aaacaagaaa    780
taatctgaaa gtgtgaaaca gcaacgtgtc tcggtgtttc atgagccacc tgccacctca    840
ttcacgtcgg tcattttgtc gtttcacggt tcacgctcta gacacgtgct ctgtccccac    900
catgactttc gctgccgact cgcttcgctt tgcaaactca aacatgtgtg tatatgtaag    960
tttcatccta ataagcatct cttaccacat taattaaaaa                         1000

<210> SEQ ID NO 67
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0356

<400> SEQUENCE: 67
ttagttcatt gaaacgtcaa cttttactt gcaaccactt tgtaggacca ttaactgcaa      60
aataagaatt ctctaagctt cacaaggggt tcgtttggtg ctataaaaac attgttttaa    120
gaactggttt actggttcta taaatctata aatccaaata tgaagtatgg caataataat    180
aacatgttag cacaaaaaat actcattaaa ttcctaccca aaaaaaatct ttatatgaaa    240
ctaaaactta tatacacaat aatagtgata caaagtaggt cttgatattc aactattcgg    300 gatttttctgg tttcgagtaa ttcgtataaa aggtttaaga tctattatgt tcactgaaat    360
cttaactttg ttttgtttcc agttttaact agtagaaatt gaattttta aaaattgtta    420 cttacaataa aatttgaatc aatatcctta atcaaaggat cttaagacta gcacaattaa    480
aacatataac gtagaatatc tgaaataact cgaaatatc tgaactaagt tagtagtttt    540
```

| aaaatataat cccggtttgg accgggcagt atgtacttca atacttgtgg gttttgacga | 600 |
| tttttggatcg gattgggcgg gccagccaga ttgatctatt acaaatttca cctgtcaacg | 660 |
| ctaactccga acttaatcaa agattttgag ctaaggaaaa ctaatcagtg atcacccaaa | 720 |
| gaaaacattc gtgaataatt gtttgctttc catggcagca aaacaaatag gacccaaata | 780 |
| ggaatgtcaa aaaaagaaa gacacgaaac gaagtagtat aacgtaacac acaaaaataa | 840 |
| actagagata ttaaaaacac atgtccacac atggatacaa gagcatttaa ggagcagaag | 900 |
| gcacgtagtg gttagaaggt atgtgatata attaatcggc ccaaatagat tggtaagtag | 960 |
| tagccgtcta tatcatccat actcatcata acttcaacct | 1000 |

<210> SEQ ID NO 68
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0374

<400> SEQUENCE: 68

| aagacacccg taaatgttgt catgtagaag aaactagaaa cgttaaacgc atcaaatcaa | 60 |
| gaaattaaat tgaaggtaat ttttaacgcc gcctttcaaa tattcttcct aggagaggct | 120 |
| acaagacgcg tatttctttc gaattctcca aaccattacc attttgatat ataataccga | 180 |
| catgccgttg ataaagtttg tatgcaaatc gttcattggg tatgagcaaa tgccatccat | 240 |
| tggttcttgt aattaaatgg tccaaaaata gtttgttccc actactagtt actaatttgt | 300 |
| atcactctgc aaaataatca tgatataaac gtatgtgcta tttctaatta aaactcaaaa | 360 |
| gtaatcaatg tacaatgcag agatgaccat aaaagaacat taaaacacta cttccactaa | 420 |
| atctatgggg tgccttggca aggcaattga ataaggagaa tgcatcaaga tgatatagaa | 480 |
| aatgctattc agtttataac attaatgttt tggcggaaaa ttttctatat attagacctt | 540 |
| tctgtaaaaa aaaaaaaatg atgtagaaaa tgctattatg tttcaaaaat ttcgcactag | 600 |
| tataatacgg aacattgtag tttacactgc tcattaccat gaaaaccaag gcagtatata | 660 |
| ccaacattaa taaactaaat cgcgatttct agcaccccca ttaattaatt ttactattat | 720 |
| acattctctt tgcttctcga aataataaac ttctctatat cattctacat aataaataag | 780 |
| aaagaaatcg acaagatcta aatttagatc tattcagctt tttcgcctga gaagccaaaa | 840 |
| ttgtgaatag aagaaagcag tcgtcatctt cccacgtttg gacgaaataa aacataacaa | 900 |
| taataaaata ataaatcaaa tatataaatc cctaatttgt ctttattact ccacaatttt | 960 |
| ctatgtgtat atatataccc acctctctct tgtgtatttg | 1000 |

<210> SEQ ID NO 69
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter YP0377

<400> SEQUENCE: 69

| tataaaccat tcctataaca ccatatttaa acataacaat gaattgcttg gatttcaaac | 60 |
| tttattaaat ttggatttta aattttaatt tgattgaatt ataccccctt aattggataa | 120 |
| attcaaatat gtcaactttt ttttttgtaag attttttttat ggaaaaaaaa attgattatt | 180 |

-continued

```
cactaaaaag atgacaggtt acttataatt taatatatgt aaaccctaaa aagaagaaaa      240
tagtttctgt tttcactttta ggtcttatta tctaaacttc tttaagaaaa tcgcaataaa      300
ttggtttgag ttctaacttt aaacacatta atatttgtgt gctatttaaa aaataattta      360
caaaaaaaaa aacaaattga cagaaaatat caggttttgt aataagatat ttcctgataa      420
atatttaggg aatataacat atcaaaagat tcaaattctg aaaatcaaga atggtagaca      480
tgtgaaagtt gtcatcaata tggtccactt ttctttgctc tataacccaa aattgaccct      540
gacagtcaac ttgtacacgc ggccaaacct ttttataatc atgctattta tttccttcat      600
ttttattcta tttgctatct aactgatttt tcattaacat gataccagaa atgaatttag      660
atggattaat tctttttccat ccacgacatc tggaaacact tatctcctaa ttaaccttac      720 tttttttta gtttgtgtgc tccttcataa aatctatatt gtttaaaaca aaggtcaata      780
aatataaata tggataagta taataaatct ttattggata tttctttttt taaaaaagaa      840
ataaatcttt tttggatatt ttcgtggcag catcataatg agagactacg tcgaaaccgc      900
tggcaaccac ttttgccgcg tttaatttct ttctgaggct tatataaata gatcaaaggg      960
gaaagtgaga tataatacag acaaaacaag agaaaaga                              998
```

<210> SEQ ID NO 70
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0380

<400> SEQUENCE: 70

```
acaagtacca ttcacttttt tacttttcaa tgtatacaat catcatgtga taaaaaaaaa       60
aatgtaacca atcaacacac tgagatacgg ccaaaaaatg gtaatacata aatgtttgta      120
ggttttgtaa tttaaatact ttagttaagt tatgatttta ttatttttgc ttatcactta      180
tacgaaatca tcaatctatt ggtatctctt aatcccgctt tttaatttcc accgcacacg      240
caaatcagca aatggttcca gccacgtgca tgtgaccaca tattgtggtc acagtactcg      300 tcctttttt ttctttttgta atcaataaat ttcaatccta aaacttcaca cattgagcac      360
gtcggcaacg ttagctccta aatcataacg agcaaaaaag ttcaaattag ggtatatgat      420
caattgatca tcactacatg tctacataat taatatgtat tcaaccggtc ggtttgttga      480
tactcatagt taagtatata tgtgctaatt agaattagga tgaatcagtt cttgcaaaca      540
actacggttt catataatat gggagtgtta tgtacaaaat gaaagaggat ggatcattct      600
gagatgttat gggctcccag tcaatcatgt tttgctcgca tatgctatct tttgagtctc      660
ttcctaaact catagaataa gcacgttggt ttttccacc gtcctcctcg tgaacaaaag      720
tacaattaca ttttagcaaa ttgaaaataa ccacgtggat ggaccatatt atatgtgatc      780
atattgcttg tcgtcttcgt tttctttta atgtttacac cactacttcc tgacacgtgt      840
ccctattcac atcatccttg ttatatcgtt ttacttataa aggatcacga acaccaaaac      900
atcaatgtgt acgtcttttg cataagaaga aacagagagc attatcaatt attaacaatt      960
acacaagaca gcgagattgt aaaagagtaa gagagagag                             999
```

<210> SEQ ID NO 71
<211> LENGTH: 1000
<212> TYPE: DNA
<213> ORGANISM: Arabidopsis thaliana

```
<220> FEATURE:
<221> NAME/KEY: misc_feature
<222> LOCATION: (1)..(1000)
<223> OTHER INFORMATION: Ceres Promoter YP0381

<400> SEQUENCE: 71
cacggtcaaa gtattgctaa catggtcatt acattgaaaa agaaaattaa ttgtctttac      60
tcatgtttat tctatacaaa taaaaatatt aaccaaccat cgcactaaca aaatagaaat     120
cttattctaa tcacttaatt gttgacaatt aaatcattga aaaatacact taaatgtcaa     180
atattcgttt tgcatacttt tcaatttaaa tacatttaaa gttcgacaag ttgcgtttac     240
tatcatagaa aactaaatct cctaccaaag cgaaatgaaa ctactaaagc gacaggcagg     300
ttacataacc taacaaatct ccacgtgtca attaccaaga gaaaaaaga gaagataagc      360
ggaacacgtg gtagcacaaa aaagataatg tgatttaaat taaaaaacaa aaacaaagac     420
acgtgacgac ctgacgctgc aacatcccac cttacaacgt aataaccact gaacataaga     480
cacgtgtacg atcttgtctt tgttttctcg atgaaaacca cgtgggtgct caaagtcctt     540
gggtcagagt cttccatgat tccacgtgtc gttaatgcac caaacaaggg tactttcggt     600
attttggctt ccgcaaatta gacaaaacag cttttttgttt gattgatttt tctcttctct     660
ttttccatct aaattctctt tgggctctta atttctttttt gagtgttcgt tcgagatttg     720
tcggagattt tttcggtaaa tgttgaaatt ttgtgggatt ttttttttatt tctttattaa     780
actttttttt attgaattta taaaaaggga aggtcgtcat taatcgaaga aatggaatct     840
tccaaaattt gatattttgc tgttttcttg ggatttgaat tgctctttat catcaagaat     900
ctgttaaaat ttctaatcta aaatctaagt tgagaaaag agagatctct aatttaaccg      960
gaattaatat tctccgaccg aagttattat gttgcaggct                          1000

<210> SEQ ID NO 72
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP0384

<400> SEQUENCE: 72
tttaaaaaat tggataaaac accgataaaa attcacattt gcaaatttta ttcagtcgga      60
atatatattt gaaacaagtt ttgaaatcca ttggacgatt aaaattcatt gttgagagga     120
taaatatgga tttgttcatc tgaaccatgt cgttgattag tgattgacta ccatgaaaaa     180
tatgttatga aaagtataac aacttttgat aaatcacatt tattaacaat aaatcaagac     240
aaaatatgtc aacaataata gtagtagaag atattaattc aaattcatcc gtaacaacaa     300
aaaatcatac cacaattaag tgtacagaaa aaccttttgg atatatttat tgtcgctttt     360
caatgatttt cgtgaaaagg atatatttgt gtaaaataag aaggatcttg acgggtgtaa     420
aaacatgcac aattcttaat ttagaccaat cagaagacaa cacgaacact tctttattat     480
aagctattaa acaaaatctt gcctattttg cttagaataa tatgaagagt gactcatcag     540
ggagtggaaa atatctcagg atttgctttt agctctaaca tgtcaaacta tctagatgcc     600
aacaacacaa agtgcaaatt cttttaatat gaaaacaaca ataatatttc taatagaaaa     660
ttaaaagggg aaataaaata ttttttttaaa atatacaaaa gaagaaggaa tccatcatca     720
aagtttatata aaattgtaat ataatacaaa cttgtttgct tccttgtctc tccctctgtc     780
```

-continued

| | | |
|---|---|---|
| tctctcatct ctcctatctt ctccatatat acttcatctt cacacccaaa actccacaca | 840 |
| aaatatctct ccctctatct gcaaattttc caaagttgca tcctttcaat ttccactcct | 900 |
| ctctaatata attcacattt tcccactatt gctgattcat ttttttttgt gaattatttc | 960 |
| aaacccacat aaaaaaatct ttgtttaaat ttaaaacca | 999 |

<210> SEQ ID NO 73
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter YP0385

<400> SEQUENCE: 73

| | | |
|---|---|---|
| actcaacaat aggacaagcc aaaaaaattc caattattgt gttactctat tcttctaaat | 60 |
| ttgaacacta atagactatg acatatgagt atataatgtg aagtcttaag atattttcat | 120 |
| gtgggagatg aataggccaa gttggagtct gcaaacaaga agctcttgag ccacgacata | 180 |
| agccaagttg atgaccgtaa ttaatgaaac taaatgtgtg tggttatata ttagggaccc | 240 |
| atggccatat acacaatttt tgtttctgtc gatagcatgc gtttatatat atttctaaaa | 300 |
| aaactaacat atttactgga tttgagttcg aatattgaca ctaatataaa ctacgtacca | 360 |
| aactacatat gtttatctat atttgattga tcgaagaatt ctgaactgtt ttagaaaatt | 420 |
| tcaatacact taacttcatc ttacaacggt aaaagaaatc accactagac aaacaatgcc | 480 |
| tcataatgtc tcgaaccctc aaactcaaga gtatacattt tactagatta gagaatttga | 540 |
| tatcctcaag ttgccaaaga attggaagct tttgttacca aacttagaaa cagaagaagc | 600 |
| cacaaaaaaa gacaaaggga gttaaagatt gaagtgatgc atttgtctaa gtgtgaaagg | 660 |
| tctcaagtct caactttgaa ccataataac attactcaca ctcccttttt ttttcttttt | 720 |
| ttttcccaaa gtacccttttt taattccctc tataacccac tcactccatt ccctctttct | 780 |
| gtcactgatt caacacgtgg ccacactgat gggatccacc tttcctctta cccacctccc | 840 |
| ggtttatata aacccttcac aacacttcat cgctctcaaa ccaactctct cttctctctt | 900 |
| ctctcctctc ttctacaaga agaaaaaaaa cagagccttt acacatctca aaatcgaact | 960 |
| tactttaacc accaaatact gattgaacac acttgaaa | 998 |

<210> SEQ ID NO 74
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0396

<400> SEQUENCE: 74

| | | |
|---|---|---|
| catagtaaaa gtgaatttaa tcatactaag taaaataaga taaaacatgt tatttgaatt | 60 |
| tgaatatcgt gggatgcgta tttcggtatt tgattaaagg tctggaaacc ggagctccta | 120 |
| taacccgaat aaaaatgcat aacatgttct tccccaacga ggcgagcggg tcagggcact | 180 |
| agggtcattg caggcagctc ataaagtcat gatcatctag gagatcaaat tgtatgtcgg | 240 |
| ccttctcaaa attacctcta agaatctcaa acccaatcat agaacctcta aaaagacaaa | 300 |
| gtcgtcgctt tagaatgggt tcggtttttg gaaccatatt tcacgtcaat ttaatgttta | 360 |
| gtataatttc tgaacaacag aattttggat ttatttgcac gtatacaaat atctaattaa | 420 |

| | |
|---|---|
| taaggacgac tcgtgactat ccttacatta agtttcactg tcgaaataac atagtacaat | 480 |
| acttgtcgtt aatttccacg tctcaagtct ataccgtcat ttacggagaa agaacatctc | 540 |
| tgttttcat ccaaactact attctcactt tgtctatata tttaaaatta agtaaaaaag | 600 |
| actcaatagt ccaataaaat gatgaccaaa tgagaagatg gttttgtgcc agattttagg | 660 |
| aaaagtgagt caaggtttca catctcaaat ttgactgcat aatcttcgcc attaacaacg | 720 |
| gcattatata tgtcaagcca attttccatg ttgcgtactt ttctattgag gtgaaaatat | 780 |
| gggtttgttg attaatcaaa gagtttgcct aactaatata actacgactt tttcagtgac | 840 |
| cattccatgt aaactctgct tagtgtttca tttgtcaaca atattgtcgt tactcattaa | 900 |
| atcaaggaaa aatatacaat tgtataattt tcttatattt taaaattaat tttgatgtat | 960 |
| taccccttta taaataggct atcgctacaa caccaataac | 1000 |

<210> SEQ ID NO 75
<211> LENGTH: 1514
<212> TYPE: DNA
<213> ORGANISM: Arabidopsis thaliana
<220> FEATURE:
<221> NAME/KEY: misc_feature
<222> LOCATION: (1)..(1514)
<223> OTHER INFORMATION: Ceres Promoter p13879

<400> SEQUENCE: 75

| | |
|---|---|
| tttcgatcct cttctttttt aggtttcttg atttgatgat cgccgccagt agagccgtcg | 60 |
| tcggaagttt cagagattaa aaccatcacc gtgtgagttg gtagcgaatt aacggaaagt | 120 |
| ctaagtcaag attttttaaa aagaaattta tgtgtgaaaa gaagccgttg tgtatattta | 180 |
| tataatttag aaaatgtttc atcatttaa ttaaaaaatt aataaatttgt agaagaaaga | 240 |
| agcatttttt atacataaat catttacctt ctttactgtg ttttttcttca cttacttcat | 300 |
| ttttactttt ttacaaaaaa gtgaaaagta aattacgtaa ttggtaacat aaattcactt | 360 |
| taaatttgca tatgttttgt tttcttcgga aactatatcg aaaagcaaac ggaaagaact | 420 |
| tcacaaaaaa ccctagctaa ctaaagacgc atgtgttctt cttattcttc atatatcctc | 480 |
| tgtttcttgt gttctgtttt gagtcttaca ttttcaatat ctgactctga ttactatatc | 540 |
| taaaagggaa catgaagaac ttgagaccat gttaaactgt acaatgcctt caaacatggc | 600 |
| taactaaaga tacattagat ggctttacag tgtgtaatgc ttattatctt taggtttttt | 660 |
| aaatcccttg tattaagtta tttaccaaat tatgttcttg tactgcttat tggcttggtt | 720 |
| gttgtgtgct ttgtaaacaa caccttggc tttattcat cctttgtaaa cctactggtc | 780 |
| tttgttcagc tcctcttgga agtgagtttt tatgcctgga acgggtttta atggagtgtt | 840 |
| tatcgacaaa aaaaaatgt agcttttgaa atcacagaga gtagttttat attcaaatta | 900 |
| catgcatgca actaagtagc aacaaagttg atatggccga gttggtctaa ggcgccagat | 960 |
| taaggttctg gtccgaaagg gcgtgggttc aaatcccact gtcaacattc tcttttttctc | 1020 |
| aaattaatat ttttctgcct caatggttca ggcccaatta tactagacta ctatcgcgac | 1080 |
| taaaataggg actagccgaa ttgatccggc ccagtatcag ttgtgtatca ccacgttatt | 1140 |
| tcaaatttca aactaaggga taaagatgtc atttgacata tgagatattt ttttgctcca | 1200 |
| ctgagatatt tttctttgtc ccaagataaa atatctttc tcgcatcgtc gtctttccat | 1260 |
| ttgcgcatta aaccaaaaag tgtcacgtga tatgtcccca accactacga atttaacta | 1320 |
| cagatttaac catggttaaa ccagaattca cgtaaaccga ctctaaacct agaaaatatc | 1380 |
| taaaccttgg ttaatatctc agccccctta taaataacga gacttcgtct acatcgttct | 1440 |

```
acacatctca ctgctcacta ctctcactgt aatcccttag atcttctttt caaatttcac    1500
cattgcactg gatg                                                      1514

<210> SEQ ID NO 76
<211> LENGTH: 1954
<212> TYPE: DNA
<213> ORGANISM: Arabidopsis thaliana
<220> FEATURE:
<221> NAME/KEY: misc_feature
<222> LOCATION: (1)..(1954)
<223> OTHER INFORMATION: Ceres Promoter p326

<400> SEQUENCE: 76
gtgggtaaaa gtatccttct ttgtgcattt ggtatttta agcatgtaat aagaaaaacc      60
aaaatagacg gctggtattt aataaaagga gactaatgta tgtatagtat atgatttgtg     120
tggaatataa taaagttgta aaatatagat gtgaagcgag tatctatctt ttgactttca    180
aaggtgatcg atcgtgttct ttgtgatagt tttggtcgtc ggtctacaag tcaacaacca    240
ccttgaagtt ttcgcgtctc ggtttcctct tcgcatctgg tatccaatag catacatata    300
ccagtgcgga aaatggcgaa gactagtggg cttgaaccat aaggtttggc cccaatacgg    360
attccaaaca acaagcctag cgcagtcttt tgggatgcat aagactaaac tgtcgcagtg    420
atagacgtaa gatatatcga cttgattgga atcgtctaag ctaataagtt taccttgacc    480
gtttatagtt gcgtcaacgt ccttatggag attgatgccc atcaaataaa cctgaaaatc    540
catcaccatg accaccataa actcccttgc tgccgctgct ttggcttgag caaggtgttt    600
ccttgtaaag ctccgatctt tggataaagt gttccacttt ttgcaagtag ctctgacccc    660
tctcagagat gtcaccggaa tcttagacag aacctcctct gccaaatcac ttggaagatc    720
ggacaatgtc atcattttg caggtaattt ctccttcgtt gctgctttgg cttgagcacg     780
gtgcttcttt gtaaagctcc gatctttgga taagagcgga tcggaatcct ctaggaggtg    840
ccagtccctt gacctattaa tttatagaag gttttagtgt attttgttcc aatttcttct    900
ctaacttaac aaataacaac tgcctcatag tcatgggctt caaattttat cgcttggtgt    960
atttcgttat ttgcaaggcc ttggcccatt ttgagcccaa taactaaatc tagccttttc   1020
agaccggaca tgaacttcgc atattggcgt aactgtgcag ttttaccttt ttcggatcag   1080
acaagatcag atttagacca cccaacaata gtcagtcata tttgacaacc taagctagcc   1140
gacactacta aaaagcaaac aaaagaagaa ttctatgttg tcattttacc ggtggcaagt   1200
ggacccttct ataaaagagt aaagagacag cctgtgtgtg tataatctct aattatgttc   1260
accgacacaa tcacacaaac ccttctctaa tcacacaact tcttcatgat ttacgacatt   1320
aattatcatt aactctttaa attcacttta catgctcaaa aatatctaat ttgcagcatt   1380
aatttgagta ccgataacta ttattataat cgtcgtgatt cgcaatcttc ttcattagat   1440
gctgtcaagt tgtactcgca cgcggtggtc cagtgaagca aatccaacgg tttaaaacct   1500 tcttacatttt ctagatctaa tctgaaccgt cagatatcta gatctcattg tctgaacaca   1560
gttagatgaa actgggaatg aatctggacg aaattacgat cttacaccaa cccctcgac    1620 gagctcgtat atataaagct tatacgctcc tccttcacct tcgtactact actaccacca   1680
catttcttta gctcaacctt cattactaat ctcctttaa ggtatgttca cttttcttcg    1740
attcatactt tctcaagatt cctgcatttc tgtagaattt gaaccaagtg tcgattttg    1800 tttgagagaa gtgttgattt atagatctgg ttattgaatc tagattccaa tttttaattg   1860
```

```
attcgagttt gttatgtgtg tttatactac ttctcattga tcttgtttga tttctctgct   1920
ctgtattagg tttctttcgt gaatcagatc ggaa                              1954

<210> SEQ ID NO 77
<211> LENGTH: 2016
<212> TYPE: DNA
<213> ORGANISM: Arabidopsis thaliana
<220> FEATURE:
<221> NAME/KEY: misc_feature
<222> LOCATION: (1)..(2016)
<223> OTHER INFORMATION: Ceres Promoter p32449

<400> SEQUENCE: 77
gatcggcctt cttcaggtct tctctgtagc tctgttactt ctatcacagt tatcgggtat     60
ttgagaaaaa agagttagct aaaatgaatt tctccatata atcatggttt actacaggtt    120
tacttgattc gcgttagctt tatctgcatc caaagttttt tccatgatgt tatgtcatat    180
gtgataccgt tactatgttt ataactttat acagtctggt tcactggagt ttctgtgatt    240
atgttgagta catactcatt catcctttgg taactctcaa gtttaggttg tttgaattgc    300
ctctgttgtg atacttattg tctattgcat caatcttcta atgcaccacc ctagactatt    360
tgaacaaaga gctgtttcat tcttaaacct ctgtgtctcc ttgctaaatg gtcatgcttt    420
aatgtcttca cctgtctttc tcttctatag atatgtagtc ttgctagata gttagttcta    480
cagctctctt ttgtagtctt gttagagagt tagttgagat attacctctt aaaagtatcc    540
ttgaacgctt tccggttatg accaatttgt tgtagctcct tgtaagtaga acttactggg    600
accagcgaga cagtttatgt gaatgttcat gcttaagtgt cgaacgtatc tatctctact    660
atagctctgt agtcttgtta dacagttagt tttatatctc catttttttg tagtcttgct    720
agttgagata ttacctcttc tcttcaaagt atccttgaac gctcaccggt tatgaaatct    780
ctacactata gctctgtagt cttgctagat agttagttct ttagctctct ttttgtagcc    840
tagttcttta gctctccttt tgtagccttg ctacagagta agatgggata ttacctcctt    900
gaacgctctc cggttatgac caatttgttg tagctccttg taagtagaac ttaggataga    960
gtgagtcaac tttaagaaag aacctagtat gtggcataac cagattgcag gctctgtctc   1020
ggctacagta acgtaactct atagctcttt gttttgttca gaaagaacca gtgattggat   1080
gattcgtcct tagaaactgg acctaacaac agtcattggc tttgaaatca agccacaaca   1140
atgcctatat gaaccgtcca tttcatttat ccgtttcaaa ccagcccatt acatttcgtc   1200
ccattgataa ccaaaagcgg ttcaatcaga ttatgtttta attttaccaa attctttatg   1260
aagtttaaat tatactcaca ttaaaaggat tattggataa tgtaaaaatt ctgaacaatt   1320
actgattttg gaaaattaac aaatattctt tgaaatagaa gaaaaagcct tttccttttt    1380
gacaacaaca tataaaatca tactcccatt aaaaagattt taatgtaaaa ttctgaatat   1440
aagatatttt ttacaacaac aaccaaaaat atttattttt ttccttttttt acagcaacaa   1500 gaaggaaaaa ctttttttttt tgtcaagaaa aggggagatt atgtaaacag ataaaacagg   1560
gaaaataact aaccgaactc tcttaattaa catcttcaaa taaggaaaat tatgatccgc   1620
atatttagga agatcaatgc attaaaacaa cttgcacgtg gaaagagaga ctatacgctc   1680
cacacaagtt gcactaatgg tacctctcac aaaccaatca aaatactgaa taatgccaac   1740
gtgtacaaat tagggtttta cctcacaacc atcgaacatt tcgaaacat ttaaacagc    1800 ctggcgccat agatctaaac tctcatcgac caatttttga ccgtccgatg gaaactctag   1860
cctcaaccca aaactctata taagaaatc ttttccttcg ttattgctta ccaaatacaa   1920
```

-continued

```
accctagccg ccttattcgt cttcttcgtt ctctagtttt ttcctcagtc tctgttctta    1980
gatcccttgt agtttccaaa tcttccgata aggcct                              2016

<210> SEQ ID NO 78
<211> LENGTH: 1024
<212> TYPE: DNA
<213> ORGANISM: Arabidopsis thaliana
<220> FEATURE:
<221> NAME/KEY: misc_feature
<222> LOCATION: (1)..(1024)
<223> OTHER INFORMATION: Ceres Promoter PR0924

<400> SEQUENCE: 78
atctataacg agttaacatg ttgccagttt gaatcaagaa gcttggatga tgaatgaatg      60
gatcggtttg tggtacaatt cttaaaattg tagtagagga gacagagaaa aaacatgata    120
agactttggt atttacaact tgacggagac aagacagtaa gccaaatctg tcacaaaaac    180
actcaaactc ttttctcagt gttttgagtt taaagagaga cttattcact tcccctttcg    240
taacacttat ttgtctccca accaaacagt ttctgtcctt tcccttgtcc tcccacgtgc    300
atctttatat ctcatgactt ttcgtttcta gatcttgaat aatgtcttag tggattaggt    360
ttgttgtcgg taaattaggt gaccgttttt ttcttatatt tggaagatcg cgggatgaag    420
cagatactga gtttcagggc atacacacct aatttgaaaa tcattgttag tccaatttca    480
ctttaatctt gtttacaaaa aaattgatct gaaaatgttg atgggataag taaaaatgta    540
agttttgcta gtagtcatga tataataata gcaaaaccag atcaattttg agcaaaagga    600
agaaacaaaa aacagatcga tcccacgagc aagactaagt gtaaagtggt tcccacaaga    660
gccatatgga tatggtcctt caacttttaa agcccattac ttcagtggtc gacccgacat    720
tacgccacga gtagtcacgc acgcacgact ccgttcacgt gacattcacg ttgatatttc    780
cccctctact ctcttctgct tggttgatct aaaaaacatg aagagaccaa cctaatttca    840
tattaatata tgatatagac ttcatactca acagtcactt tcgtaatcca aatccatatc    900
ttacgaaatt agttcttaat aaaggttgtg gattaagtta taatattgtg ttaagagtta    960
agacacagca tataaccttg taccaacagt gctttattct taaatggaaa caaaacatat   1020
gtca                                                                1024

<210> SEQ ID NO 79
<211> LENGTH: 857
<212> TYPE: DNA
<213> ORGANISM: Arabidopsis thaliana
<220> FEATURE:
<221> NAME/KEY: misc_feature
<222> LOCATION: (1)..(857)
<223> OTHER INFORMATION: Ceres Promoter PD1367
<220> FEATURE:
<221> NAME/KEY: misc_feature
<222> LOCATION: (116)..(116)
<223> OTHER INFORMATION: n is a, c, t, g, unknown, or other
<220> FEATURE:
<221> NAME/KEY: misc_feature
<222> LOCATION: (136)..(136)
<223> OTHER INFORMATION: n is a, c, t, g, unknown, or other
<220> FEATURE:
<221> NAME/KEY: misc_feature
<222> LOCATION: (154)..(154)
<223> OTHER INFORMATION: n is a, c, t, g, unknown, or other
<220> FEATURE:
<221> NAME/KEY: misc_feature
<222> LOCATION: (159)..(159)
<223> OTHER INFORMATION: n is a, c, t, g, unknown, or other
```

<220> FEATURE:
<221> NAME/KEY: misc_feature
<222> LOCATION: (168)..(168)
<223> OTHER INFORMATION: n is a, c, t, g, unknown, or other
<220> FEATURE:
<221> NAME/KEY: misc_feature
<222> LOCATION: (172)..(172)
<223> OTHER INFORMATION: n is a, c, t, g, unknown, or other
<220> FEATURE:
<221> NAME/KEY: misc_feature
<222> LOCATION: (175)..(175)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<222> LOCATION: (680)..(680)
<223> OTHER INFORMATION: n is a, c, t, g, unknown, or other
<220> FEATURE:
<221> NAME/KEY: misc_feature
<222> LOCATION: (686)..(686)
<223> OTHER INFORMATION: n is a, c, t, g, unknown, or other
<220> FEATURE:
<221> NAME/KEY: misc_feature
<222> LOCATION: (724)..(724)
<223> OTHER INFORMATION: n is a, c, t, g, unknown, or other
<220> FEATURE:
<221> NAME/KEY: misc_feature
<222> LOCATION: (737)..(737)
<223> OTHER INFORMATION: n is a, c, t, g, unknown, or other

<400> SEQUENCE: 79

| | | | | | | |
|---|---|---|---|---|---|---|
| ttggaattaa | ttctgcggcc | atggggctgc | aggaattcga | tggcccgatc | ggccacagtt | 60 |
| ttcttttctc | atcttacaac | aagtttccag | gaggatagag | acataaacga | agctcnggat | 120 |
| tgtatcgttc | tttttnagct | tttattcaca | tccngaaang | tcctgtangt | tntangattc | 180 |
| tgttatcttg | cggttttgag | ttaatcagaa | acagagtaat | caatgtaatg | ttgcaggcta | 240 |
| gatctttcat | ctttggaaat | ttgttttttt | ctcatgcaat | ttctttagct | tgaccatgag | 300 |
| tgactaaaag | atcaatcagt | agcaatgatt | tgatttggct | aagagacatt | tgtccacttg | 360 |
| gcatcttgat | ttggatggtt | acaacttgca | agacccaatt | ggatacttgc | tatgacaact | 420 |
| ccaactcaag | agtgtcgtgt | aactaagaac | cttgactaat | ttgtaatttc | aatcccaagt | 480 |
| catgttacta | tatgtttttt | tgtttgtatt | attttctctc | ctacaattaa | gctctttgac | 540 |
| gtacgtaatc | tccggaacca | actcctatat | ccaccattta | ctccacgttg | tctccaatta | 600 |
| ttggacgttg | aaacttgaca | caacgtaaac | gtatctacgt | ggttgattgt | atgtacatat | 660 |
| gtacaaacgt | acacctttnn | ctcctncttt | cacttcatca | cttggcttgt | gaattcatta | 720 |
| attncctgcg | aaggccntgc | agggccatca | ccactgcagt | ggaacaatga | agactaatct | 780 |
| ttttctcttt | ctcatctttt | cacttctcct | atcattatcc | tcggccgaat | tcagtaaagg | 840 |
| agaagaactt | ttcactg | | | | | 857 |

<210> SEQ ID NO 80
<211> LENGTH: 692
<212> TYPE: DNA
<213> ORGANISM: Arabidopsis thaliana
<220> FEATURE:
<221> NAME/KEY: misc_feature
<222> LOCATION: (1)..(692)
<223> OTHER INFORMATION: Ceres CLONE ID no. 18200
<220> FEATURE:
<221> NAME/KEY: misc_feature
<222> LOCATION: (1)..(692)
<223> OTHER INFORMATION: Also Known As Ceres ME LINE ME20023

```
<220> FEATURE:
<221> NAME/KEY: CDS
<222> LOCATION: (117)..(399)
<223> OTHER INFORMATION: Referenced by SEQ ID NO: 81

<400> SEQUENCE: 80
aacaccttct tctccactct cattctctct ttctgacaca ttaactactt atccttcttg      60
cattcttctc tctctctaca cccaaacaaa cacacttata atatatcaag aaagaagatg     120
tctagcagaa gatcatcacg ttcaagacag tcaggaagct caagaatctc tgacgatcag     180
atttccgatc ttgtttctaa gctccaaac ctcatccctg aacttcgccg ccgccgttct     240
gacaaggtgt cagcatctaa ggtactacaa gagacttgca actacatcag gaacttacac     300
agagaggttg atgacctcag tgaccgtttg tcggaactct tggcttcgac ggacgacaac     360
agcgccgaaa cagccatcat taggagcttg cttaattatt aaatccgcat tacttaatct     420
gagagctatt aatcatccgt ttccggccac caaatttatc ttattatggg tatcgtctgt     480
ttacttctac atcatatatt atgagatata gctagggttt cgggtcattg ttaggccaac     540
tcatatattt atatttaata tatggttatg tatgtatgta tgcatgttaa ttgtatctga     600
gggtccagac ctggcgtata gtagcctgtg tatcatgaga tcctctaata tttatgatta     660
atgacacggt ccgtttcctt ttttactata cc                                   692

<210> SEQ ID NO 81
<211> LENGTH: 94
<212> TYPE: PRT
<213> ORGANISM: Arabidopsis thaliana
<220> FEATURE:
<221> NAME/KEY: misc_feature
<222> LOCATION: (1)..(94)
<223> OTHER INFORMATION: Ceres CLONE ID no. 18200
<220> FEATURE:
<221> NAME/KEY: misc_feature
<222> LOCATION: (1)..(94)
<223> OTHER INFORMATION: Also Known As Ceres ME LINE ME20023
<220> FEATURE:
<221> NAME/KEY: misc_feature
<222> LOCATION: (20)..(61)
<223> OTHER INFORMATION: Pfam Name: HLH; Pfam Description:
      Helix-loop-helix DNA-binding domain

<400> SEQUENCE: 81

Met Ser Ser Arg Arg Ser Ser Arg Ser Arg Gln Ser Gly Ser Ser Arg
1               5                   10                  15

Ile Ser Asp Asp Gln Ile Ser Asp Leu Val Ser Lys Leu Gln His Leu
            20                  25                  30

Ile Pro Glu Leu Arg Arg Arg Arg Ser Asp Lys Val Ser Ala Ser Lys
        35                  40                  45

Val Leu Gln Glu Thr Cys Asn Tyr Ile Arg Asn Leu His Arg Glu Val
    50                  55                  60

Asp Asp Leu Ser Asp Arg Leu Ser Glu Leu Leu Ala Ser Thr Asp Asp
65                  70                  75                  80

Asn Ser Ala Glu Thr Ala Ile Ile Arg Ser Leu Leu Asn Tyr
                85                  90

<210> SEQ ID NO 82
<211> LENGTH: 1155
<212> TYPE: DNA
<213> ORGANISM: Zea mays
<220> FEATURE:
<221> NAME/KEY: misc_feature
<222> LOCATION: (1)..(1155)
<223> OTHER INFORMATION: Ceres CLONE ID no. 336524
```

```
<220> FEATURE:
<221> NAME/KEY: misc_feature
<222> LOCATION: (1)..(1155)
<223> OTHER INFORMATION: Also Known As Ceres ME LINE ME10686
<220> FEATURE:
<221> NAME/KEY: CDS
<222> LOCATION: (156)..(417)
<223> OTHER INFORMATION: Referenced by SEQ ID NO: 83

<400> SEQUENCE: 82
gagtcttgac acgagctccc acacgtacac tgcataaata ggcgagcagc gggagagaga      60
cgaccgacga ggacgaagag gaattaagcc agagcgatcg aggtggtgta gtgtagcttc     120
cgagcgaagc tcctaccgtt gccgccggcc ggagatatgt cgtcgggcgg ccgacgtggc     180
aggatcagcg acgacgagat caacgagctg atctccaagc tccaggctct cctcccggaa     240
tcctcacgcc gccggaacgc gagccggtcg tcggcgtcga agcttctgaa ggagacgtgc     300
gcctacgtca agagcctgca ccgggaggtg gacgacctct cggagcggct gtcggggctc     360
atggagacca tggacaacga cagcccccag gccgagatca tccggagcct cctccggtga     420
ctccagagtc caggttccag ccatgccgct tgccgcccg  gtcgtccggc gcgcgcggcc     480
gccctcttct gctgcctgcc atctagctag ctgccgcagc cagcgcaggt gcacttgaga     540
ttggagaagg agaagacgac gacgtacggc cgagcttgct tgttcgctcg tttatttgtt     600
acggcgacga ccttaattgt attcctttgt tcttaatttg ttctcctcct tctcctcctc     660
ctcctccttc gggtgcgtgt tgtttccgt gttgaattag ttcaagagca agagcccttg     720
ctcagaagaa ggcgaccaaa agtgctctac tcgatcttct cgtgtaccac gccagggggg     780
gttagtagag tagagataat gtatggactt ctattaacca actaaaggta ccacgtactg     840
gtaggttgta gttgcagtag actactggta gtagggtgta gttttgcagt agactactgt     900
agcagttcta cattgcggat gcgtccaaag agttgttgtt gttctgtaga ttgcatgctg     960
ctcttgtctc tgtcgtcgtc cttagcttac ggcgttacgc caatgggcgg cggacaagga    1020
gctgaacgac gaccactctg tctggtggag acaaatatat acactatcac gtgatttcc     1080
tctctttagc tccatcctga tgtaacttgg taatttactc catccctccg tcatttttt     1140
tgcaatagtt ctttt                                                     1155

<210> SEQ ID NO 83
<211> LENGTH: 87
<212> TYPE: PRT
<213> ORGANISM: Zea mays
<220> FEATURE:
<221> NAME/KEY: misc_feature
<222> LOCATION: (1)..(87)
<223> OTHER INFORMATION: Ceres CLONE ID no. 336524
<220> FEATURE:
<221> NAME/KEY: misc_feature
<222> LOCATION: (1)..(87)
<223> OTHER INFORMATION: Also Known As Ceres ME LINE ME10686

<400> SEQUENCE: 83

Met Ser Ser Gly Gly Arg Arg Gly Arg Ile Ser Asp Asp Glu Ile Asn
1               5                   10                  15

Glu Leu Ile Ser Lys Leu Gln Ala Leu Leu Pro Glu Ser Ser Arg Arg
            20                  25                  30

Arg Asn Ala Ser Arg Ser Ser Ala Ser Lys Leu Leu Lys Glu Thr Cys
        35                  40                  45

Ala Tyr Val Lys Ser Leu His Arg Glu Val Asp Asp Leu Ser Glu Arg
    50                  55                  60
```

```
Leu Ser Gly Leu Met Glu Thr Met Asp Asn Asp Ser Pro Gln Ala Glu
65                  70                  75                  80

Ile Ile Arg Ser Leu Leu Arg
                85
```

<210> SEQ ID NO 84
<211> LENGTH: 712
<212> TYPE: DNA
<213> ORGANISM: Arabidopsis thaliana
<220> FEATURE:
<221> NAME/KEY: misc_feature
<222> LOCATION: (1)..(712)
<223> OTHER INFORMATION: Ceres CLONE ID no. 4734
<220> FEATURE:
<221> NAME/KEY: misc_feature
<222> LOCATION: (1)..(712)
<223> OTHER INFORMATION: Also Known As Ceres ME LINE ME01905
<220> FEATURE:
<221> NAME/KEY: CDS
<222> LOCATION: (282)..(558)
<223> OTHER INFORMATION: Referenced by SEQ ID NO: 85

<400> SEQUENCE: 84

```
aatatttgaa gtgtattcaa aaccccaaaa cactttctc attctcttct ctatttcttt      60
cttgctctct agtttttctt tcttcttggt cgtttccttt cagcataaaa accttataaa     120
atcataaaag cttacaccta cttgccacat agacatagcc gatctcatta tatctctatt     180
tctatttctc aatagaactt gtttgagcta gtgtgagaga agtaaagaaa gagagaagaa     240
tccacaactt agttagggtc ttttcttgcc acattgttga acatgtcgaa cagaagatca     300
aggcaatctt caagtgctcc aaggatctcc gataatcaaa tgattgacct cgtatctaag     360
ctccgtcaaa ttttgccgga gattggtcaa cgacgtcgtt ctgataaggc atcagcctcg     420
aaagtattgc aagagacatg caattacata cgaaatttga acagaaagt tgacaatctg     480 agcgagcgtt tgtctcagct tctcgaatct gtcgatgaag atagccctga agccgccgtt     540
attagaagcc tactcatgta atctttttg ttcttttgtt tgtttttgac aagcctatcc     600
atgtaatctt aaatgatcgc tctataataa ttatattttt aacataatcg tcttattatg     660
taaaattcaa agagatgggc ttgatctta atgacatacg aatttcatag gg              712
```

<210> SEQ ID NO 85
<211> LENGTH: 92
<212> TYPE: PRT
<213> ORGANISM: Arabidopsis thaliana
<220> FEATURE:
<221> NAME/KEY: misc_feature
<222> LOCATION: (1)..(92)
<223> OTHER INFORMATION: Ceres CLONE ID no. 4734
<220> FEATURE:
<221> NAME/KEY: misc_feature
<222> LOCATION: (1)..(92)
<223> OTHER INFORMATION: Also Known As Ceres ME LINE ME01905
<220> FEATURE:
<221> NAME/KEY: misc_feature
<222> LOCATION:
<223> OTHER INFORMATION: Phenotype: INFLORESCENCE
    Useful for making ornamental plants
    with modified flowers
<220> FEATURE:
<221> NAME/KEY: misc_feature
<222> LOCATION:
<223> OTHER INFORMATION: Phenotype: Glossy
    Useful for making plants
    with enhanced abiotic stress tolerance

<400> SEQUENCE: 85

Met Ser Asn Arg Arg Ser Arg Gln Ser Ser Ala Pro Arg Ile Ser
1               5                   10                  15

Asp Asn Gln Met Ile Asp Leu Val Ser Lys Leu Arg Gln Ile Leu Pro
            20                  25                  30

Glu Ile Gly Gln Arg Arg Ser Asp Lys Ala Ser Ala Ser Lys Val
        35                  40                  45

Leu Gln Glu Thr Cys Asn Tyr Ile Arg Asn Leu Asn Arg Glu Val Asp
    50                  55                  60

Asn Leu Ser Glu Arg Leu Ser Gln Leu Leu Glu Ser Val Asp Glu Asp
65                  70                  75                  80

Ser Pro Glu Ala Ala Val Ile Arg Ser Leu Leu Met
                85                  90

<210> SEQ ID NO 86
<211> LENGTH: 557
<212> TYPE: DNA
<213> ORGANISM: Arabidopsis thaliana
<220> FEATURE:
<221> NAME/KEY: misc_feature
<222> LOCATION: (1)..(557)
<223> OTHER INFORMATION: Ceres CLONE ID no. 519
<220> FEATURE:
<221> NAME/KEY: misc_feature
<222> LOCATION: (1)..(557)
<223> OTHER INFORMATION: Also Known As Ceres ME LINE ME01770
<220> FEATURE:
<221> NAME/KEY: CDS
<222> LOCATION: (153)..(432)
<223> OTHER INFORMATION: Referenced by SEQ ID NO: 87

<400> SEQUENCE: 86

```
atactatcaa cttttctcta tctatctctc tctcttcttt ttccggcata acttctgtgt    60
taccctaaac tccataacct gtttcatcga taaagtgcct ttgcttctat ctctgtcact   120
cttactactt gttgaacaat attctacaaa aaaatgtcgg gaagaagatc acgttcgagg   180
caatcatcag gaacttcaag gatctcagaa gatcaaatca atgatctgat tatcaagttg   240
caacagcttc ttcctgagct cagggacagt cgtcgttccg acaaggtttc agcagcgagg   300
gtgttacaag atacgtgcaa ctacatacgg aatctgcata gagaggttga tgatctaagt   360
gagaggctat ctgagttact agcaaaactca gacactgcac aagctgcttt aatcagaagc   420
ttacttaccc aataattcct atctatcttt ttcttcttct tctttttttt gtttactata   480
ataataataa tagtttgcgg gttttttttt ctatagatgt tgatgacctt ataaacgttt   540
aatgatacga gttcgtc                                                  557
```

<210> SEQ ID NO 87
<211> LENGTH: 93
<212> TYPE: PRT
<213> ORGANISM: Arabidopsis thaliana
<220> FEATURE:
<221> NAME/KEY: misc_feature
<222> LOCATION: (1)..(93)
<223> OTHER INFORMATION: Ceres CLONE ID no. 519
<220> FEATURE:
<221> NAME/KEY: misc_feature
<222> LOCATION: (1)..(93)
<223> OTHER INFORMATION: Also Known As Ceres ME LINE ME01770
<220> FEATURE:
<221> NAME/KEY: misc_feature
<222> LOCATION: (20)..(62)
<223> OTHER INFORMATION: Pfam Name: HLH; Pfam Description:
      Helix-loop-helix DNA-binding domain

```
<220> FEATURE:
<221> NAME/KEY: misc_feature
<222> LOCATION:
<223> OTHER INFORMATION: Phenotype: WHOLE PLANT
      Useful for making bigger plants
<220> FEATURE:
<221> NAME/KEY: misc_feature
<222> LOCATION:
<223> OTHER INFORMATION: Phenotype: Long
      Useful for making taller plants

<400> SEQUENCE: 87

Met Ser Gly Arg Arg Ser Arg Ser Arg Gln Ser Ser Gly Thr Ser Arg
 1               5                  10                  15

Ile Ser Glu Asp Gln Ile Asn Asp Leu Ile Ile Lys Leu Gln Gln Leu
            20                  25                  30

Leu Pro Glu Leu Arg Asp Ser Arg Arg Ser Asp Lys Val Ser Ala Ala
        35                  40                  45

Arg Val Leu Gln Asp Thr Cys Asn Tyr Ile Arg Asn Leu His Arg Glu
    50                  55                  60

Val Asp Asp Leu Ser Glu Arg Leu Ser Glu Leu Leu Ala Asn Ser Asp
65                  70                  75                  80

Thr Ala Gln Ala Ala Leu Ile Arg Ser Leu Leu Thr Gln
                85                  90

<210> SEQ ID NO 88
<211> LENGTH: 771
<212> TYPE: DNA
<213> ORGANISM: Glycine max
<220> FEATURE:
<221> NAME/KEY: misc_feature
<222> LOCATION: (1)..(771)
<223> OTHER INFORMATION: Ceres CLONE ID no. 560681
<220> FEATURE:
<221> NAME/KEY: misc_feature
<222> LOCATION: (1)..(771)
<223> OTHER INFORMATION: Also Known As Ceres ME LINE ME08328
<220> FEATURE:
<221> NAME/KEY: CDS
<222> LOCATION: (275)..(548)
<223> OTHER INFORMATION: Referenced by SEQ ID NO: 89

<400> SEQUENCE: 88
atatatctta gccttttctc tccctcccct ctcccatatt atatagcttg tcttttattt      60
cttagactcc atccattctt ctccccaatt gaatcttctt tattttgttt cttcactgtc     120
tcgttatggc tatagttttg catagtaaat aaactgaact gaagctatct atatagcagc     180
aagtgttgat ttaattactt actttagaca ataattatat taattacacc aatttataag     240
ctctttatct atctatctag ctagggaaaa ttaaaatgtc tagcagaagg tccaggcagc     300
aatctgcatc cacaaggatc tccgatgacc aaatcatcga cctcgtttca agttgcgtc      360 aacttgttcc tgagattcgc gataggcgct ctgacaaggt atcagcatct aaggtcctac     420
aagagacctg caactacatc agaagcttac acagagaagt ggatgactta agcgaacgac     480
tgtctcagtt gttggccaca atcgatgctg atagccctga agctgccatc attaggagcc     540
taattaacta ataatatata ttaagcgcaa gtaatcatct aattttccta tattcaagga     600
gatatattat aagagtgtat taatttcttc ttytaaatta ggtggcatag agtgcagttt     660
gaggtgcgta cgtacgtcct tccaatatat tatagtacat ggcaggaatg gtgcacttgt     720
gtaagttaaa ggttttgca ataagaacta aggactctct gtattatggc g               771
```

<210> SEQ ID NO 89
<211> LENGTH: 91
<212> TYPE: PRT
<213> ORGANISM: Glycine max
<220> FEATURE:
<221> NAME/KEY: misc_feature
<222> LOCATION: (1)..(91)
<223> OTHER INFORMATION: Ceres CLONE ID no. 560681
<220> FEATURE:
<221> NAME/KEY: misc_feature
<222> LOCATION: (1)..(91)
<223> OTHER INFORMATION: Also Known As Ceres ME LINE ME08328
<220> FEATURE:
<221> NAME/KEY: misc_feature
<222> LOCATION: (25)..(59)
<223> OTHER INFORMATION: Pfam Name: HLH; Pfam Description:
    Helix-loop-helix DNA-binding domain

<400> SEQUENCE: 89

Met Ser Ser Arg Arg Ser Arg Gln Gln Ser Ala Ser Thr Arg Ile Ser
1               5                   10                  15

Asp Asp Gln Ile Ile Asp Leu Val Ser Lys Leu Arg Gln Leu Val Pro
            20                  25                  30

Glu Ile Arg Asp Arg Arg Ser Asp Lys Val Ser Ala Ser Lys Val Leu
        35                  40                  45

Gln Glu Thr Cys Asn Tyr Ile Arg Ser Leu His Arg Glu Val Asp Asp
    50                  55                  60

Leu Ser Glu Arg Leu Ser Gln Leu Leu Ala Thr Ile Asp Ala Asp Ser
65                  70                  75                  80

Pro Glu Ala Ala Ile Ile Arg Ser Leu Ile Asn
                85                  90

<210> SEQ ID NO 90
<211> LENGTH: 697
<212> TYPE: DNA
<213> ORGANISM: Glycine max
<220> FEATURE:
<221> NAME/KEY: misc_feature
<222> LOCATION: (1)..(697)
<223> OTHER INFORMATION: Ceres CLONE ID no. 560948
<220> FEATURE:
<221> NAME/KEY: misc_feature
<222> LOCATION: (1)..(697)
<223> OTHER INFORMATION: Also Known As Ceres ME LINE ME08317
<220> FEATURE:
<221> NAME/KEY: CDS
<222> LOCATION: (205)..(481)
<223> OTHER INFORMATION: Referenced by SEQ ID NO: 91

<400> SEQUENCE: 90
atgtgtttta tttcctactt cccaacccat aaccattaat tcttaattag tttcctcttg    60
ctttcttctc cttctatatt attactagta caacttatca tacacatata cctctggtta   120
tagcagcaaa ctaggctata gcttgcactt tgaagatatt tatacacaga ccaagtacaa   180
caccaagctc tagctagcta gggacatgtc tagccgaaga tccagacaac attcagggtc   240
tacaaggatc tccgatgacc aaatcatcga acttgtttcc aaattgcgcc aacttgttcc   300
tgagattcgc aataggcgat ctgataaggt ttcagcgtca aggtcctac aagagacctg    360 caactacatc agaggcttgc acagagaggt gagtgacttg agcgagcgac tgtctcagtt   420
gttgaccaca attgatgctg atagtgctga ggctggaatc attaggagcc tacttaatca   480
atgagagagt gttatgattt tttatttatt caaagagagt gttaattaaa ttataattat   540
gattattata agagtattgt acttcattct aggtgtgctg agagcctggg agagttcagt   600

```
ttttgaggct gtacctccca tatggcaggt agggcatttt cataactagt tgttttctc    660 tttttccaa taaaaattca agtgcttgta ccagctg                            697
```

<210> SEQ ID NO 91
<211> LENGTH: 92
<212> TYPE: PRT
<213> ORGANISM: Glycine max
<220> FEATURE:
<221> NAME/KEY: misc_feature
<222> LOCATION: (1)..(92)
<223> OTHER INFORMATION: Ceres CLONE ID no. 560948
<220> FEATURE:
<221> NAME/KEY: misc_feature
<222> LOCATION: (1)..(92)
<223> OTHER INFORMATION: Also Known As Ceres ME LINE ME08317
<220> FEATURE:
<221> NAME/KEY: misc_feature
<222> LOCATION: (25)..(59)
<223> OTHER INFORMATION: Pfam Name: HLH; Pfam Description:
      Helix-loop-helix DNA-binding domain

<400> SEQUENCE: 91

Met Ser Ser Arg Arg Ser Arg Gln His Ser Gly Ser Thr Arg Ile Ser
1               5                   10                  15

Asp Asp Gln Ile Ile Glu Leu Val Ser Lys Leu Arg Gln Leu Val Pro
            20                  25                  30

Glu Ile Arg Asn Arg Arg Ser Asp Lys Val Ser Ala Ser Lys Val Leu
        35                  40                  45

Gln Glu Thr Cys Asn Tyr Ile Arg Gly Leu His Arg Glu Val Ser Asp
    50                  55                  60

Leu Ser Glu Arg Leu Ser Gln Leu Leu Thr Thr Ile Asp Ala Asp Ser
65                  70                  75                  80

Ala Glu Ala Gly Ile Ile Arg Ser Leu Leu Asn Gln
                85                  90

<210> SEQ ID NO 92
<211> LENGTH: 728
<212> TYPE: DNA
<213> ORGANISM: Glycine max
<220> FEATURE:
<221> NAME/KEY: misc_feature
<222> LOCATION: (1)..(728)
<223> OTHER INFORMATION: Ceres CLONE ID no. 653656
<220> FEATURE:
<221> NAME/KEY: misc_feature
<222> LOCATION: (1)..(728)
<223> OTHER INFORMATION: Also Known As Ceres ME LINE ME21445
<220> FEATURE:
<221> NAME/KEY: CDS
<222> LOCATION: (244)..(520)
<223> OTHER INFORMATION: Referenced by SEQ ID NO: 93

<400> SEQUENCE: 92

```
acatgcaact tgtcttaatt tctttctcga tccccaacat cactagctag ctccttttgt    60
acacactcta caaccccacc tagctacatc acttaattag ttttcccata tctataacca   120
atttcaaatt ctcaccctta actagctagc tatatttcat aactgattat taccaactca   180
ctacatatta ttggctagga ttcaccatta gacttaaaag tagttgattt attatatata   240
taagatgtct agcaggaggt cacggtcaag gcaaacaagt agttcaagga atatcaccga   300
tgatcagatc aatgatcttg tctccaagtt gcaacagctt cttccagaga ttcgcgatag   360
gcgctctgac aaggtttcag cttccaaggt gttgcaagag acatgcaact atattagaag   420
cttacacagg gaagtggatg acctaagcga gcgtttatct gagctcttgg ctacaactga   480
```

-continued

```
cacagcacaa gctgcaataa ttagaaatct actaatgcaa tagatcggtg cagtagttaa    540
tttatcgcat aattcatagt tagcacttca gtacttgtga accgatccag tcagtagtcg    600
cgtatttctt attctctttt tgtttcactt tttttttctg gtttttgtcc actaatatgc    660
atgattactg cttttgcaaa gcccattttc ctaagatatt aaataaaagt ctgagtttgc    720
gctttgct                                                              728
```

```

<210> SEQ ID NO 93
<211> LENGTH: 92
<212> TYPE: PRT
<213> ORGANISM: Glycine max
<220> FEATURE:
<221> NAME/KEY: misc_feature
<222> LOCATION: (1)..(92)
<223> OTHER INFORMATION: Ceres CLONE ID no. 653656
<220> FEATURE:
<221> NAME/KEY: misc_feature
<222> LOCATION: (1)..(92)
<223> OTHER INFORMATION: Also Known As Ceres ME LINE ME21445
<220> FEATURE:
<221> NAME/KEY: misc_feature
<222> LOCATION: (20)..(61)
<223> OTHER INFORMATION: Pfam Name: HLH; Pfam Description:
      Helix-loop-helix DNA-binding domain

<400> SEQUENCE: 93

Met Ser Ser Arg Arg Ser Arg Ser Arg Gln Thr Ser Ser Ser Arg Asn
1               5                   10                  15

Ile Thr Asp Asp Gln Ile Asn Asp Leu Val Ser Lys Leu Gln Gln Leu
            20                  25                  30

Leu Pro Glu Ile Arg Asp Arg Arg Ser Asp Lys Val Ser Ala Ser Lys
        35                  40                  45

Val Leu Gln Glu Thr Cys Asn Tyr Ile Arg Ser Leu His Arg Glu Val
    50                  55                  60

Asp Asp Leu Ser Glu Arg Leu Ser Glu Leu Leu Ala Thr Thr Asp Thr
65                  70                  75                  80

Ala Gln Ala Ala Ile Ile Arg Asn Leu Leu Met Gln
                85                  90
```

```
<210> SEQ ID NO 94
<211> LENGTH: 701
<212> TYPE: DNA
<213> ORGANISM: Triticum aestivum
<220> FEATURE:
<221> NAME/KEY: misc_feature
<222> LOCATION: (1)..(701)
<223> OTHER INFORMATION: Ceres CLONE ID no. 733804
<220> FEATURE:
<221> NAME/KEY: misc_feature
<222> LOCATION: (1)..(701)
<223> OTHER INFORMATION: Also Known As Ceres ME LINE ME08386
<220> FEATURE:
<221> NAME/KEY: CDS
<222> LOCATION: (180)..(456)
<223> OTHER INFORMATION: Referenced by SEQ ID NO: 95

<400> SEQUENCE: 94
atgcacaact tgtcttccct ctcttccaac accacttctt cttagttcct ctccgtccct     60
gtctgccacc acttctgtct ctcaaacttg tctcactcca accataaacc ctcactgtct    120
tgggctctct ctgccaagca tccaattcct aagtacatcc gatcactcac atttgcagtg    180
atgtcgagcc gtaggtcaag gtcaaggcag tccggctcgt cgaggatcac cgacgagcaa    240
atcagcgacc ttgtctccaa gttgcaggac ctccttcccg aggcgcgtct ccggggcaat    300
```

-continued

```
gatagagtgc catcttcaag ggtgctgcag gagacgtgca cctacatcag gagcttgcac    360
cgggaggtgg acgacctgag cgagaggctg tcggagctgc tggcgacctc ggacatgagc    420
agcgcgcaag cggccatcat ccgcagcttg ctgatgtaga gccggctccc atgcagtgcg    480
caggcgcctc gtcgctgtct tgctgagcgc acaagcctga atttgagcgt ttgtagccta    540
gggagcgatc tttaattagt accggagttg caggttacct acttaatccg cgtgtgtgcg    600
ctgtcgtcgt gtcatcatcg tyttaatcag gcccatcttt tttgtgtgtg tacttaaatc    660
aagtcgttaa atcaaacccc gcccgtggtt ggtgcaagtt g                        701
```

```
<210> SEQ ID NO 95
<211> LENGTH: 92
<212> TYPE: PRT
<213> ORGANISM: Triticum aestivum
<220> FEATURE:
<221> NAME/KEY: misc_feature
<222> LOCATION: (1)..(92)
<223> OTHER INFORMATION: Ceres CLONE ID no. 733804
<220> FEATURE:
<221> NAME/KEY: misc_feature
<222> LOCATION: (1)..(92)
<223> OTHER INFORMATION: Also Known As Ceres ME LINE ME08386
<220> FEATURE:
<221> NAME/KEY: misc_feature
<222> LOCATION:
<223> OTHER INFORMATION: Phenotype: INFLORESCENCE
      Useful for making ornamental plants
      with modified flowers
<220> FEATURE:
<221> NAME/KEY: misc_feature
<222> LOCATION:
<223> OTHER INFORMATION: Phenotype: Low Nitrate
      Useful for making plants tolerant to low nitrogen

<400> SEQUENCE: 95
```

Met Ser Ser Arg Arg Ser Arg Ser Arg Gln Ser Gly Ser Ser Arg Ile
1               5                   10                  15

Thr Asp Glu Gln Ile Ser Asp Leu Val Ser Lys Leu Gln Asp Leu Leu
            20                  25                  30

Pro Glu Ala Arg Leu Arg Gly Asn Asp Arg Val Pro Ser Ser Arg Val
        35                  40                  45

Leu Gln Glu Thr Cys Thr Tyr Ile Arg Ser Leu His Arg Glu Val Asp
    50                  55                  60

Asp Leu Ser Glu Arg Leu Ser Glu Leu Leu Ala Thr Ser Asp Met Ser
65                  70                  75                  80

Ser Ala Gln Ala Ala Ile Ile Arg Ser Leu Leu Met
                85                  90

```
<210> SEQ ID NO 96
<211> LENGTH: 545
<212> TYPE: DNA
<213> ORGANISM: Arabidopsis thaliana
<220> FEATURE:
<221> NAME/KEY: misc_feature
<222> LOCATION: (1)..(545)
<223> OTHER INFORMATION: Ceres CLONE ID no. 8607
<220> FEATURE:
<221> NAME/KEY: misc_feature
<222> LOCATION: (1)..(545)
<223> OTHER INFORMATION: Also Known As Ceres ME LINE ME03973
<220> FEATURE:
<221> NAME/KEY: CDS
<222> LOCATION: (95)..(377)
<223> OTHER INFORMATION: Referenced by SEQ ID NO: 97
```

```
<400> SEQUENCE: 96 ctcccttttct ttcgacaagc acaaacaaag ccatcaagag aagaaagcct tttcttggat      60
tcacatatat ataagaatat tttttcaaat caaacatgtc ttctagcaga aggtcgagac     120
aagcaagctc atcatcaaga attagcgatg accagatcac tgatctcatc tcaaagctcc     180
gacagtccat tccggagatt cgccagaacc gtcgttccaa cacgtatca gcgtcgaaag      240 tgttacaaga gacttgcaac tacataagaa acttgaacaa ggaagccgat gacctcagtg     300
atcgattgac tcagcttctg gaatccattg atcctaatag cccacaagcc gcagttatta     360
ggagcttgat taatggataa ttaagatata aattgattag ttgtgcttta tatatataag     420
cttaaaatct cgttgggagg ttgatccatc agggtgttgc ataattatat atctatttta     480
tgtttcttat atattattta caatcctatc tagttagggt tcatattttg accctttttt     540
ggttt                                                                 545

<210> SEQ ID NO 97
<211> LENGTH: 94
<212> TYPE: PRT
<213> ORGANISM: Arabidopsis thaliana
<220> FEATURE:
<221> NAME/KEY: misc_feature
<222> LOCATION: (1)..(94)
<223> OTHER INFORMATION: Ceres CLONE ID no. 8607
<220> FEATURE:
<221> NAME/KEY: misc_feature
<222> LOCATION: (1)..(94)
<223> OTHER INFORMATION: Also Known As Ceres ME LINE ME03973
<220> FEATURE:
<221> NAME/KEY: misc_feature
<222> LOCATION:
<223> OTHER INFORMATION: Phenotype: Low Nitrate
      Useful for making plants tolerant to low nitrogen

<400> SEQUENCE: 97

Met Ser Ser Ser Arg Arg Ser Arg Gln Ala Ser Ser Ser Ser Arg Ile
1               5                   10                  15

Ser Asp Asp Gln Ile Thr Asp Leu Ile Ser Lys Leu Arg Gln Ser Ile
            20                  25                  30

Pro Glu Ile Arg Gln Asn Arg Arg Ser Asn Thr Val Ser Ala Ser Lys
        35                  40                  45

Val Leu Gln Glu Thr Cys Asn Tyr Ile Arg Asn Leu Asn Lys Glu Ala
    50                  55                  60

Asp Asp Leu Ser Asp Arg Leu Thr Gln Leu Leu Glu Ser Ile Asp Pro
65                  70                  75                  80

Asn Ser Pro Gln Ala Ala Val Ile Arg Ser Leu Ile Asn Gly
                85                  90

<210> SEQ ID NO 98
<211> LENGTH: 91
<212> TYPE: PRT
<213> ORGANISM: Oryza sativa subsp. japonica
<220> FEATURE:
<221> NAME/KEY: misc_feature
<222> LOCATION: (1)..(91)
<223> OTHER INFORMATION: Public GI no. 78708592
<220> FEATURE:
<221> NAME/KEY: misc_feature
<222> LOCATION: (1)..(91)
<223> OTHER INFORMATION: Functional Homolog of CERES CLONE ID no.
      653656 at SEQ ID NO. 93
      with e-value of 1.49E-25 and percent identity of 73.8
```

```
<220> FEATURE:
<221> NAME/KEY: misc_feature
<222> LOCATION: (1)..(91)
<223> OTHER INFORMATION: Functional Homolog of CERES CLONE ID no.
      733804 at SEQ ID NO. 95
      with e-value of 2.50E-32 and percent identity of 82.2
<220> FEATURE:
<221> NAME/KEY: misc_feature
<222> LOCATION: (1)..(91)
<223> OTHER INFORMATION: Functional Homolog of CERES CLONE ID no. 8607
      at SEQ ID NO. 97
      with e-value of 7.09E-19 and percent identity of 56.8

<400> SEQUENCE: 98

Met Ser Arg Arg Ser Arg Ser Arg Ala Ser Ser Ala Ala Arg Ile Thr
1               5                   10                  15

Asp Glu Gln Ile Gly Asp Leu Val Ser Lys Leu Gln Ala Leu Leu Pro
            20                  25                  30

Glu Ala Arg Leu Arg Ser Asn Asp Arg Val Pro Ser Ala Arg Val Leu
        35                  40                  45

Gln Glu Thr Cys Ser Tyr Ile Arg Ser Leu His Arg Glu Val Asp Asp
    50                  55                  60

Leu Ser Glu Arg Leu Ala Glu Leu Leu Ala Ala Asp Val Ser Thr
65                  70                  75                  80

Ala Gln Ala Ala Val Ile Arg Gly Leu Leu Met
                85                  90

<210> SEQ ID NO 99
<211> LENGTH: 92
<212> TYPE: PRT
<213> ORGANISM: Glycine max
<220> FEATURE:
<221> NAME/KEY: misc_feature
<222> LOCATION: (1)..(92)
<223> OTHER INFORMATION: Ceres CLONE ID no. 663844
<220> FEATURE:
<221> NAME/KEY: misc_feature
<222> LOCATION: (1)..(92)
<223> OTHER INFORMATION: Functional Homolog of CERES CLONE ID no. 519
      at SEQ ID NO. 87
      with e-value of 3.30E-30 and percent identity of 76
<220> FEATURE:
<221> NAME/KEY: misc_feature
<222> LOCATION: (1)..(92)
<223> OTHER INFORMATION: Functional Homolog of CERES CLONE ID no. 4734
      at SEQ ID NO. 85
      with e-value of 2.49E-23 and percent identity of 69.6
<220> FEATURE:
<221> NAME/KEY: misc_feature
<222> LOCATION: (1)..(92)
<223> OTHER INFORMATION: Functional Homolog of CERES CLONE ID no. 8607
      at SEQ ID NO. 97
      with e-value of 5.29E-23 and percent identity of 67.4
<220> FEATURE:
<221> NAME/KEY: misc_feature
<222> LOCATION: (1)..(92)
<223> OTHER INFORMATION: Functional Homolog of CERES CLONE ID no.
      336524 at SEQ ID NO. 83
      with e-value of 1.70E-17 and percent identity of 64.8
<220> FEATURE:
<221> NAME/KEY: misc_feature
<222> LOCATION: (1)..(92)
<223> OTHER INFORMATION: Functional Homolog of CERES CLONE ID no.
      560681 at SEQ ID NO. 89
      with e-value of 6.99E-28 and percent identity of 80.6
<220> FEATURE:
<221> NAME/KEY: misc_feature
<222> LOCATION: (1)..(92)
<223> OTHER INFORMATION: Functional Homolog of CERES CLONE ID no.
      560948 at SEQ ID NO. 91
      with e-value of 3.90E-27 and percent identity of 77.7
```

-continued

```
<220> FEATURE:
<221> NAME/KEY: misc_feature
<222> LOCATION: (1)..(92)
<223> OTHER INFORMATION: Functional Homolog of CERES CLONE ID no.
      653656 at SEQ ID NO. 93
      with e-value of 8.60E-39 and percent identity of 96.7
<220> FEATURE:
<221> NAME/KEY: misc_feature
<222> LOCATION: (1)..(92)
<223> OTHER INFORMATION: Functional Homolog of CERES CLONE ID no.
      733804 at SEQ ID NO. 95
      with e-value of 1.49E-27 and percent identity of 78.8

<400> SEQUENCE: 99

Met Ser Ser Arg Arg Ser Arg Ser Arg Gln Thr Ser Ser Ser Arg Asn
1               5                   10                  15

Ile Thr Asp Asp Gln Ile Asn Asp Leu Val Ser Lys Leu Gln Gln Leu
            20                  25                  30

Leu Pro Glu Ile Arg Asp Arg Ser Asp Lys Val Ser Ala Ser Lys
        35                  40                  45

Val Leu Gln Glu Thr Cys Asn Tyr Ile Arg Ser Leu His Arg Glu Val
50                  55                  60

Gly Asp Leu Ser Glu Arg Leu Ser Glu Leu Leu Asp Thr Thr Asp Thr
65                  70                  75                  80

Ala Gln Ala Ala Ile Ile Arg Asn Leu Leu Met Gln
            85                  90

<210> SEQ ID NO 100
<211> LENGTH: 276
<212> TYPE: DNA
<213> ORGANISM: Populus balsamifera subsp. trichocarpa
<220> FEATURE:
<221> NAME/KEY: misc_feature
<222> LOCATION: (1)..(276)
<223> OTHER INFORMATION: Ceres GDNA ANNOT ID no. 1468218
<220> FEATURE:
<221> NAME/KEY: misc_feature
<222> LOCATION: (1)..(276)
<223> OTHER INFORMATION: Functional Homolog of CERES CLONE ID no.
      653656 at SEQ ID NO. 93
      with e-value of 6.40E-34 and percent identity of 87.9
<220> FEATURE:
<221> NAME/KEY: misc_feature
<222> LOCATION: (1)..(276)
<223> OTHER INFORMATION: Functional Homolog of CERES CLONE ID no.
      733804 at SEQ ID NO. 95
      with e-value of 3.00E-27 and percent identity of 74.4
<220> FEATURE:
<221> NAME/KEY: misc_feature
<222> LOCATION: (1)..(276)
<223> OTHER INFORMATION: Functional Homolog of CERES CLONE ID no. 8607
      at SEQ ID NO. 97
      with e-value of 4.09E-23 and percent identity of 67.8

<400> SEQUENCE: 100
atgtctagcc gaaggtcacg atcaaggcaa tcaagtagtt caagaatcag tgatgatcag    60
atccttgatc ttgttacaaa gttgcaacaa cttcttcctg agattcgtaa caggcgttct   120
gacaaggttt cggctgccaa gatcttgcag gagacatgca actatattaa aagcttgcat   180
agagaggttg gtgatcttag cgagcggctg tctgagctat ggaaacaac tgatacagcc    240 caagctgcaa taatcaggaa cttacttatg caatag                             276

<210> SEQ ID NO 101
<211> LENGTH: 91
<212> TYPE: PRT
<213> ORGANISM: Populus balsamifera subsp. trichocarpa
```

```
<220> FEATURE:
<221> NAME/KEY: misc_feature
<222> LOCATION: (1)..(91)
<223> OTHER INFORMATION: Ceres GDNA ANNOT ID no. 1468218
<220> FEATURE:
<221> NAME/KEY: misc_feature
<222> LOCATION: (1)..(91)
<223> OTHER INFORMATION: Functional Homolog of CERES CLONE ID no.
      653656 at SEQ ID NO. 93
      with e-value of 6.40E-34 and percent identity of 87.9
<220> FEATURE:
<221> NAME/KEY: misc_feature
<222> LOCATION: (1)..(91)
<223> OTHER INFORMATION: Functional Homolog of CERES CLONE ID no.
      733804 at SEQ ID NO. 95
      with e-value of 3.00E-27 and percent identity of 74.4
<220> FEATURE:
<221> NAME/KEY: misc_feature
<222> LOCATION: (1)..(91)
<223> OTHER INFORMATION: Functional Homolog of CERES CLONE ID no. 8607
      at SEQ ID NO. 97
      with e-value of 4.09E-23 and percent identity of 67.8

<400> SEQUENCE: 101

Met Ser Ser Arg Arg Ser Arg Ser Arg Gln Ser Ser Ser Arg Ile
1               5                   10                  15

Ser Asp Asp Gln Ile Leu Asp Leu Val Thr Lys Leu Gln Gln Leu Leu
                20                  25                  30

Pro Glu Ile Arg Asn Arg Arg Ser Asp Lys Val Ser Ala Ala Lys Ile
            35                  40                  45

Leu Gln Glu Thr Cys Asn Tyr Ile Lys Ser Leu His Arg Glu Val Gly
        50                  55                  60

Asp Leu Ser Glu Arg Leu Ser Glu Leu Leu Glu Thr Thr Asp Thr Ala
65                  70                  75                  80

Gln Ala Ala Ile Ile Arg Asn Leu Leu Met Gln
                85                  90

<210> SEQ ID NO 102
<211> LENGTH: 91
<212> TYPE: PRT
<213> ORGANISM: Triticum aestivum
<220> FEATURE:
<221> NAME/KEY: misc_feature
<222> LOCATION: (1)..(91)
<223> OTHER INFORMATION: Ceres CLONE ID no. 703180
<220> FEATURE:
<221> NAME/KEY: misc_feature
<222> LOCATION: (1)..(91)
<223> OTHER INFORMATION: Functional Homolog of CERES CLONE ID no. 519
      at SEQ ID NO. 87
      with e-value of 9.19E-26 and percent identity of 72.7
<220> FEATURE:
<221> NAME/KEY: misc_feature
<222> LOCATION: (1)..(91)
<223> OTHER INFORMATION: Functional Homolog of CERES CLONE ID no. 4734
      at SEQ ID NO. 85
      with e-value of 1.09E-29 and percent identity of 76.6
<220> FEATURE:
<221> NAME/KEY: misc_feature
<222> LOCATION: (1)..(91)
<223> OTHER INFORMATION: Functional Homolog of CERES CLONE ID no. 8607
      at SEQ ID NO. 97
      with e-value of 4.79E-29 and percent identity of 75.5
<220> FEATURE:
<221> NAME/KEY: misc_feature
<222> LOCATION: (1)..(91)
<223> OTHER INFORMATION: Functional Homolog of CERES CLONE ID no.
      336524 at SEQ ID NO. 83
      with e-value of 9.99E-20 and percent identity of 64.9
```

```
<220> FEATURE:
<221> NAME/KEY: misc_feature
<222> LOCATION: (1)..(91)
<223> OTHER INFORMATION: Functional Homolog of CERES CLONE ID no.
      560681 at SEQ ID NO. 89
      with e-value of 5.79E-40 and percent identity of 100
<220> FEATURE:
<221> NAME/KEY: misc_feature
<222> LOCATION: (1)..(91)
<223> OTHER INFORMATION: Functional Homolog of CERES CLONE ID no.
      560948 at SEQ ID NO. 91
      with e-value of 4.39E-35 and percent identity of 89
<220> FEATURE:
<221> NAME/KEY: misc_feature
<222> LOCATION: (1)..(91)
<223> OTHER INFORMATION: Functional Homolog of CERES CLONE ID no.
      653656 at SEQ ID NO. 93
      with e-value of 1.29E-28 and percent identity of 81.8
<220> FEATURE:
<221> NAME/KEY: misc_feature
<222> LOCATION: (1)..(91)
<223> OTHER INFORMATION: Functional Homolog of CERES CLONE ID no.
      733804 at SEQ ID NO. 95
      with e-value of 4.39E-26 and percent identity of 72.2

<400> SEQUENCE: 102

Met Ser Ser Arg Arg Ser Arg Gln Gln Ser Ala Ser Thr Arg Ile Ser
1               5                   10                  15

Asp Asp Gln Ile Ile Asp Leu Val Ser Lys Leu Arg Gln Leu Val Pro
            20                  25                  30

Glu Ile Arg Asp Arg Arg Ser Asp Lys Val Ser Ala Ser Lys Val Leu
        35                  40                  45

Gln Glu Thr Cys Asn Tyr Ile Arg Ser Leu His Arg Glu Val Asp Asp
    50                  55                  60

Leu Ser Glu Arg Leu Ser Gln Leu Leu Ala Thr Ile Asp Ala Asp Ser
65                  70                  75                  80

Pro Glu Ala Ala Ile Ile Arg Ser Leu Ile Asn
                85                  90

<210> SEQ ID NO 103
<211> LENGTH: 86
<212> TYPE: PRT
<213> ORGANISM: Brassica napus
<220> FEATURE:
<221> NAME/KEY: misc_feature
<222> LOCATION: (1)..(86)
<223> OTHER INFORMATION: Ceres CLONE ID no. 945972
<220> FEATURE:
<221> NAME/KEY: misc_feature
<222> LOCATION: (1)..(86)
<223> OTHER INFORMATION: Functional Homolog of CERES CLONE ID no. 519
      at SEQ ID NO. 87
      with e-value of 4.60E-24 and percent identity of 69.8
<220> FEATURE:
<221> NAME/KEY: misc_feature
<222> LOCATION: (1)..(86)
<223> OTHER INFORMATION: Functional Homolog of CERES CLONE ID no. 4734
      at SEQ ID NO. 85
      with e-value of 1.60E-21 and percent identity of 68.6
<220> FEATURE:
<221> NAME/KEY: misc_feature
<222> LOCATION: (1)..(86)
<223> OTHER INFORMATION: Functional Homolog of CERES CLONE ID no. 8607
      at SEQ ID NO. 97
      with e-value of 4.69E-22 and percent identity of 68.6
<220> FEATURE:
<221> NAME/KEY: misc_feature
<222> LOCATION: (1)..(86)
<223> OTHER INFORMATION: Functional Homolog of CERES CLONE ID no.
      336524 at SEQ ID NO. 83
      with e-value of 3.70E-15 and percent identity of 56.5
```

```
<220> FEATURE:
<221> NAME/KEY: misc_feature
<222> LOCATION: (1)..(86)
<223> OTHER INFORMATION: Functional Homolog of CERES CLONE ID no.
      560681 at SEQ ID NO. 89
      with e-value of 3.99E-25 and percent identity of 73.8
<220> FEATURE:
<221> NAME/KEY: misc_feature
<222> LOCATION: (1)..(86)
<223> OTHER INFORMATION: Functional Homolog of CERES CLONE ID no.
      560948 at SEQ ID NO. 91
      with e-value of 5.90E-24 and percent identity of 71.9
<220> FEATURE:
<221> NAME/KEY: misc_feature
<222> LOCATION: (1)..(86)
<223> OTHER INFORMATION: Functional Homolog of CERES CLONE ID no.
      653656 at SEQ ID NO. 93
      with e-value of 8.29E-25 and percent identity of 76.8
<220> FEATURE:
<221> NAME/KEY: misc_feature
<222> LOCATION: (1)..(86)
<223> OTHER INFORMATION: Functional Homolog of CERES CLONE ID no.
      733804 at SEQ ID NO. 95
      with e-value of 1.39E-24 and percent identity of 71.7
<220> FEATURE:
<221> NAME/KEY: misc_feature
<222> LOCATION: (43)..(43)
<223> OTHER INFORMATION: Xaa is any aa, unknown, or other
<220> FEATURE:
<221> NAME/KEY: misc_feature
<222> LOCATION: (85)..(85)
<223> OTHER INFORMATION: Xaa is any aa, unknown, or other

<400> SEQUENCE: 103

Met Ser Ser Arg Arg Ser Ser Cys Ser Arg Gln Ser Gly Ser Ser Arg
1               5                   10                  15

Ile Ser Asp Asp Gln Ile Ser Asp Leu Val Thr Lys Leu Gln His Leu
            20                  25                  30

Ile Pro Glu Leu Arg Arg Arg Ser Asp Xaa Val Ser Ala Ser Lys
        35                  40                  45

Val Leu Gln Glu Thr Cys Asn Tyr Ile Arg Asn Leu His Arg Glu Val
    50                  55                  60

Asp Asp Leu Ser Asp Arg Leu Ser Glu Phe Leu Ala Ser Thr Asp Asp
65                  70                  75                  80

Asn Ser Ala Glu Xaa Ala
                85

<210> SEQ ID NO 104
<211> LENGTH: 273
<212> TYPE: DNA
<213> ORGANISM: Populus balsamifera subsp. trichocarpa
<220> FEATURE:
<221> NAME/KEY: misc_feature
<222> LOCATION: (1)..(273)
<223> OTHER INFORMATION: Ceres GDNA ANNOT ID No. 1530225
<220> FEATURE:
<221> NAME/KEY: misc_feature
<222> LOCATION: (1)..(273)
<223> OTHER INFORMATION: Functional Homolog of CERES CLONE ID no.
      653656 at SEQ ID NO. 93
      with e-value of 8.10E-27 and percent identity of 80.6
<220> FEATURE:
<221> NAME/KEY: misc_feature
<222> LOCATION: (1)..(273)
<223> OTHER INFORMATION: Functional Homolog of CERES CLONE ID no.
      733804 at SEQ ID NO. 95
      with e-value of 6.50E-25 and percent identity of 71.1
```

```
<220> FEATURE:
<221> NAME/KEY: misc_feature
<222> LOCATION: (1)..(273)
<223> OTHER INFORMATION: Functional Homolog of CERES CLONE ID no. 8607
      at SEQ ID NO. 97
      with e-value of 2.10E-26 and percent identity of 75.0

<400> SEQUENCE: 104
atgtctagca gaaggccaag gcaatctagc gttccaagga tcactgatga tcagatcatc    60
gaccttgtct ccaaattacg ccagcttctc cctgagatta gtcaaggcg ctccgataag    120 gtatcagctt ccaaggtcct acaagagact tgcaattata tcaggaactt gcacagggag   180
gttgatgact aagtgagcg attgtctcag cttttggcaa caattgatgc tgatagtcct    240
gaagcagcga ataataaggag tttaattatg taa                               273

<210> SEQ ID NO 105
<211> LENGTH: 90
<212> TYPE: PRT
<213> ORGANISM: Populus balsamifera subsp. trichocarpa
<220> FEATURE:
<221> NAME/KEY: misc_feature
<222> LOCATION: (1)..(90)
<223> OTHER INFORMATION: Ceres GDNA ANNOT ID No. 1530225
<220> FEATURE:
<221> NAME/KEY: misc_feature
<222> LOCATION: (1)..(90)
<223> OTHER INFORMATION: Functional Homolog of CERES CLONE ID no.
      653656 at SEQ ID NO. 93
      with e-value of 8.10E-27 and percent identity of 80.6
<220> FEATURE:
<221> NAME/KEY: misc_feature
<222> LOCATION: (1)..(90)
<223> OTHER INFORMATION: Functional Homolog of CERES CLONE ID no.
      733804 at SEQ ID NO. 95
      with e-value of 6.50E-25 and percent identity of 71.1
<220> FEATURE:
<221> NAME/KEY: misc_feature
<222> LOCATION: (1)..(90)
<223> OTHER INFORMATION: Functional Homolog of CERES CLONE ID no. 8607
      at SEQ ID NO. 97
      with e-value of 2.10E-26 and percent identity of 75.0

<400> SEQUENCE: 105

Met Ser Ser Arg Arg Pro Arg Gln Ser Ser Val Pro Arg Ile Thr Asp
1               5                   10                  15

Asp Gln Ile Ile Asp Leu Val Ser Lys Leu Arg Gln Leu Leu Pro Glu
            20                  25                  30

Ile Ser Gln Arg Arg Ser Asp Lys Val Ser Ala Ser Lys Val Leu Gln
        35                  40                  45

Glu Thr Cys Asn Tyr Ile Arg Asn Leu His Arg Glu Val Asp Asp Leu
    50                  55                  60

Ser Glu Arg Leu Ser Gln Leu Leu Ala Thr Ile Asp Ala Asp Ser Pro
65                  70                  75                  80

Glu Ala Ala Ile Ile Arg Ser Leu Ile Met
                85                  90

<210> SEQ ID NO 106
<211> LENGTH: 92
<212> TYPE: PRT
<213> ORGANISM: Arabidopsis thaliana
<220> FEATURE:
<221> NAME/KEY: misc_feature
<222> LOCATION: (1)..(92)
<223> OTHER INFORMATION: Public GI no. 22331645
```

```
<220> FEATURE:
<221> NAME/KEY: misc_feature
<222> LOCATION: (1)..(92)
<223> OTHER INFORMATION: Functional Homolog of CERES CLONE ID no. 519
      at SEQ ID NO. 87
      with e-value of 3.00E-27 and percent identity of 69.5
<220> FEATURE:
<221> NAME/KEY: misc_feature
<222> LOCATION: (1)..(92)
<223> OTHER INFORMATION: Functional Homolog of CERES CLONE ID no. 4734
      at SEQ ID NO. 85
      with e-value of 3.70E-22 and percent identity of 64.4
<220> FEATURE:
<221> NAME/KEY: misc_feature
<222> LOCATION: (1)..(92)
<223> OTHER INFORMATION: Functional Homolog of CERES CLONE ID no. 8607
      at SEQ ID NO. 97
      with e-value of 9.79E-22 and percent identity of 63.6
<220> FEATURE:
<221> NAME/KEY: misc_feature
<222> LOCATION: (1)..(92)
<223> OTHER INFORMATION: Functional Homolog of CERES CLONE ID no.
      336524 at SEQ ID NO. 83
      with e-value of 1.09E-15 and percent identity of 54.6
<220> FEATURE:
<221> NAME/KEY: misc_feature
<222> LOCATION: (1)..(92)
<223> OTHER INFORMATION: Functional Homolog of CERES CLONE ID no.
      560681 at SEQ ID NO. 89
      with e-value of 4.30E-21 and percent identity of 64.7
<220> FEATURE:
<221> NAME/KEY: misc_feature
<222> LOCATION: (1)..(92)
<223> OTHER INFORMATION: Functional Homolog of CERES CLONE ID no.
      560948 at SEQ ID NO. 91
      with e-value of 3.30E-21 and percent identity of 64.4
<220> FEATURE:
<221> NAME/KEY: misc_feature
<222> LOCATION: (1)..(92)
<223> OTHER INFORMATION: Functional Homolog of CERES CLONE ID no.
      653656 at SEQ ID NO. 93
      with e-value of 1.29E-26 and percent identity of 72.5
<220> FEATURE:
<221> NAME/KEY: misc_feature
<222> LOCATION: (1)..(92)
<223> OTHER INFORMATION: Functional Homolog of CERES CLONE ID no.
      733804 at SEQ ID NO. 95
      with e-value of 3.60E-24 and percent identity of 71.1

<400> SEQUENCE: 106

Met Ser Ser Arg Lys Ser Arg Ser Arg Gln Thr Gly Ala Ser Met Ile
1               5                   10                  15

Thr Asp Glu Gln Ile Asn Asp Leu Val Leu Gln Leu His Arg Leu Leu
            20                  25                  30

Pro Glu Leu Ala Asn Asn Arg Arg Ser Gly Lys Val Ser Ala Ser Arg
        35                  40                  45

Val Leu Gln Glu Thr Cys Ser Tyr Ile Arg Asn Leu Ser Lys Glu Val
    50                  55                  60

Asp Asp Leu Ser Glu Arg Leu Ser Gln Leu Leu Glu Ser Thr Asp Ser
65                  70                  75                  80

Ala Gln Ala Ala Leu Ile Arg Ser Leu Leu Met Gln
                85                  90

<210> SEQ ID NO 107
<211> LENGTH: 273
<212> TYPE: DNA
<213> ORGANISM: Populus balsamifera subsp. trichocarpa
<220> FEATURE:
<221> NAME/KEY: misc_feature
<222> LOCATION: (1)..(273)
<223> OTHER INFORMATION: Ceres GDNA ANNOT ID no. 1449794
```

```
<220> FEATURE:
<221> NAME/KEY: misc_feature
<222> LOCATION: (1)..(273)
<223> OTHER INFORMATION: Functional Homolog of CERES CLONE ID no.
      653656 at SEQ ID NO. 93
      with e-value of 1.70E-26 and percent identity of 79.5
<220> FEATURE:
<221> NAME/KEY: misc_feature
<222> LOCATION: (1)..(273)
<223> OTHER INFORMATION: Functional Homolog of CERES CLONE ID no.
      733804 at SEQ ID NO. 95
      with e-value of 1.70E-24 and percent identity of 70
<220> FEATURE:
<221> NAME/KEY: misc_feature
<222> LOCATION: (1)..(273)
<223> OTHER INFORMATION: Functional Homolog of CERES CLONE ID no. 8607
      at SEQ ID NO. 97
      with e-value of 5.69E-26 and percent identity of 73.8

<400> SEQUENCE: 107
atgtctagca gaaggtcaag gcagtctagt gttccaagga tcactgatga tcaaatcatc    60
caccttgtct ccaaattacg ccagcttctc cctgagattc gtcaaaggcg ctccgataag   120
gtatcagctt ctaaggtcct acaagaaact tgcaactata tcaagaactt gcatagggag   180
gttgatgatt taagtgagcg attgtctcag cttttggcaa caattgattc tgatagtcct   240
gaagctgaga ataataaggag tttaattatg taa                               273

<210> SEQ ID NO 108
<211> LENGTH: 90
<212> TYPE: PRT
<213> ORGANISM: Populus balsamifera subsp. trichocarpa
<220> FEATURE:
<221> NAME/KEY: misc_feature
<222> LOCATION: (1)..(90)
<223> OTHER INFORMATION: Ceres GDNA ANNOT ID no. 1449794
<220> FEATURE:
<221> NAME/KEY: misc_feature
<222> LOCATION: (1)..(90)
<223> OTHER INFORMATION: Functional Homolog of CERES CLONE ID no.
      653656 at SEQ ID NO. 93
      with e-value of 1.70E-26 and percent identity of 79.5
<220> FEATURE:
<221> NAME/KEY: misc_feature
<222> LOCATION: (1)..(90)
<223> OTHER INFORMATION: Functional Homolog of CERES CLONE ID no.
      733804 at SEQ ID NO. 95
      with e-value of 1.70E-24 and percent identity of 70
<220> FEATURE:
<221> NAME/KEY: misc_feature
<222> LOCATION: (1)..(90)
<223> OTHER INFORMATION: Functional Homolog of CERES CLONE ID no. 8607
      at SEQ ID NO. 97
      with e-value of 5.69E-26 and percent identity of 73.8

<400> SEQUENCE: 108

Met Ser Ser Arg Arg Ser Arg Gln Ser Ser Val Pro Arg Ile Thr Asp
1               5                   10                  15

Asp Gln Ile Ile His Leu Val Ser Lys Leu Arg Gln Leu Leu Pro Glu
            20                  25                  30

Ile Arg Gln Arg Arg Ser Asp Lys Val Ser Ala Ser Lys Val Leu Gln
        35                  40                  45

Glu Thr Cys Asn Tyr Ile Lys Asn Leu His Arg Glu Val Asp Leu
    50                  55                  60

Ser Glu Arg Leu Ser Gln Leu Leu Ala Thr Ile Asp Ser Asp Ser Pro
65                  70                  75                  80

Glu Ala Glu Ile Ile Arg Ser Leu Ile Met
                85                  90
```

```
<210> SEQ ID NO 109
<211> LENGTH: 88
<212> TYPE: PRT
<213> ORGANISM: Oryza sativa subsp. japonica
<220> FEATURE:
<221> NAME/KEY: misc_feature
<222> LOCATION: (1)..(88)
<223> OTHER INFORMATION: Public GI no. 31431968
<220> FEATURE:
<221> NAME/KEY: misc_feature
<222> LOCATION: (1)..(88)
<223> OTHER INFORMATION: Functional Homolog of CERES CLONE ID no. 519
      at SEQ ID NO. 87
      with e-value of 1.99E-16 and percent identity of 65.8
<220> FEATURE:
<221> NAME/KEY: misc_feature
<222> LOCATION: (1)..(88)
<223> OTHER INFORMATION: Functional Homolog of CERES CLONE ID no. 4734
      at SEQ ID NO. 85
      with e-value of 1.49E-16 and percent identity of 51.1
<220> FEATURE:
<221> NAME/KEY: misc_feature
<222> LOCATION: (1)..(88)
<223> OTHER INFORMATION: Functional Homolog of CERES CLONE ID no. 8607
      at SEQ ID NO. 97
      with e-value of 2.49E-16 and percent identity of 50.6
<220> FEATURE:
<221> NAME/KEY: misc_feature
<222> LOCATION: (1)..(88)
<223> OTHER INFORMATION: Functional Homolog of CERES CLONE ID no.
      336524 at SEQ ID NO. 83
      with e-value of 1.60E-28 and percent identity of 84.3
<220> FEATURE:
<221> NAME/KEY: misc_feature
<222> LOCATION: (1)..(88)
<223> OTHER INFORMATION: Functional Homolog of CERES CLONE ID no.
      560681 at SEQ ID NO. 89
      with e-value of 1.29E-19 and percent identity of 62.3
<220> FEATURE:
<221> NAME/KEY: misc_feature
<222> LOCATION: (1)..(88)
<223> OTHER INFORMATION: Functional Homolog of CERES CLONE ID no.
      560948 at SEQ ID NO. 91
      with e-value of 6.39E-18 and percent identity of 60
<220> FEATURE:
<221> NAME/KEY: misc_feature
<222> LOCATION: (1)..(88)
<223> OTHER INFORMATION: Functional Homolog of CERES CLONE ID no.
      653656 at SEQ ID NO. 93
      with e-value of 8.20E-18 and percent identity of 64.1
<220> FEATURE:
<221> NAME/KEY: misc_feature
<222> LOCATION: (1)..(88)
<223> OTHER INFORMATION: Functional Homolog of CERES CLONE ID no.
      733804 at SEQ ID NO. 95
      with e-value of 8.79E-21 and percent identity of 64.2

<400> SEQUENCE: 109

Met Ser Gly Arg Arg Ala Ser Gly Arg Ile Thr Asp Asp Glu Ile Asn
1               5                   10                  15

Glu Leu Ile Ser Lys Leu Gln Ser Leu Leu Pro Glu Ser Ser Arg Arg
            20                  25                  30

Arg Gly Ala Thr Ser Arg Ser Pro Ala Thr Lys Leu Leu Lys Glu Met
        35                  40                  45

Cys Ser Tyr Ile Lys Ser Leu His Arg Glu Val Asp Asp Leu Ser Glu
    50                  55                  60

Arg Leu Ser Glu Leu Met Ala Thr Met Asp Ser Asn Ser Pro Gln Ala
65                  70                  75                  80

Asp Ile Ile Arg Ser Leu Leu Arg
                85
```

```
<210> SEQ ID NO 110
<211> LENGTH: 88
<212> TYPE: PRT
<213> ORGANISM: Oryza sativa subsp. japonica
<220> FEATURE:
<221> NAME/KEY: misc_feature
<222> LOCATION: (1)..(88)
<223> OTHER INFORMATION: Public GI no. 50912765
<220> FEATURE:
<221> NAME/KEY: misc_feature
<222> LOCATION: (1)..(88)
<223> OTHER INFORMATION: Functional Homolog of CERES CLONE ID no. 519
      at SEQ ID NO. 87
      with e-value of 2.49E-16 and percent identity of 58.5
<220> FEATURE:
<221> NAME/KEY: misc_feature
<222> LOCATION: (1)..(88)
<223> OTHER INFORMATION: Functional Homolog of CERES CLONE ID no. 4734
      at SEQ ID NO. 85
      with e-value of 2.80E-17 and percent identity of 53.4
<220> FEATURE:
<221> NAME/KEY: misc_feature
<222> LOCATION: (1)..(88)
<223> OTHER INFORMATION: Functional Homolog of CERES CLONE ID no. 8607
      at SEQ ID NO. 97
      with e-value of 1.49E-16 and percent identity of 52.9
<220> FEATURE:
<221> NAME/KEY: misc_feature
<222> LOCATION: (1)..(88)
<223> OTHER INFORMATION: Functional Homolog of CERES CLONE ID no.
      336524 at SEQ ID NO. 83
      with e-value of 3.99E-25 and percent identity of 73.2
<220> FEATURE:
<221> NAME/KEY: misc_feature
<222> LOCATION: (1)..(88)
<223> OTHER INFORMATION: Functional Homolog of CERES CLONE ID no.
      560681 at SEQ ID NO. 89
      with e-value of 4.90E-20 and percent identity of 60.4
<220> FEATURE:
<221> NAME/KEY: misc_feature
<222> LOCATION: (1)..(88)
<223> OTHER INFORMATION: Functional Homolog of CERES CLONE ID no.
      560948 at SEQ ID NO. 91
      with e-value of 1.90E-18 and percent identity of 59.3
<220> FEATURE:
<221> NAME/KEY: misc_feature
<222> LOCATION: (1)..(88)
<223> OTHER INFORMATION: Functional Homolog of CERES CLONE ID no.
      653656 at SEQ ID NO. 93
      with e-value of 5.00E-18 and percent identity of 60.7
<220> FEATURE:
<221> NAME/KEY: misc_feature
<222> LOCATION: (1)..(88)
<223> OTHER INFORMATION: Functional Homolog of CERES CLONE ID no.
      733804 at SEQ ID NO. 95
      with e-value of 4.90E-20 and percent identity of 62.7

<400> SEQUENCE: 110

Met Ser Ser Arg Arg Ser Arg Gly Ser Ile Ser Glu Glu Glu Ile
1               5                   10                  15

Asn Glu Leu Ile Ser Lys Leu Gln Ser Leu Leu Pro Asn Ser Arg Arg
                20                  25                  30

Arg Gly Ser Ser Gln Ala Ser Thr Thr Lys Leu Leu Lys Glu Thr Cys
            35                  40                  45

Asn Tyr Ile Lys Ser Leu His Arg Glu Val Asp Asp Leu Ser Asp Arg
        50                  55                  60

Leu Ser Asp Leu Met Ala Thr Met Asp His Asn Ser Pro Gly Ala Glu
65                  70                  75                  80

Ile Ile Arg Ser Ile Leu Arg Ser
                85
```

```
<210> SEQ ID NO 111
<211> LENGTH: 90
<212> TYPE: PRT
<213> ORGANISM: Zea mays
<220> FEATURE:
<221> NAME/KEY: misc_feature
<222> LOCATION: (1)..(90)
<223> OTHER INFORMATION: Ceres CLONE ID no. 486120
<220> FEATURE:
<221> NAME/KEY: misc_feature
<222> LOCATION: (1)..(90)
<223> OTHER INFORMATION: Functional Homolog of CERES CLONE ID no. 519
      at SEQ ID NO. 87
      with e-value of 1.20E-16 and percent identity of 53.57143
<220> FEATURE:
<221> NAME/KEY: misc_feature
<222> LOCATION: (1)..(90)
<223> OTHER INFORMATION: Functional Homolog of CERES CLONE ID no. 4734
      at SEQ ID NO. 85
      with e-value of and 1.50E-18 percent identity of 54.65116
<220> FEATURE:
<221> NAME/KEY: misc_feature
<222> LOCATION: (1)..(90)
<223> OTHER INFORMATION: Functional Homolog of CERES CLONE ID no. 8607
      at SEQ ID NO. 97
      with e-value of 5.40E-14 and percent identity of 48.61111
<220> FEATURE:
<221> NAME/KEY: misc_feature
<222> LOCATION: (1)..(90)
<223> OTHER INFORMATION: Functional Homolog of CERES CLONE ID no.
      336524 at SEQ ID NO. 83
      with e-value of 1.10E-24 and percent identity of 67.81609
<220> FEATURE:
<221> NAME/KEY: misc_feature
<222> LOCATION: (1)..(90)
<223> OTHER INFORMATION: Functional Homolog of CERES CLONE ID no.
      560681 at SEQ ID NO. 89
      with e-value of 1.20E-18 and percent identity of 59.77011
<220> FEATURE:
<221> NAME/KEY: misc_feature
<222> LOCATION: (1)..(90)
<223> OTHER INFORMATION: Functional Homolog of CERES CLONE ID no.
      560948 at SEQ ID NO. 91
      with e-value of 6.40E-18 and percent identity of 58.62069
<220> FEATURE:
<221> NAME/KEY: misc_feature
<222> LOCATION: (1)..(90)
<223> OTHER INFORMATION: Functional Homolog of CERES CLONE ID no.
      653656 at SEQ ID NO. 93
      with e-value of 8.70E-14 and percent identity of 60.86957
<220> FEATURE:
<221> NAME/KEY: misc_feature
<222> LOCATION: (1)..(90)
<223> OTHER INFORMATION: Functional Homolog of CERES CLONE ID no.
      733804 at SEQ ID NO. 95
      with e-value of 9.70E-15 and percent identity of 57.74648

<400> SEQUENCE: 111

Met Ser Ser Arg Arg Ser Ser His Gly Asn Ile Ser Glu Asp Glu
1               5                   10                  15

Met Asn Glu Leu Val Ser Lys Leu Gln Ala Leu Leu Pro Ser Ser Arg
                20                  25                  30

Arg Arg Arg Gly Ser Gly Gln Ala Ser Thr Ala Lys Leu Leu Lys Glu
            35                  40                  45

Thr Cys Ser Tyr Ile Lys Ser Leu Gln Arg Glu Val Asp Asp Leu Ser
    50                  55                  60

Asp Arg Leu Ser Asp Leu Leu Ser Thr Met Asp His Asn Ser Pro Ala
65                  70                  75                  80

Ala Glu Ile Ile Arg Ser Ile Leu Arg Ser
                85                  90
```

```
<210> SEQ ID NO 112
<211> LENGTH: 89
<212> TYPE: PRT
<213> ORGANISM: Zea mays
<220> FEATURE:
<221> NAME/KEY: misc_feature
<222> LOCATION: (1)..(89)
<223> OTHER INFORMATION: Ceres CLONE ID no. 503296
<220> FEATURE:
<221> NAME/KEY: misc_feature
<222> LOCATION: (1)..(89)
<223> OTHER INFORMATION: Functional Homolog of CERES CLONE ID no. 519
      at SEQ ID NO. 87
      with e-value of 2.50E-16 and percent identity of 55.42169
<220> FEATURE:
<221> NAME/KEY: misc_feature
<222> LOCATION: (1)..(89)
<223> OTHER INFORMATION: Functional Homolog of CERES CLONE ID no. 4734
      at SEQ ID NO. 85
      with e-value of and 9.40E-17 percent identity of 50.58824
<220> FEATURE:
<221> NAME/KEY: misc_feature
<222> LOCATION: (1)..(89)
<223> OTHER INFORMATION: Functional Homolog of CERES CLONE ID no. 8607
      at SEQ ID NO. 97
      with e-value of and 9.40E-17 percent identity of 50.58824
<220> FEATURE:
<221> NAME/KEY: misc_feature
<222> LOCATION: (1)..(89)
<223> OTHER INFORMATION: Functional Homolog of CERES CLONE ID no.
      336524 at SEQ ID NO. 83
      with e-value of 4.40E-26 and percent identity of 77.5
<220> FEATURE:
<221> NAME/KEY: misc_feature
<222> LOCATION: (1)..(89)
<223> OTHER INFORMATION: Functional Homolog of CERES CLONE ID no.
      560681 at SEQ ID NO. 89
      with e-value of 2.10E-19 and percent identity of 56.47059
<220> FEATURE:
<221> NAME/KEY: misc_feature
<222> LOCATION: (1)..(89)
<223> OTHER INFORMATION: Functional Homolog of CERES CLONE ID no.
      560948 at SEQ ID NO. 91
      with e-value of 1.30E-17 and percent identity of 56.32184
<220> FEATURE:
<221> NAME/KEY: misc_feature
<222> LOCATION: (1)..(89)
<223> OTHER INFORMATION: Functional Homolog of CERES CLONE ID no.
      653656 at SEQ ID NO. 93
      with e-value of 9.10E-19 and percent identity of 59.03614
<220> FEATURE:
<221> NAME/KEY: misc_feature
<222> LOCATION: (1)..(89)
<223> OTHER INFORMATION: Functional Homolog of CERES CLONE ID no.
      733804 at SEQ ID NO. 95
      with e-value of 1.70E-19 and percent identity of 57.47126

<400> SEQUENCE: 112

Met Ser Ser Arg Arg Pro Ser Ser Arg Gly Asn Ile Ser Glu Asp Glu
1               5                   10                  15

Ile Asn Glu Leu Ile Ser Lys Leu Gln Ala Leu Leu Pro Ser Ser Arg
            20                  25                  30

Arg Arg Gly Ser Gly Gln Ala Ser Thr Thr Lys Leu Leu Lys Glu Thr
        35                  40                  45

Cys Ser Tyr Ile Lys Ser Leu His Arg Glu Val Asp Asp Leu Ser Asp
    50                  55                  60

Arg Leu Ser Asp Leu Met Ala Thr Met Asp His Asn Ser Pro Gly Ala
65                  70                  75                  80

Glu Ile Ile Arg Ser Ile Leu Arg Ser
            85
```